United States Patent
Argento et al.

(10) Patent No.: US 11,141,263 B2
(45) Date of Patent: *Oct. 12, 2021

(54) MULTI-PIECE ACCOMMODATING INTRAOCULAR LENS

(71) Applicant: Shifamed Holdings, LLC, Campbell, CA (US)

(72) Inventors: Claudio Argento, Felton, CA (US); Tom Saul, Moss Beach, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 434 days.

This patent is subject to a terminal disclaimer.

(21) Appl. No.: 15/776,380

(22) PCT Filed: Nov. 15, 2016

(86) PCT No.: PCT/US2016/061977
§ 371 (c)(1),
(2) Date: May 15, 2018

(87) PCT Pub. No.: WO2017/087358
PCT Pub. Date: May 26, 2017

(65) Prior Publication Data
US 2020/0008931 A1   Jan. 9, 2020

Related U.S. Application Data

(60) Provisional application No. 62/257,087, filed on Nov. 18, 2015, provisional application No. 62/300,695, (Continued)

(51) Int. Cl.
*A61F 2/16* (2006.01)

(52) U.S. Cl.
CPC .......... *A61F 2/1635* (2013.01); *A61F 2/1601* (2015.04); *A61F 2/1645* (2015.04);
(Continued)

(58) Field of Classification Search
CPC .... A61F 2/1635; A61F 2/1629; A61F 2/1601; A61F 2/1648; A61F 2002/1682; A61F 2002/16901; A61F 2002/169053
See application file for complete search history.

(56) References Cited

U.S. PATENT DOCUMENTS

| 4,440,918 A | 4/1984 | Rice et al. |
| 4,663,409 A | 5/1987 | Friends et al. |

(Continued)

FOREIGN PATENT DOCUMENTS

| AU | 2006200142 A1 | 7/2006 |
| AU | 2015361227 | 4/2014 |

(Continued)

OTHER PUBLICATIONS

European Extended Search Report dated Jul. 2, 2019 for European Patent Application No. 16866930.7, Applicant: Shifamed Holdings, LLC, filing date: Nov. 15, 2016, 8 pages.

(Continued)

*Primary Examiner* — Jennifer Dieterle
*Assistant Examiner* — Tiffany P Shipmon
(74) *Attorney, Agent, or Firm* — Perkins Coie LLP

(57) ABSTRACT

An accommodating intraocular lens (AIOL) for implantation within a capsular bag of a patient's eye comprises first and second components coupled together to define an inner fluid chamber and an outer fluid reservoir. The inner region of the AIOL provides optical power with one or more of the shaped fluid within the inner fluid chamber or the shape of the first or second components. The fluid reservoir comprises a bellows region with fold(s) extending circumferentially around an optical axis of the eye. The bellows engages the lens capsule, and a compliant fold region between inner and outer bellows portions allows the profile of the AIOL to deflect when the eye accommodates for near vision. Fluid (Continued)

transfers between the inner fluid chamber and the outer fluid reservoir to provide optical power changes. A third lens component coupled to the first or second component provides additional optical power.

12 Claims, 35 Drawing Sheets

Related U.S. Application Data filed on Feb. 26, 2016, provisional application No. 62/331,407, filed on May 3, 2016, provisional application No. 62/331,946, filed on May 4, 2016, provisional application No. 62/334,998, filed on May 11, 2016, provisional application No. 62/344,691, filed on Jun. 2, 2016, provisional application No. 62/362,896, filed on Jul. 15, 2016.

(52) U.S. Cl.
CPC .... *A61F 2/1648* (2013.01); *A61F 2002/1681* (2013.01); *A61F 2220/005* (2013.01); *A61F 2220/0033* (2013.01)

(56) References Cited

U.S. PATENT DOCUMENTS

| | | | |
|---|---|---|---|
| 4,709,996 A | 12/1987 | Michelson et al. | |
| 4,731,078 A | 3/1988 | Stoy et al. | |
| 4,731,080 A | 3/1988 | Galin | |
| 4,842,601 A | 6/1989 | Smith et al. | |
| 4,892,543 A * | 1/1990 | Turley | A61F 2/1613 623/6.13 |
| 4,932,966 A | 6/1990 | McMaster et al. | |
| 4,932,971 A * | 6/1990 | Kelman | A61F 2/1648 623/6.34 |
| 5,074,942 A | 12/1991 | Orlosky et al. | |
| 5,211,662 A | 5/1993 | Barrett et al. | |
| 5,217,491 A | 6/1993 | Vanderbilt | |
| 5,366,502 A * | 11/1994 | Patel | A61F 2/1602 623/6.27 |
| 5,405,386 A | 4/1995 | Rheinish et al. | |
| 5,423,929 A | 6/1995 | Grisoni et al. | |
| 5,489,302 A | 2/1996 | Skottun | |
| 5,556,929 A | 9/1996 | Yokoyama et al. | |
| 5,612,391 A | 3/1997 | Chabrecek et al. | |
| 5,620,720 A | 4/1997 | Glick et al. | |
| 5,807,944 A | 9/1998 | Hirt et al. | |
| 5,891,931 A | 4/1999 | Leboeuf et al. | |
| 5,914,355 A | 6/1999 | Kuenzler | |
| 5,944,753 A | 8/1999 | Galin et al. | |
| 5,945,465 A | 8/1999 | Ozark et al. | |
| 5,945,498 A | 8/1999 | Lohmann et al. | |
| 6,140,438 A | 10/2000 | Kawaguchi et al. | |
| 6,346,594 B1 | 2/2002 | Watanabe et al. | |
| 6,447,920 B1 | 9/2002 | Chabrecek et al. | |
| 6,465,056 B1 | 10/2002 | Chabrecek et al. | |
| 6,521,352 B1 | 2/2003 | Lohmann et al. | |
| 6,537,316 B1 | 3/2003 | Chambers | |
| 6,558,420 B2 | 5/2003 | Green et al. | |
| 6,582,754 B1 | 6/2003 | Pasic et al. | |
| 6,586,038 B1 | 7/2003 | Chabrecek et al. | |
| 6,630,243 B2 | 10/2003 | Ozark et al. | |
| 6,660,035 B1 | 12/2003 | Yaross et al. | |
| 6,685,741 B2 | 2/2004 | Landreville et al. | |
| 6,695,881 B2 * | 2/2004 | Peng | A61F 2/1613 623/6.34 |
| 6,713,583 B2 | 3/2004 | Liao et al. | |
| 6,730,123 B1 | 5/2004 | Klopotek et al. | |
| 6,734,321 B2 | 5/2004 | Chabrecek et al. | |
| 6,747,090 B2 | 6/2004 | Haitjema et al. | |
| 6,761,737 B2 | 7/2004 | Ting et al. | |
| 6,764,511 B2 | 7/2004 | Ting et al. | |
| 6,767,363 B1 | 7/2004 | Green et al. | |
| 6,767,979 B1 | 7/2004 | Muir et al. | |
| 6,786,934 B2 | 9/2004 | Ting et al. | |
| 6,797,004 B1 * | 9/2004 | Brady | A61F 2/1648 623/6.4 |
| 6,818,017 B1 | 11/2004 | Shu et al. | |
| 6,818,158 B2 | 11/2004 | Pham et al. | |
| 6,835,410 B2 | 12/2004 | Chabrecek et al. | |
| 6,846,326 B2 | 1/2005 | Nguyen et al. | |
| 6,858,040 B2 | 2/2005 | Ting et al. | |
| 6,884,261 B2 | 4/2005 | Zadno-Azizi et al. | |
| 6,893,595 B1 | 5/2005 | Muir et al. | |
| 6,893,685 B2 | 5/2005 | Pasic et al. | |
| 6,899,732 B2 | 5/2005 | Zadno-Azizi et al. | |
| 6,935,743 B2 | 8/2005 | Shadduck | |
| 6,969,403 B2 | 11/2005 | Yang et al. | |
| 7,041,134 B2 | 5/2006 | Ting et al. | |
| 7,087,080 B2 | 8/2006 | Ting et al. | |
| 7,097,660 B2 * | 8/2006 | Portney | A61F 2/1602 623/6.22 |
| 7,118,596 B2 | 10/2006 | Ting et al. | |
| 7,198,640 B2 | 4/2007 | Nguyen | |
| 7,217,778 B2 | 5/2007 | Flipsen et al. | |
| 7,226,478 B2 | 6/2007 | Ting et al. | |
| 7,300,464 B2 * | 11/2007 | Tran | A61F 2/1629 623/6.41 |
| 7,416,562 B2 | 8/2008 | Gross et al. | |
| 7,438,723 B2 | 10/2008 | Esch | |
| 7,452,378 B2 | 11/2008 | Ting et al. | |
| 7,468,397 B2 | 12/2008 | Schorzman et al. | |
| 7,479,530 B2 | 1/2009 | Chan et al. | |
| 7,557,231 B2 | 7/2009 | Schorzman et al. | |
| 7,588,334 B2 | 9/2009 | Matsushita et al. | |
| 7,591,849 B2 | 9/2009 | Richardson et al. | |
| 7,601,766 B2 | 10/2009 | Schorzman et al. | |
| 7,637,947 B2 | 12/2009 | Scholl et al. | |
| 7,714,090 B2 | 5/2010 | Iwamoto et al. | |
| 7,744,603 B2 | 6/2010 | Zadno-Azizi et al. | |
| 7,744,646 B2 | 6/2010 | Zadno-Azizi et al. | |
| 7,781,558 B2 | 8/2010 | Schorzman et al. | |
| 7,806,929 B2 | 10/2010 | Brown et al. | |
| 7,806,930 B2 | 10/2010 | Brown et al. | |
| 7,842,087 B2 | 11/2010 | Ben Nun | |
| 7,883,540 B2 | 2/2011 | Niwa et al. | |
| 7,906,563 B2 | 3/2011 | Huang et al. | |
| 7,942,929 B2 | 5/2011 | Linhardt et al. | |
| 8,003,710 B2 | 8/2011 | Medina et al. | |
| 8,025,823 B2 | 9/2011 | Figueroa et al. | |
| 8,034,107 B2 | 10/2011 | Stenger et al. | |
| 8,048,155 B2 | 11/2011 | Shadduck et al. | |
| 8,071,703 B2 | 12/2011 | Zhou et al. | |
| 8,105,623 B2 | 1/2012 | Schorzman et al. | |
| 8,158,712 B2 | 4/2012 | Your | |
| 8,187,325 B2 | 5/2012 | Zadno-Azizi et al. | |
| 8,211,955 B2 | 7/2012 | Chang et al. | |
| 8,222,360 B2 | 7/2012 | Liao | |
| 8,251,509 B2 | 8/2012 | Zickler et al. | |
| 8,283,429 B2 | 10/2012 | Zhou et al. | |
| 8,328,869 B2 | 12/2012 | Burns et al. | |
| 8,357,771 B2 | 1/2013 | Medina et al. | |
| 8,377,123 B2 | 2/2013 | Zadno et al. | |
| 8,414,646 B2 | 4/2013 | Gifford et al. | |
| 8,420,711 B2 | 4/2013 | Awasthi et al. | |
| 8,425,595 B2 | 4/2013 | Evans et al. | |
| 8,425,599 B2 | 4/2013 | Shadduck et al. | |
| 8,425,926 B2 | 4/2013 | Qiu et al. | |
| 8,430,928 B2 | 4/2013 | Liao | |
| 8,454,688 B2 | 6/2013 | Evans et al. | |
| 8,486,142 B2 | 7/2013 | Bumbalough et al. | |
| 8,500,806 B1 | 8/2013 | Phillips et al. | |
| 8,585,758 B2 | 11/2013 | Woods | |
| 8,603,166 B2 | 12/2013 | Park | |
| 8,609,745 B2 | 12/2013 | Medina et al. | |
| 8,663,510 B2 | 3/2014 | Graney et al. | |
| 8,680,172 B2 | 3/2014 | Liao | |
| 8,728,158 B2 | 5/2014 | Whitsett | |
| 8,759,414 B2 | 6/2014 | Winter et al. | |
| 8,784,485 B2 | 7/2014 | Evans et al. | |
| 8,827,447 B2 | 9/2014 | Awasthi et al. | |

(56) References Cited

U.S. PATENT DOCUMENTS

| | | | |
|---|---|---|---|
| 8,834,566 B1 * | 9/2014 | Jones | A61F 2/1648 623/6.22 |
| 8,835,525 B2 | 9/2014 | Chang et al. | |
| 8,851,670 B2 | 10/2014 | Zickler et al. | |
| 8,863,749 B2 | 10/2014 | Gooding et al. | |
| 8,877,227 B2 | 11/2014 | Ravi | |
| 8,899,745 B2 | 12/2014 | Domschke | |
| 8,900,298 B2 | 12/2014 | Chazan et al. | |
| 8,956,409 B2 | 2/2015 | Ben | |
| 8,968,399 B2 | 3/2015 | Ghabra | |
| 8,992,609 B2 | 3/2015 | Shadduck | |
| 8,993,651 B2 | 3/2015 | Chang et al. | |
| 9,005,492 B2 | 4/2015 | Chang et al. | |
| 9,005,700 B2 | 4/2015 | Qiu et al. | |
| 9,006,359 B2 | 4/2015 | Schultz et al. | |
| 9,011,532 B2 | 4/2015 | Catlin et al. | |
| 9,023,915 B2 | 5/2015 | Hu et al. | |
| 9,034,035 B2 | 5/2015 | Assia et al. | |
| 9,039,174 B2 | 5/2015 | Awasthi et al. | |
| 9,044,302 B2 | 6/2015 | Gooding et al. | |
| 9,052,439 B2 | 6/2015 | Samuel et al. | |
| 9,052,440 B2 | 6/2015 | Chang et al. | |
| 9,095,424 B2 | 8/2015 | Atkinson et al. | |
| 9,097,840 B2 | 8/2015 | Chang et al. | |
| 9,125,736 B2 | 9/2015 | Atkinson et al. | |
| 9,186,244 B2 | 11/2015 | Rao et al. | |
| 9,198,572 B2 | 12/2015 | Zickler et al. | |
| 9,198,752 B2 * | 12/2015 | Woods | A61F 2/1601 |
| 9,254,189 B2 | 2/2016 | Azar et al. | |
| 9,265,604 B2 | 2/2016 | Woods | |
| 9,280,000 B2 | 3/2016 | Simonov et al. | |
| 9,289,287 B2 | 3/2016 | Atkinson et al. | |
| 9,326,848 B2 | 5/2016 | Woods | |
| 9,364,316 B1 | 6/2016 | Kahook et al. | |
| 9,387,069 B2 | 7/2016 | Atkinson et al. | |
| 9,398,949 B2 | 7/2016 | Werblin | |
| 9,421,088 B1 | 8/2016 | Schieber et al. | |
| 9,427,312 B2 | 8/2016 | Tai et al. | |
| 9,456,895 B2 | 10/2016 | Shadduck et al. | |
| 9,486,311 B2 | 11/2016 | Vaughan et al. | |
| 9,498,326 B2 | 11/2016 | Tsai et al. | |
| 9,603,703 B2 | 3/2017 | Bumbalough | |
| 9,622,855 B2 | 4/2017 | Portney et al. | |
| 9,636,213 B2 | 5/2017 | Brady | |
| 9,655,775 B2 | 5/2017 | Boukhny et al. | |
| 9,681,946 B2 | 6/2017 | Kahook et al. | |
| 9,693,858 B2 | 7/2017 | Hildebrand et al. | |
| 9,744,027 B2 | 8/2017 | Jansen | |
| 9,795,473 B2 | 10/2017 | Smiley et al. | |
| 9,814,568 B2 * | 11/2017 | Ben Nun | A61F 2/1629 |
| 9,907,881 B2 | 3/2018 | Terrisse | |
| 10,195,018 B2 | 2/2019 | Salahieh et al. | |
| 10,350,056 B2 | 7/2019 | Argento et al. | |
| 10,350,057 B2 | 7/2019 | Argento et al. | |
| 10,526,353 B2 | 1/2020 | Silvestrini | |
| 10,548,718 B2 | 2/2020 | Salahieh et al. | |
| 10,709,549 B2 | 7/2020 | Argento et al. | |
| 10,736,734 B2 | 8/2020 | Salahieh et al. | |
| 2001/0037001 A1 | 11/2001 | Muller et al. | |
| 2001/0056165 A1 | 12/2001 | Mentak et al. | |
| 2002/0072795 A1 | 6/2002 | Green et al. | |
| 2002/0086160 A1 | 7/2002 | Qiu et al. | |
| 2002/0102415 A1 | 8/2002 | Valint, Jr. et al. | |
| 2002/0103536 A1 | 8/2002 | Landreville et al. | |
| 2002/0107568 A1 | 8/2002 | Zadno-Azizi et al. | |
| 2002/0111678 A1 | 8/2002 | Zadno-Azizi et al. | |
| 2002/0116057 A1 | 8/2002 | Ting et al. | |
| 2002/0116058 A1 | 8/2002 | Zadno-Azizi et al. | |
| 2002/0116059 A1 | 8/2002 | Zadno-Azizi et al. | |
| 2002/0116060 A1 | 8/2002 | Nguyen et al. | |
| 2002/0116061 A1 | 8/2002 | Zadno-Azizi et al. | |
| 2002/0138141 A1 | 9/2002 | Zadno-Azizi et al. | |
| 2002/0173847 A1 | 11/2002 | Pham et al. | |
| 2002/0197414 A1 | 12/2002 | Chabrecek et al. | |
| 2003/0008063 A1 | 1/2003 | Chabrecek et al. | |
| 2003/0074060 A1 | 4/2003 | Zadno-Azizi et al. | |
| 2003/0074061 A1 | 4/2003 | Pham et al. | |
| 2003/0078656 A1 | 4/2003 | Nguyen | |
| 2003/0078657 A1 | 4/2003 | Zadno-Azizi et al. | |
| 2003/0078658 A1 | 4/2003 | Zadno-Azizi | |
| 2003/0100666 A1 | 5/2003 | DeGroot et al. | |
| 2003/0158560 A1 | 8/2003 | Portney | |
| 2003/0162929 A1 | 8/2003 | Verbruggen et al. | |
| 2003/0224185 A1 | 12/2003 | Valint, Jr. et al. | |
| 2004/0082993 A1 * | 4/2004 | Woods | A61F 2/1635 623/6.28 |
| 2004/0111152 A1 | 6/2004 | Kelman et al. | |
| 2004/0166232 A1 | 8/2004 | Kunzler et al. | |
| 2004/0169816 A1 | 9/2004 | Esch | |
| 2004/0184158 A1 | 9/2004 | Shadduck | |
| 2004/0230300 A1 | 11/2004 | Bandhauer et al. | |
| 2005/0013842 A1 | 1/2005 | Qiu et al. | |
| 2005/0049700 A1 | 3/2005 | Zadno-Azizi et al. | |
| 2005/0055092 A1 | 3/2005 | Nguyen et al. | |
| 2005/0149183 A1 | 7/2005 | Shadduck et al. | |
| 2005/0153055 A1 | 7/2005 | Ammon et al. | |
| 2005/0165410 A1 | 7/2005 | Zadno-Azizi et al. | |
| 2005/0228120 A1 | 10/2005 | Hughes et al. | |
| 2005/0228401 A1 | 10/2005 | Zadno-Azizi et al. | |
| 2006/0069432 A1 | 3/2006 | Tran | |
| 2006/0100701 A1 | 5/2006 | Esch et al. | |
| 2006/0100703 A1 | 5/2006 | Evans et al. | |
| 2006/0116765 A1 | 6/2006 | Blake et al. | |
| 2006/0178741 A1 | 8/2006 | Zadno-Azizi et al. | |
| 2006/0241752 A1 | 10/2006 | Israel | |
| 2006/0259139 A1 | 11/2006 | Zadno-Azizi et al. | |
| 2006/0271187 A1 | 11/2006 | Zadno-Azizi et al. | |
| 2007/0027540 A1 | 2/2007 | Zadno-Azizi et al. | |
| 2007/0050025 A1 | 3/2007 | Nguyen et al. | |
| 2007/0078515 A1 * | 4/2007 | Brady | A61F 2/1648 623/6.37 |
| 2007/0088433 A1 | 4/2007 | Esch et al. | |
| 2007/0092830 A1 | 4/2007 | Lai et al. | |
| 2007/0106377 A1 | 5/2007 | Smith et al. | |
| 2007/0108643 A1 | 5/2007 | Zadno-Azizi et al. | |
| 2007/0122540 A1 | 5/2007 | Salamone et al. | |
| 2007/0201138 A1 | 8/2007 | Lo et al. | |
| 2007/0203317 A1 | 8/2007 | Verbruggen et al. | |
| 2001/0213817 | 9/2007 | Esch et al. | |
| 2007/0213817 | 9/2007 | Esch et al. | |
| 2007/0232755 A1 | 10/2007 | Matsushita et al. | |
| 2007/0269488 A1 | 11/2007 | Ravi et al. | |
| 2008/0001318 A1 | 1/2008 | Schorzman et al. | |
| 2008/0003259 A1 | 1/2008 | Salamone et al. | |
| 2008/0003261 A1 | 1/2008 | Schorzman et al. | |
| 2008/0015689 A1 | 1/2008 | Esch et al. | |
| 2008/0027461 A1 | 1/2008 | Vaquero et al. | |
| 2008/0046074 A1 | 2/2008 | Smith et al. | |
| 2008/0076897 A1 | 3/2008 | Kunzler et al. | |
| 2008/0139769 A1 | 6/2008 | Iwamoto et al. | |
| 2008/0143958 A1 | 6/2008 | Medina et al. | |
| 2008/0181931 A1 | 7/2008 | Qiu et al. | |
| 2008/0234457 A1 | 9/2008 | Zhou et al. | |
| 2008/0300680 A1 * | 12/2008 | Joshua | A61F 2/1624 623/6.37 |
| 2008/0314767 A1 | 12/2008 | Lai et al. | |
| 2009/0043384 A1 * | 2/2009 | Niwa | A61F 2/1648 623/6.13 |
| 2009/0076603 A1 | 3/2009 | Avery et al. | |
| 2009/0118739 A1 | 5/2009 | Kappelhof et al. | |
| 2009/0143499 A1 | 6/2009 | Chang et al. | |
| 2009/0168012 A1 | 7/2009 | Linhardt et al. | |
| 2009/0170976 A1 | 7/2009 | Huang et al. | |
| 2009/0171459 A1 | 7/2009 | Linhardt et al. | |
| 2009/0204210 A1 | 8/2009 | Pynson | |
| 2009/0232871 A1 | 9/2009 | Hitz et al. | |
| 2009/0247661 A1 | 10/2009 | Müller-Lierheim Wolfgang et al. | |
| 2009/0292355 A1 | 11/2009 | Boyd et al. | |
| 2010/0016964 A1 * | 1/2010 | Werblin | A61F 2/1648 623/6.34 |
| 2010/0119744 A1 | 5/2010 | Yokoyama et al. | |
| 2010/0120938 A1 | 5/2010 | Phelan et al. | |
| 2010/0120939 A1 | 5/2010 | Phelan et al. | |
| 2010/0121444 A1 | 5/2010 | Ben et al. | |

(56) References Cited

U.S. PATENT DOCUMENTS

| | | |
|---|---|---|
| 2010/0160482 A1 | 6/2010 | Nachbaur et al. |
| 2010/0179653 A1 | 7/2010 | Argento et al. |
| 2010/0211170 A1 | 8/2010 | Liao et al. |
| 2010/0228346 A1 | 9/2010 | Esch et al. |
| 2010/0239633 A1 | 9/2010 | Strome et al. |
| 2010/0324674 A1 | 12/2010 | Brown et al. |
| 2011/0009519 A1 | 1/2011 | Awasthi et al. |
| 2011/0046332 A1 | 2/2011 | Breiner et al. |
| 2011/0112636 A1* | 5/2011 | Ben Nun ............ A61F 2/1635 623/6.37 |
| 2011/0118379 A1 | 5/2011 | Tighe et al. |
| 2011/0118834 A1 | 5/2011 | Lo et al. |
| 2011/0133350 A1 | 6/2011 | Qiu et al. |
| 2011/0140292 A1 | 6/2011 | Chang et al. |
| 2011/0144228 A1 | 6/2011 | Ravi et al. |
| 2011/0269869 A1 | 11/2011 | Medina et al. |
| 2011/0282442 A1 | 11/2011 | Scholl et al. |
| 2011/0295368 A1 | 12/2011 | Betser et al. |
| 2012/0010321 A1 | 1/2012 | Chang et al. |
| 2012/0023869 A1 | 2/2012 | Samuel et al. |
| 2012/0033183 A1 | 2/2012 | Dai et al. |
| 2012/0041097 A1 | 2/2012 | Zhou et al. |
| 2012/0046743 A1 | 2/2012 | Pinchuk et al. |
| 2012/0063000 A1 | 3/2012 | Batchko et al. |
| 2012/0078363 A1 | 3/2012 | Lu |
| 2012/0078364 A1 | 3/2012 | Stenger |
| 2012/0088843 A1 | 4/2012 | Chang et al. |
| 2012/0088844 A1 | 4/2012 | Kuyu et al. |
| 2012/0088861 A1 | 4/2012 | Huang et al. |
| 2012/0115979 A1 | 5/2012 | Chang et al. |
| 2012/0147323 A1 | 6/2012 | Domschke et al. |
| 2012/0238857 A1 | 9/2012 | Wong et al. |
| 2012/0245684 A1 | 9/2012 | Liao et al. |
| 2012/0314183 A1 | 12/2012 | Nakamura et al. |
| 2012/0330415 A1 | 12/2012 | Callahan et al. |
| 2013/0013060 A1 | 1/2013 | Zadno-Azizi et al. |
| 2013/0053954 A1 | 2/2013 | Rao et al. |
| 2013/0095235 A1 | 4/2013 | Bothe et al. |
| 2013/0106007 A1 | 5/2013 | Medina et al. |
| 2013/0110234 A1* | 5/2013 | DeVita ............ A61F 2/1616 623/6.34 |
| 2013/0116781 A1 | 5/2013 | Ben et al. |
| 2013/0150961 A1 | 6/2013 | Evans et al. |
| 2013/0176628 A1 | 7/2013 | Batchko et al. |
| 2013/0197125 A1 | 8/2013 | Awasthi et al. |
| 2013/0224309 A1 | 8/2013 | Qiu et al. |
| 2013/0228943 A1 | 9/2013 | Qiu et al. |
| 2013/0245756 A1 | 9/2013 | Liao et al. |
| 2013/0289294 A1 | 10/2013 | Awasthi et al. |
| 2013/0304203 A1 | 11/2013 | Beer |
| 2013/0317607 A1 | 11/2013 | DeBoer et al. |
| 2014/0055750 A1 | 2/2014 | Dai et al. |
| 2014/0171539 A1 | 6/2014 | Chang et al. |
| 2014/0171542 A1 | 6/2014 | Chang |
| 2014/0178595 A1 | 6/2014 | Bothe et al. |
| 2014/0180403 A1* | 6/2014 | Silvestrini ............ A61F 2/16 623/6.4 |
| 2014/0180406 A1 | 6/2014 | Simpson |
| 2014/0180407 A1 | 6/2014 | Sohn et al. |
| 2014/0228949 A1 | 8/2014 | Argento et al. |
| 2014/0277439 A1 | 9/2014 | Hu et al. |
| 2014/0309735 A1 | 10/2014 | Sohn et al. |
| 2014/0316521 A1 | 10/2014 | McLeod et al. |
| 2014/0350124 A1 | 11/2014 | Chang et al. |
| 2014/0379079 A1 | 12/2014 | Ben |
| 2015/0088149 A1 | 3/2015 | Auld |
| 2015/0092155 A1 | 4/2015 | Chang et al. |
| 2015/0105760 A1 | 4/2015 | Silvestrini et al. |
| 2015/0152228 A1 | 6/2015 | Chang et al. |
| 2015/0164321 A1 | 6/2015 | Weibel et al. |
| 2015/0177417 A1 | 6/2015 | Goshima et al. |
| 2015/0351901 A1 | 12/2015 | Chicevic et al. |
| 2016/0000558 A1* | 1/2016 | Honigsbaum ........ A61F 2/1694 623/6.15 |
| 2016/0008126 A1 | 1/2016 | Vaughan et al. |
| 2016/0030161 A1* | 2/2016 | Brady ............ A61F 2/1635 623/6.13 |
| 2016/0058553 A1 | 3/2016 | Vaughan et al. |
| 2016/0074154 A1 | 3/2016 | Woods |
| 2016/0100938 A1 | 4/2016 | Weeber et al. |
| 2016/0128826 A1 | 5/2016 | Rao et al. |
| 2016/0151150 A1 | 6/2016 | Sato |
| 2016/0184091 A1 | 6/2016 | Burns et al. |
| 2016/0184092 A1 | 6/2016 | Flaherty et al. |
| 2016/0250020 A1 | 9/2016 | Schieber et al. |
| 2016/0256265 A1 | 9/2016 | Borja et al. |
| 2016/0262875 A1 | 9/2016 | Smiley et al. |
| 2016/0278914 A1 | 9/2016 | Sato et al. |
| 2016/0296320 A1 | 10/2016 | Humayun et al. |
| 2016/0296662 A1 | 10/2016 | Dudic et al. |
| 2016/0317286 A1* | 11/2016 | Brady ............ A61F 2/1635 |
| 2016/0317287 A1 | 11/2016 | Rao et al. |
| 2016/0331587 A1 | 11/2016 | Ueno et al. |
| 2016/0361157 A1 | 12/2016 | Honigsbaum |
| 2017/0000602 A1 | 1/2017 | Sohn et al. |
| 2017/0020662 A1 | 1/2017 | Shadduck |
| 2017/0049561 A1 | 2/2017 | Smiley et al. |
| 2017/0049562 A1 | 2/2017 | Argento et al. |
| 2017/0119521 A1 | 5/2017 | Kahook et al. |
| 2017/0258581 A1* | 9/2017 | Borja ............ A61F 2/1648 |
| 2017/0348094 A1 | 12/2017 | Sohn et al. |
| 2018/0110613 A1 | 4/2018 | Wortz et al. |
| 2018/0161152 A1 | 6/2018 | Argento et al. |
| 2018/0177589 A1 | 6/2018 | Argento et al. |
| 2019/0159890 A1 | 5/2019 | Salahieh et al. |
| 2019/0274823 A1 | 9/2019 | Argento et al. |
| 2020/0146813 A1 | 5/2020 | Argento et al. |
| 2020/0306031 A1 | 10/2020 | Salahieh et al. |
| 2020/0397566 A1 | 12/2020 | Salahieh et al. |

FOREIGN PATENT DOCUMENTS

| | | |
|---|---|---|
| AU | 2015361227 | 4/2017 |
| AU | 2010203427 | 5/2017 |
| AU | 2012335677 | 6/2017 |
| AU | 2013335677 | 6/2017 |
| AU | 2015258287 | 12/2017 |
| CA | 2973684 | 7/2016 |
| CA | 2974639 | 8/2016 |
| CA | 2987311 | 12/2016 |
| CA | 2752046 | 4/2017 |
| CA | 2829143 | 4/2017 |
| CN | 101351169 | 6/2007 |
| CN | 101031257 | 9/2007 |
| CN | 101547663 | 9/2009 |
| CN | 102271623 | 7/2010 |
| CN | 108472129 | 8/2018 |
| EP | 01-223970 | 9/1989 |
| EP | 0604369 A1 | 6/1994 |
| EP | 0734269 A1 | 10/1996 |
| EP | 0784652 A1 | 7/1997 |
| EP | 0800511 A1 | 10/1997 |
| EP | 0820601 A1 | 1/1998 |
| EP | 0826158 A1 | 3/1998 |
| EP | 0898972 A2 | 3/1999 |
| EP | 0907668 A1 | 4/1999 |
| EP | 0930357 A1 | 7/1999 |
| EP | 0604369 B1 | 8/1999 |
| EP | 0826158 B1 | 9/1999 |
| EP | 0947856 A2 | 10/1999 |
| EP | 0820601 B1 | 12/1999 |
| EP | 0800511 B1 | 1/2000 |
| EP | 0989138 A2 | 3/2000 |
| EP | 1084428 A1 | 3/2001 |
| EP | 1088246 A1 | 4/2001 |
| EP | 1090313 A1 | 4/2001 |
| EP | 1095711 A2 | 5/2001 |
| EP | 1095965 A1 | 5/2001 |
| EP | 1095966 A2 | 5/2001 |
| EP | 1109853 A1 | 6/2001 |
| EP | 0907668 B1 | 9/2001 |
| EP | 1141054 A1 | 10/2001 |
| EP | 1187873 A1 | 3/2002 |
| EP | 1200019 A1 | 5/2002 |

(56) References Cited

FOREIGN PATENT DOCUMENTS

| | | |
|---|---|---|
| EP | 1227773 A1 | 8/2002 |
| EP | 1230041 A2 | 8/2002 |
| EP | 1266246 A1 | 12/2002 |
| EP | 0898972 B1 | 4/2003 |
| EP | 1341485 A1 | 9/2003 |
| EP | 1364663 A1 | 11/2003 |
| EP | 1095711 B1 | 1/2004 |
| EP | 1141054 B1 | 2/2004 |
| EP | 1395302 A1 | 3/2004 |
| EP | 1410074 A1 | 4/2004 |
| EP | 1266246 B1 | 6/2004 |
| EP | 1109853 B1 | 9/2004 |
| EP | 1187873 B1 | 9/2004 |
| EP | 1084428 B2 | 11/2004 |
| EP | 1472305 A1 | 11/2004 |
| EP | 1230041 B1 | 12/2004 |
| EP | 0989138 B1 | 2/2005 |
| EP | 1095965 B1 | 2/2005 |
| EP | 1395302 B1 | 2/2005 |
| EP | 1507811 A1 | 2/2005 |
| EP | 1524953 A2 | 4/2005 |
| EP | 1200019 B1 | 9/2005 |
| EP | 1095966 B1 | 1/2006 |
| EP | 1660153 A2 | 5/2006 |
| EP | 1353611 B1 | 9/2006 |
| EP | 1696975 A1 | 9/2006 |
| EP | 1341485 B1 | 11/2006 |
| EP | 1723933 A2 | 11/2006 |
| EP | 1723934 A2 | 11/2006 |
| EP | 1750157 A1 | 2/2007 |
| EP | 1088246 B1 | 11/2007 |
| EP | 1857477 A1 | 11/2007 |
| EP | 1227773 B1 | 1/2008 |
| EP | 1888660 A2 | 2/2008 |
| EP | 1890650 A2 | 2/2008 |
| EP | 1902737 A1 | 3/2008 |
| EP | 1723933 B1 | 11/2008 |
| EP | 2035050 A2 | 3/2009 |
| EP | 2035480 A1 | 3/2009 |
| EP | 2035486 A1 | 3/2009 |
| EP | 1723934 B1 | 6/2009 |
| EP | 2066732 A2 | 6/2009 |
| EP | 2077292 A1 | 7/2009 |
| EP | 2092376 A1 | 8/2009 |
| EP | 1648534 B1 | 9/2009 |
| EP | 2094193 A2 | 9/2009 |
| EP | 2109784 A1 | 10/2009 |
| EP | 2120789 A2 | 11/2009 |
| EP | 2126614 A2 | 12/2009 |
| EP | 2035480 B1 | 2/2010 |
| EP | 2170708 A2 | 4/2010 |
| EP | 2185589 A2 | 5/2010 |
| EP | 2231207 A1 | 9/2010 |
| EP | 1750157 B1 | 10/2010 |
| EP | 2235094 A1 | 10/2010 |
| EP | 2276513 A2 | 1/2011 |
| EP | 2292672 A2 | 3/2011 |
| EP | 2356170 A1 | 8/2011 |
| EP | 2356497 A2 | 8/2011 |
| EP | 2109784 B1 | 10/2011 |
| EP | 2396355 A2 | 12/2011 |
| EP | 2035486 B1 | 4/2012 |
| EP | 2452212 A2 | 5/2012 |
| EP | 1857477 B1 | 6/2012 |
| EP | 1410074 B1 | 10/2012 |
| EP | 2092376 B1 | 10/2012 |
| EP | 2510051 A1 | 10/2012 |
| EP | 2513711 A1 | 10/2012 |
| EP | 2514791 A1 | 10/2012 |
| EP | 2356170 B1 | 12/2012 |
| EP | 2538266 A1 | 12/2012 |
| EP | 2563275 A1 | 3/2013 |
| EP | 2597113 A1 | 5/2013 |
| EP | 2598936 A1 | 6/2013 |
| EP | 2077292 B1 | 8/2013 |
| EP | 2625216 A1 | 8/2013 |
| EP | 2625217 A1 | 8/2013 |
| EP | 2625218 A1 | 8/2013 |
| EP | 2652532 A1 | 10/2013 |
| EP | 1830898 B1 | 3/2014 |
| EP | 3160404 | 5/2014 |
| EP | 2766750 A1 | 8/2014 |
| EP | 2452212 B1 | 3/2015 |
| EP | 2934383 A1 | 10/2015 |
| EP | 2200536 B1 | 1/2016 |
| EP | 2976042 A1 | 1/2016 |
| EP | 3185818 | 3/2016 |
| EP | 2129331 B1 | 4/2016 |
| EP | 3003217 A1 | 4/2016 |
| EP | 3025678 A1 | 6/2016 |
| EP | 2259750 B1 | 7/2016 |
| EP | 2934383 A4 | 7/2016 |
| EP | 3062741 A1 | 9/2016 |
| EP | 3072476 A1 | 9/2016 |
| EP | 1999188 B1 | 11/2016 |
| EP | 2685935 B1 | 11/2016 |
| EP | 2094193 | 1/2017 |
| EP | 2683287 | 2/2017 |
| EP | 3062742 | 2/2017 |
| EP | 3157466 | 4/2017 |
| EP | 3160404 | 5/2017 |
| EP | 3160683 | 5/2017 |
| EP | 3049023 | 6/2017 |
| EP | 3174500 | 6/2017 |
| EP | 3181094 | 6/2017 |
| EP | 2539351 | 7/2017 |
| ES | 2283058 T3 | 10/2007 |
| FR | 2653325 A1 | 4/1991 |
| JP | 59-501897 | 11/1984 |
| JP | 01-223970 | 9/1989 |
| JP | 2006-518222 | 8/2006 |
| JP | 2007-506516 | 3/2007 |
| JP | 2007-517616 | 7/2007 |
| JP | 2010-517639 | 5/2010 |
| JP | 2012-532685 | 12/2012 |
| JP | 2016-534816 | 11/2016 |
| WO | 9007545 A2 | 7/1990 |
| WO | 9007575 A1 | 7/1990 |
| WO | 9516475 A1 | 6/1995 |
| WO | 9611235 A1 | 4/1996 |
| WO | 9620919 A1 | 7/1996 |
| WO | 9631791 A1 | 10/1996 |
| WO | 9636890 A1 | 11/1996 |
| WO | 9749740 A1 | 12/1997 |
| WO | 9917684 A1 | 4/1999 |
| WO | 9929818 A1 | 6/1999 |
| WO | 9957581 A1 | 11/1999 |
| WO | 9960428 A1 | 11/1999 |
| WO | 9963366 A1 | 12/1999 |
| WO | 2000004078 A1 | 1/2000 |
| WO | 2000026980 A1 | 6/2000 |
| WO | 2000071613 A1 | 11/2000 |
| WO | 2001008607 A1 | 2/2001 |
| WO | 2001030512 A2 | 5/2001 |
| WO | 2001034067 A1 | 5/2001 |
| WO | 2001071392 A1 | 9/2001 |
| WO | 2002047583 A1 | 6/2002 |
| WO | 2002094331 A1 | 11/2002 |
| WO | 2003009014 A1 | 1/2003 |
| WO | 2003066707 A1 | 8/2003 |
| WO | 2003097711 A1 | 11/2003 |
| WO | 2004010905 A2 | 2/2004 |
| WO | 2004046768 A2 | 6/2004 |
| WO | 2004052242 A1 | 6/2004 |
| WO | 2004053536 A2 | 6/2004 |
| WO | 2004054471 A2 | 7/2004 |
| WO | 2004058318 A1 | 7/2004 |
| WO | 2004072689 A2 | 8/2004 |
| WO | 2005023331 A2 | 3/2005 |
| WO | 2005065734 A1 | 7/2005 |
| WO | 2006047383 A2 | 5/2006 |
| WO | 2006103674 A2 | 10/2006 |
| WO | 2006126095 A2 | 11/2006 |
| WO | 2007005778 A2 | 1/2007 |

(56) References Cited

FOREIGN PATENT DOCUMENTS

| | | |
|---|---|---|
| WO | 2007047529 A2 | 4/2007 |
| WO | 2007047530 A2 | 4/2007 |
| WO | 2007050394 A2 | 5/2007 |
| WO | 2007064594 A2 | 6/2007 |
| WO | 2008005644 A1 | 1/2008 |
| WO | 2008005652 A1 | 1/2008 |
| WO | 2008005752 A2 | 1/2008 |
| WO | 2008024766 A2 | 2/2008 |
| WO | 2008039655 A2 | 4/2008 |
| WO | 2008076729 A1 | 6/2008 |
| WO | 2008077040 A2 | 6/2008 |
| WO | 2008082957 A2 | 7/2008 |
| WO | 2008094876 A1 | 8/2008 |
| WO | 2008103798 A2 | 8/2008 |
| WO | 2008107882 A2 | 9/2008 |
| WO | 2008116132 A2 | 9/2008 |
| WO | 2008151088 A2 | 12/2008 |
| WO | 2009002703 A2 | 12/2008 |
| WO | WO2009002789 | 12/2008 |
| WO | 2009015161 A2 | 1/2009 |
| WO | 2009015226 A2 | 1/2009 |
| WO | 2009015234 A2 | 1/2009 |
| WO | 2009015240 A2 | 1/2009 |
| WO | 2009085755 A1 | 7/2009 |
| WO | 2009085756 A1 | 7/2009 |
| WO | 2009127844 A2 | 10/2009 |
| WO | 2010056686 A1 | 5/2010 |
| WO | 2010056687 A2 | 5/2010 |
| WO | 2010081093 A2 | 7/2010 |
| WO | 2010093823 A2 | 8/2010 |
| WO | 2011005937 A2 | 1/2011 |
| WO | 2011026068 A2 | 3/2011 |
| WO | 2011071790 A1 | 6/2011 |
| WO | 2011075377 A1 | 6/2011 |
| WO | 2011106435 A2 | 9/2011 |
| WO | 2012006616 A2 | 1/2012 |
| WO | 2012015639 A1 | 2/2012 |
| WO | 2012047961 A1 | 4/2012 |
| WO | 2012047964 A1 | 4/2012 |
| WO | 2012047969 A1 | 4/2012 |
| WO | 2012082704 A1 | 6/2012 |
| WO | 2012129407 A2 | 9/2012 |
| WO | WO2012129419 | 9/2012 |
| WO | 2013055746 A1 | 4/2013 |
| WO | WO2013059195 | 4/2013 |
| WO | 2013070924 A1 | 5/2013 |
| WO | 2013158942 A1 | 10/2013 |
| WO | 2013166068 A1 | 11/2013 |
| WO | WO2014029383 | 2/2014 |
| WO | 2014093751 A2 | 6/2014 |
| WO | 2014093764 A1 | 6/2014 |
| WO | 2014095690 A1 | 6/2014 |
| WO | 2014099630 A1 | 6/2014 |
| WO | 2014143926 A1 | 9/2014 |
| WO | 2014149462 A1 | 9/2014 |
| WO | 2014152017 A1 | 9/2014 |
| WO | 2015038620 A2 | 3/2015 |
| WO | 2015048279 A1 | 4/2015 |
| WO | 2015066502 A1 | 5/2015 |
| WO | 2015148673 A1 | 10/2015 |
| WO | 2016018932 A1 | 2/2016 |
| WO | WO2016018932 | 2/2016 |
| WO | 2016033217 A1 | 3/2016 |
| WO | 2016038470 A2 | 3/2016 |
| WO | 2016061233 A1 | 4/2016 |
| WO | 2016122805 A1 | 8/2016 |
| WO | WO2016133558 | 8/2016 |
| WO | 2016140708 A1 | 9/2016 |
| WO | 2016195095 A1 | 12/2016 |
| WO | 2016201351 A1 | 12/2016 |
| WO | 2017079449 | 5/2017 |
| WO | 2017079733 | 5/2017 |
| WO | WO2017087358 | 5/2017 |
| WO | 2017208230 | 12/2017 |
| WO | 2017223544 | 12/2017 |
| WO | WO2017221198 | 12/2017 |
| WO | 2018119408 | 6/2018 |
| WO | WO2018222579 | 12/2018 |
| WO | WO2018227014 | 12/2018 |
| WO | WO202219456 | 10/2020 |
| WO | WO2021007535 | 1/2021 |

OTHER PUBLICATIONS

Final Office Action dated Dec. 21, 2017 for U.S. Appl. No. 14/860,162, filed Sep. 21, 2015.
Final Office Action dated Mar. 3, 2016 for U.S. Appl. No. 14/181,145 for Argento, C. et al., filed Feb. 14, 2014.
International search Report and Written Opinion received for PCT Application No. PCT/US2014/026817, filed Aug. 28, 2014, Applicant: Shifamed Holdings, LLC, dated Aug. 28, 2014, 29 pages.
International Search Report and Written Opinion received for PCT Application No. PCT/US2015/046998, filed Aug. 26, 2015, Applicant: Shifamed Holdings, LLC, dated Nov. 30, 2015, 13 pages.
Klank, et al. CO2-laser micromachining and back-end processing for rapid production of PMMA-based microfluidic systems. Lab Chip, 2002, 2, 242-246.
Non-Final Office Action dated Apr. 13, 2017 for U.S. Appl. No. 14/860,162 for Salahieh, A. et al., filed Sep. 21, 2015.
Non-Final Office Action dated Aug. 17, 2015 for U.S. Appl. No. 14/181,145 for Argento, C. et al., filed Feb. 14, 2014.
Non-Final Office Action dated Jan. 12, 2018 for U.S. Appl. No. 14/836,646 for Salahieh, A. et al., filed Aug. 26, 2015.
Notice of Allowance dated Jul. 7, 2016 for U.S. Appl. No. 14/181,145 for Argento, C. et al., filed Feb. 14, 2014.
Restriction Requirement dated Jul. 17, 2017 for U.S. Appl. No. 14/836,646 for Salahieh, A. et al., filed Aug. 26, 2015.
Restriction Requirement dated Mar. 5, 2015 for U.S. Appl. No. 14/181,145 for Argento, C. et al., filed Feb. 14, 2014.
Tsao, et al. Bonding of thermoplastic polymer microfluidics. Microfluid Nanofuild (2009) 6:1-16.
Umbrecht, et al. Solvent assisted bonding of polymethylmethacrylate: characterization using the response surface methodology. pp. 1325-1328.
International Search Report and Written Opinion for PCT Application No. PCT/US2017/068226, filed Dec. 22, 2017, Applicant: Shifamed Holdings, LLC, dated Apr. 17, 2018, 15 pages.
Liang et al., "Bionic intraocular lens with variable focus and integrated structure," Optical Engineering 2015, vol. 54, No. 10, Article No. 105106, Internal pp. 1-7.
English translation of first Chinese Office Action issued for Patent Application No. 201580057973.1; dated Apr. 20, 2018, Applicant: Shifamed Holdings, LLC, 6 pages.
English translation of Japanese Office Action issued for Patent Application No. 2016-504315; dated Jan. 16, 2018, Applicant: Shifamed Holdings, LLC, 5 pages.
International Search Report and Written Opinion for PCT Application No. PCT/US2018/036548, filed Jun. 7, 2018, Applicant: Shifamed Holdings, LLC, dated Jun. 7, 2018, 8 pages.
Non-Final Office Action dated Jun. 6, 2018 for U.S. Appl. No. 14/860,162, Applicant: Shifamed Holdings, LLC, filed Sep. 21, 2015, 26 pages.
Notice of Allowance dated Jul. 23, 2018 for U.S. Appl. No. 14/836,646, Applicant: Shifamed Holdings, LLC, filed Aug. 26, 2015, 9 pages.
Non-Final Office Action dated Aug. 2, 2018 for U.S. Appl. No. 15/345,278, Applicant: Shifamed Holdings, LLC, filed Nov. 7, 2016, 36 pages.
Non-Final Office Action dated Aug. 15, 2018 for U.S. Appl. No. 15/890,631, Applicant: Shifamed Holdings, LLC, filed Feb. 7, 2018, 8 pages.
European Extended Search Report dated Mar. 12, 2018 for European Patent Application No. 15836820.9, Applicant: Shifamed Holding, LLC, filing date: Aug. 26, 2015, 21 pages.
Supplementary European Search Report dated Nov. 15, 2016 for European Patent Application No. 14769563.9, Applicant: Shifamed Holding, LLC, filing date: Mar. 13, 2014, 9 pages.
Notice of Allowance dated Sep. 26, 2017 for Canadian Patent

(56) References Cited

OTHER PUBLICATIONS

Application No. 2,959,354, Applicant: Shifamed Holdings, LLC, filed Aug. 26, 2015, 1 page.
English translation of First Chinese Office Action dated Sep. 10, 2020 for Chinese Patent Application No. 201780087361.6, Applicant: Shifamed Holdings, LLC, filing date: Dec. 23, 2017, 19 pages.
International Search Report and Written Opinion for PCT Application No. PCT/US2020/029131, filed Apr. 21, 2020, Applicant: Shifamed Holdings, LLC, dated Sep. 21, 2020, 15 pages.
International Search Report and Written Opinion for PCT Application No. PCT/US2020/041644, filed Jul. 10, 2020, Applicant: Shifamed Holdings, LLC, dated Oct. 27, 2020, 11 pages.
European Extended Search Report mailed Jan. 27, 2021 for European Patent Application No. 18809676.2, Applicant: Shifamed Holdings, LLC, filing date: May 29, 2018, 8 pages.

\* cited by examiner

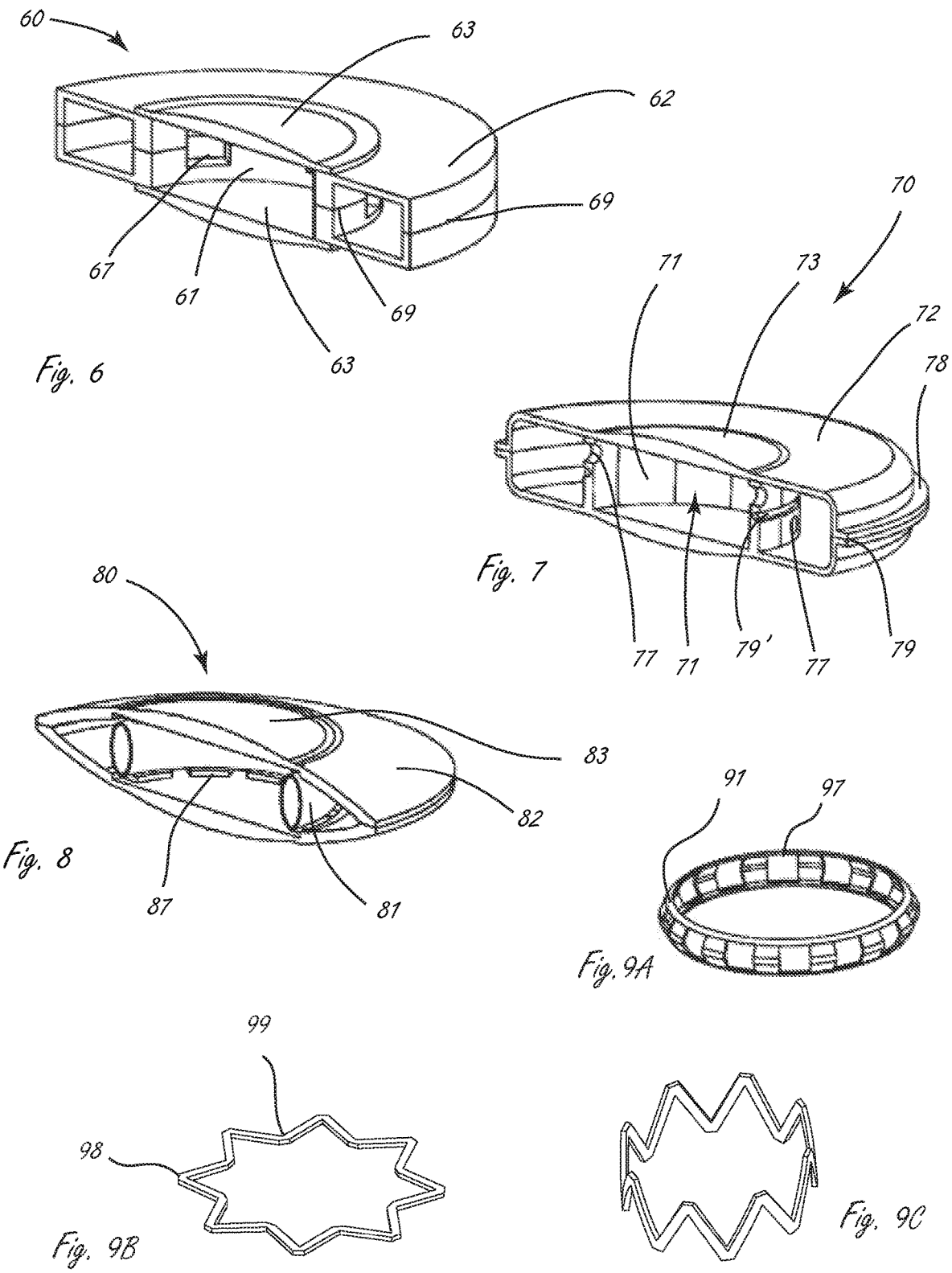

MULTI-PIECE ACCOMMODATING INTRAOCULAR LENS

CROSS-REFERENCE TO RELATED APPLICATION(S)

This application is a 35 U.S.C. § 371 U.S. National Phase application of International Patent Application No. PCT/US2016/061977, filed Nov. 15, 2016, entitled "MULTI-PIECE ACCOMMODATING INTRAOCULAR LENS," which claims priority to U.S. Provisional Application No. 62/257,087, filed on Nov. 18, 2015, entitled "MULTI-PIECE ACCOMMODATING IOL," Provisional Application No. 62/300,695, filed on Feb. 26, 2016, entitled "MULTI-PIECE ACCOMMODATING IOL,", U.S. Provisional Application No. 62/331,407, filed on May 3, 2016, entitled "AIOL DELIVERY DEVICE,", U.S. Provisional Application No. 62/331,946, filed on May 4, 2016, entitled "MULTI-PIECE ACCOMMODATING IOL,"; U.S. Provisional Application No. 62/334,998, filed on May 11, 2016, entitled "AIOL DELIVERY DEVICE,", U.S. Provisional Application No. 62/344,691, filed on Jun. 2, 2016, entitled "MULTI-PIECE ACCOMMODATING IOL,", and U.S. Provisional Application No. 62/362,896, filed on Jul. 15, 2016, entitled "MULTI-PIECE ACCOMMODATING IOL,", the contents of which are hereby incorporated by reference in their entireties.

BACKGROUND

The present disclosure relates to medical devices and methods. In particular, the present disclosure relates to accommodating intraocular lenses (hereinafter "AIOLs").

Cataracts can affect a large percentage of the worldwide adult population with clouding of the native crystalline lens and resulting loss of vision. Patients with cataracts can be treated by native lens removal and surgical implantation of a synthetic intraocular lens (IOL).

Worldwide, there are millions of IOL implantation procedures performed annually. In the US, there are 3.5 million cataract procedures performed, while worldwide there are over 20 million annual procedures performed.

Although IOL implantation can be effective at restoring vision, the prior IOLs provide less than ideal results in at least some instances. Many prior IOLs are not able to change focus as a natural lens would (known as accommodation). Also, the eyes receiving prior IOLs can have at least some refractive error after implantation, such that glasses can be helpful with distance vision. Although prior IOLs can be effective in providing good far vision, patients in many cases need to wear glasses for intermediate and near vision. Although prior multi-focal IOLs that address this drawback have been proposed, the prior multi-focal IOLs can be less than ideal. Although multi-focal IOLs generally perform well for reading and distance vision, in at least some instances prior multi-focal IOLs may cause significant glare, halos, and visual artifacts in at least some instances.

Although accommodating IOLs (AIOLs) have been proposed to provide accommodative optical power in response to the distance at which a patient views an object, the prior AIOLs can be less than ideal in at least some respects. For example, prior AIOLs can provide less than ideal amounts of accommodation after implantation, and may provide less than ideal refractive correction of the eye. Also, the amount of accommodation of the prior AIOLs can decrease after implantation in at least some instances. At least some of the prior AIOLs can be somewhat larger than would be ideal when inserted through an incision of the eye, and may require the incision to be somewhat larger than would be ideal. Also, work in relation to embodiments suggests that at least some of the prior AIOLs can be somewhat less stable when placed in the eye than would be ideal in at least some instances.

Improved implantable intraocular lenses that accommodate with the natural focusing response of the eye that overcome at least some of the above deficiencies would be desirable. Ideally, such improved AIOLs would provide increased amounts of accommodation when implanted, provide refractive stability, introduce few if any perceptible visual artifacts, and allow the optical power of the eye to change from far vision to near vision in response to the distance of the object viewed by the patient.

SUMMARY

Embodiments of the present disclosure provide improved AIOL methods and apparatus. In many embodiments, the AIOL comprises an inner fluid reservoir and an outer fluid reservoir disposed continuously about the inner fluid reservoir. The inner region of the AIOL, including the inner fluid reservoir, provides optical power. The outer fluid reservoir may comprise a bellows region fluidically coupled to the lens capsule. The AIOL provides optical power accommodation in one or more ways. A compliant fold region of the bellows region can allow the profile of the inner region of the AIOL to deflect when the eye accommodates for near vision. The bellows region allows fluid to transfer between the inner fluid chamber and the outer fluid reservoir to provide optical power changes when the eye accommodates. At the periphery of the inner fluid chamber, a plurality of protrusions such as posts or bumps may provide a predetermined amount of separation between the first and second lens components and may define one or more fluid channels between the inner fluid chamber and the outer fluid reservoir. While the bellows can be configured in many ways, in many embodiments, the bellows extend continuously and circumferentially around an optical axis of the lens, with one or more folds of opposing sides of the bellows extending toward each other in a direction similar to the optical axis. The folds of the bellows may extend continuously and circumferentially substantially around the optical axis, and can extend three hundred and sixty (360) degrees around the optical axis, for example.

Aspects of the present disclosure provide an accommodating intraocular lens for placement within a lens capsule of a subject. The accommodating intraocular lens may comprise a first component having a first lens region and a first bellows region, and a second component having a second lens region and a second bellows region, the second component coupled to the first component. A fluid chamber can be formed between the first lens region and the second lens region. A fluid reservoir can be formed between the first bellows region and the second bellows region, in which the fluid reservoir is in fluid communication with the fluid chamber to transfer fluid between the fluid chamber and the fluid reservoir in response to shape changes of the lens capsule to provide optical power changes to the accommodating intraocular lens.

In many embodiments, the first lens component is glued to the second lens component at a joint. Bumps can be located on an inner surface of one or more of the first component or the second lens component to provide a gap between the first component and the second component. The first lens component can be glued to the second lens component at a joint extending circumferentially around the first lens component and the second lens component.

The first bellows region can extend continuously circumferentially around the first lens region and the second bellows region can extends continuously circumferentially around the second lens region.

The first bellows region may comprise one or more folds extending continuously circumferentially around an optical axis of the first lens region and the second bellows region may comprise one or more folds extending continuously circumferentially around an optical axis of the second lens region.

The first bellows region may comprise a first one or more folds extending inwardly and continuously circumferentially around the first lens region and the second bellows region may comprise a second one or more folds extending inwardly and continuously circumferentially around the second lens region, the first one or more folds and the second one or more folds extending toward each other.

The first component may comprise a first annularly-shaped stiff coupling structure extending circumferentially between the first lens region and the first bellows region to inhibit radial movement of the first lens region with radial movement of the first bellows region. The second component may comprise a second annularly-shaped stiff coupling structure extending circumferentially between the second lens region and the second bellows region to inhibit radial movement of the second lens region with radial movement of the second bellows region. The first annularly-shaped structure may comprise a first radial thickness greater than a first thickness of the first bellows region and the second annularly-shaped structure may comprise a second radial thickness greater than a second thickness of the second bellows region.

The first lens region may comprise an anterior lens region and the second lens region may comprise a posterior lens component. The first lens region may comprise a first planar member and the second lens region may comprise a second planar member. One or more of the first and second components may comprise a shell, such as a non-planar shell. One of the first or second components may comprise a planar member and the other of the first or second components may comprise a plano-convex member shaped to provide an optical power.

The fluid within the fluid chamber may shape the fluid chamber so as to provide an optical power. Optical power changes to the accommodating intraocular lens may comprise a change to the optical power provided by the shape of the fluid within the fluid chamber. The change to the optical power provided by the shape of the fluid within the fluid chamber may comprise a change to a shape of the fluid chamber. Optical power changes to the accommodating intraocular lens may comprise a change to a separation distance between the first lens region and the second lens region.

Protrusions peripheral to edges of the first and second lens regions and radially inward from the bellows region may overlap and may be bonded with one another.

The fluid reservoir may comprise a compliant fold region between inner and outer bellows. The compliant region may be thinner than the inner and outer bellows. The lens chamber may be deflectable in response to deflection of the compliant fold region of the fluid reservoir. The compliant region may be thinner than inner and outer bellows portions located radially inward and radially outward to the fold region, respectively.

The accommodating intraocular lens may further comprise a plurality of protrusions, such as one or more of bumps and posts, coupled to one or more of the first and second lens components and the first and second lens components may be separated from one another. The plurality of protrusions may be disposed along outer edges of the inner portions of the first and second lens components. The plurality of protrusions may define a plurality of fluid channels between the fluid chamber and the fluid reservoir, each fluid channel being defined between two adjacent protrusions such as posts or bumps.

The protrusions can be located between the bellows region and the lens region to connect the first lens component to the second lens component. The protrusions can be located on one or more stiff coupling structures of one or more of the first lens component and the second lens component to provide the gap between the first component and the second component and define a plurality of channels extending around the protrusions and between the chamber and the reservoir to fluidically couple the reservoir to the chamber.

In many embodiments, the fluid reservoir comprises a compliant fold region between inner and outer bellows regions, the compliant region being thinner than the inner and outer bellows.

In many embodiments, a plurality of protrusions is coupled to the first or second components and separates the first and second lens components from one another. The plurality of protrusions can be disposed between the bellows regions and the lens regions, and plurality of protrusions can define a plurality of fluid channels between the fluid chamber and the fluid reservoir, in which each of the plurality of fluid channels is defined between two adjacent posts.

One or more of the first or second lens components may comprise a polymeric material such as a PMMA copolymer. The polymeric material may be water permeable. The polymeric material may be hydrophilic. Water within the lens capsule of the subject may transfer into or out of one or more of the fluid chamber or fluid reservoir through the polymeric material to achieve an osmotic equilibrium when the accommodating intraocular lens is placed within the lens capsule. The polymeric material may be non-permeable to compounds having a molecular weight of greater than 40 kDa, for example. The accommodating intraocular lens may further comprise the fluid within the fluid chamber. The fluid may comprise one or more of a solution, an oil, a silicone oil, a solution of dextran, a solution of high molecular weight dextran, or a solution of another high molecular weight compound.

In many embodiments, the fluid reservoir comprises a continuous baffle structure disposed about a periphery of the fluid chamber. The continuous structure may comprise one or more of an annular, elliptical, or rotationally symmetric shape.

In many embodiments, the first and second components are sufficiently flexible to be folded into a reduced cross-section delivery configuration. The reduced cross-section delivery configuration may comprise one or more of folds or rolls of the intraocular lens around a delivery axis transverse to an optical axis of the accommodating intraocular lens. The accommodating intraocular lens may comprise a delivery tube or aperture, and the reduced cross-section delivery configuration may comprise the intraocular lens advanced into the delivery tube or aperture.

In many embodiments, the fluid reservoir comprises a haptic structure to engage the lens capsule.

In many embodiments, the fluid within the fluid chamber has an index of refraction greater than an index of refraction of an aqueous humor of the eye of about 1.336.

In many embodiments, the first or second lens regions provide no optical power.

In many embodiments, the fluid within the fluid chamber provides optical power.

In many embodiments, the first and second lens components are bonded to one another.

In many embodiments, the first and second lens components comprise a polymer material, and the first and second lens components are bonded with a prepolymer of polymer material.

In many embodiments one or more of the first lens component or the second lens component have been directly fabricated, such as by three-dimensional (3D) printing.

In many embodiments, the first lens component and the second lens component have been directly fabricated together and comprise a single piece.

In many embodiments, the first lens component and the second lens component have been molded separately and bonded together.

In many embodiments, the first lens component and the second lens component have been lathed separately and bonded together.

In many embodiments, the first lens component and the second lens component are bonded together at protrusions extending between the first component and the second component.

In many embodiments, the first lens component comprises a first fabricated part and the second lens component comprises a second fabricated part.

Aspects of the present disclosure provide a method of providing accommodation to an eye of a subject. A varying compressive force from the lens capsule may be received by an outer fluid reservoir of the accommodating intraocular lens placed within a lens capsule of the eye. A fluid may be urged between an inner fluid chamber of the accommodating intraocular lens and a bellows region of the outer fluid reservoir in response to received varying compressive force, the bellows regions comprising a fold extending continuously circumferentially around an optical axis of the intraocular lens. One or more of a size or shape of the inner fluid chamber may be changed in response to the fluid urged into or out of the inner fluid chamber to change an optical power of the accommodating intraocular lens.

In many embodiments, inner and outer bellows regions are in fluid communication with one another and the inner fluid chamber. One or more of the bellows region can be annular, elliptical, or rotationally symmetric in shape.

In many embodiments, the fluid reservoir comprises a haptic structure to engage the lens capsule.

In many embodiments, changing one or more of the size or shape of the inner fluid chamber comprises changing a separation distance between portions of first and second lens regions.

In many embodiments, changing one or more of the size or shape of the inner fluid chamber comprises changing a radius of curvature of one or more of first or second lens regions which define the inner fluid chamber.

In many embodiments, the accommodating intraocular lens comprises first and second lens regions which define the inner fluid chamber, and one or more of the first or second lens regions comprises a plano-convex member shaped to provide a minimum optical power to the accommodating intraocular lens.

In many embodiments, the inner fluid chamber comprises a fluid therein and the inner fluid chamber provides a shape to the fluid such that the fluid provides the optical power to the accommodating intraocular lens.

In many embodiments, increasing the varying compressive force urges fluid into the inner fluid chamber.

Embodiments of the present disclosure provide improved AIOL methods and apparatus. In many embodiments, the AIOL comprises an optical structure comprising a stiff member and a deflectable member coupled to a haptic structure, such that the stiff member and the deflectable member substantially define a chamber of the AIOL. The chamber of the AIOL comprises a fluid having an index of refraction greater than the aqueous humor of the eye, such that the deflectable member defines a convexly curved surface of the chamber fluid in order to provide a fluid lens having adjustable optical power. The deflectable member and stiff member may be coupled to the haptic structure in order to deflect the profile of the deflectable member and fluid lens to a convexly curved profile when the eye accommodates for near vision. In many embodiments, the haptic structure rotates relative to the stiff member in order to provide an inward force to the deflectable member when the capsular bag moves inward and the eye accommodates for near vision. The haptic structure may comprise a curved capsular bag engaging portion shaped to receive the capsular bag. The haptic structure can be coupled to the stiff member at a first region, and to the deflectable member at a second region between the first region and the bag engaging portion, such that the forces of the capsular bag can be increased with leverage, in order to provide increased amounts of inward force to the outer portions of the deformable member. In many embodiments, the deflectable member is configured to amplify inward movement of the outer portion of the deflectable member, such that an inner portion of the deflectable member moves away from the stiff member more than the outer portion of the peripheral portion moves inward when the eye accommodates. This amplification of movement of the inner portion of the deflectable member and corresponding increase in curvature coupled with leverage of the capsular forces of the haptic can provide improved accommodation of the AIOL.

In many embodiments, the arrangement of the stiff member, the deflectable member and the rotating haptic is capable of deflecting the deflectable member with inward forces, such that decreased amounts of fluid can be used with the AIOL and incision size may be decreased. In many embodiments, the arrangement of the stiff member, the deflectable member, and the rotating haptic is capable of deflecting the deflectable member with inward forces without fluidic pressure of the lens chamber, and in at least some embodiments the arrangement can provide a convex curvature to the deflectable member with negative pressure of the chamber. In many embodiments, the chamber at least partially defined with the deflectable member and the stiff member receives fluid from an outer portion of the chamber beneath the outer potion of the deflectable member, such that the amount of fluid contained in the AIOL and insertion profile can be decreased.

The optical structure can be configured in one or more of many ways to provide increased amounts of accommodation. The deflectable member may comprise an inner optically corrective portion and an outer extension portion to provide a curvature transition between the inner optical portion and the haptic. The oppositely curved outer portion can decrease the diameter of the optically corrective portion in order to concentrate the optical power change within the inner portion. When the eye accommodates for near vision, the inner portion comprises an outer convexly curved surface to provide optical power with the fluid of the chamber, and the extension comprises a concave curvature, which is opposite the curvature of the inner portion. The oppositely curved extension can decrease the size of the inner optical zone, such that the optical power and curvature provided with the deflectable member are increased. The outer surface of the inner portion of the deflectable member can be convexly curved, concavely curved, or substantially flat for far vision and comprises a more positive curvature when deflected to the accommodation configuration for near vision. The outer surface of the outer portion can be concavely curved or substantially flat for far vision and comprises a more negative curvature when deflected to the accommodation configuration for near vision. The inner surfaces of the inner and outer portions of the deflectable member can be similarly curved. In many embodiments, the deflectable member comprises a substantially uniform thickness. Alternatively, the outer portion may comprise a decreased thickness relative to the inner portion, and may comprise an outer surface having a concave profile to facilitate convex curvature of the inner portion when inward force is applied with the haptic. The outer portion can be sized such that at least a portion of the outer portion is covered with the pupil in order to inhibit aberrations when the inner portion comprises the convex curvature and the outer portion comprises the concave curvature.

In many embodiments the stiff member comprises a lens such as a plano-convex lens having an optical power configured to treat far vision of the patient. When the eye accommodates, the deflectable portion provides additional optical power for near vision. In many embodiments, the diameter of the lens of the stiff member corresponds to the diameter of the inner portion of the deflectable member, such that the diameter of the lens of the stiff member is sized smaller than the outer portion of the deflectable member, in order to decrease the thickness profile of the AIOL when inserted into the eye.

In many embodiments, an accommodating IOL comprises a first lens component and a second lens component each composed of a polymer, and adhesive comprising the polymer. Alternatively, or in combination, the first component can be affixed to the second component with mechanical coupling such as interlocking joints, threads, mounts or fasteners. In many embodiments, the polymer can be hydrated and swells with hydration, such that the first component, the second component, and the adhesive swell together (e.g., at the same or substantially similar rate). By swelling together, stresses among the first component, the second component, and the adhesive can be inhibited substantially. Also, the hydratable adhesive allows the first and second components to be machined in a stiff less than fully hydrated configuration prior to adhering of the components together. The stiff configuration may comprise a less than fully hydrated polymer, such as a substantially dry polymer. The components can be bonded together in the substantially stiff configuration to facilitate handling during manufacturing, and subsequently hydrated such that the components bonded by the adhesive comprise a soft hydrated configuration for insertion into the eye. The adhesive comprising the polymer can bond the first and second lens components together with chemical bonds similar to the polymer material itself in order to provide increased strength.

In an aspect, an intraocular lens comprises an optical structure having an optical power and a haptic structure. The optical structure comprises a deflectable member, a stiff member, and a fluidic chamber defined at least partially by the stiff member and the deflectable member. The haptic structure has an outer structure to engage a capsule of the eye and an inner structure coupled to the deflectable member to increase curvature of the deflectable member when the haptic structure rotates relative to the stiff member.

In many embodiments, the deflectable member is deflected from a first profile to a second profile, in which the second profile is more curved than the first profile. The chamber comprises a fluid having an index of refraction greater than 1.33, such that the chamber comprises a first amount of optical power with the deflectable member in the first configuration and a second amount of optical power with the deflectable member in the second configuration, and the second amount of optical power is greater than the first amount.

In many embodiments, the deflectable structure comprises an inner optical portion and an outer extension portion. The stiff member, the haptic, and the deflectable member can be arranged such that the inner optical portion moves away from the stiff member with increased curvature and the outer extension moves toward the stiff member with an opposite curvature in order to provide increased optical power. Movement of the inner optical portion away from the stiff member and movement of the outer extension portion toward the stiff member can transmit fluid from an outer portion of the chamber beneath the outer extension portion to an inner portion of the chamber beneath the inner optical portion, such that fluid transfer is decreased and a volume of fluid of the AIOL can be decreased.

In many embodiments, the rotation occurs about an axis extending through a perimeter of the haptic structure. When the intraocular lens is placed in the eye, the perimeter of the haptic structure may be on a plane transverse to the optical axis of the eye, for example.

In many embodiments, the haptic structure may comprise a cantilevered haptic structure anchored on an inner end to the stiff member at a first location. The haptic may comprise a length extending a distance from the inner end to an outer end. The haptic structure may comprise a thickness, and the length may be greater than the thickness. The deflectable member may be coupled to the haptic structure at a second location separated from the first location by a separation distance. The length may be greater than the separation distance in order to separate an inner optical portion the deflectable member from the stiff member when the haptic structure rotates relative to the stiff member.

In many embodiments, the stiff member comprises one or more convexly curved optical surfaces. The stiff member may extend to a thin portion located near an outer edge of the stiff member. The thin portion may define an anchoring pivot structure around which the haptic structure rotates in order to urge the deflectable member inward with radial force when the haptic rotates in response to pressure of the structure of the eye.

In many embodiments, the deflectable member comprises an inner optical portion and an outer resilient extension coupled to the haptic structure. The resilient extension may comprise a thickness less than a thickness of the inner region of the deflectable member. The resilient extension may comprise a curvature opposite a curvature of the inner optical region when the resilient extension has separated the inner optical portion of the deflectable member away from the stiff member. The inner edge of the haptic structure may exert a radial force on the resilient extension of the deformable member to one or more of decrease a diameter of the inner optical region, or to deflect curvature of the resilient extension and the inner optical region in opposite directions relative to one another in order to urge the inner optical region away from the stiff member with spherical deflection of the inner optical region and urge the extension toward the stiff member in response to rotation of the haptic structure relative to the stiff member.

In many embodiments, a decrease in diameter of the deflectable member comprises a transition from a first diameter to a second diameter less than the first diameter in response to rotation of the haptic structure, wherein the decrease in diameter spherically deflects the inner optical portion away from the stiff member and changes a shape of the fluid-filled chamber to a more convexly curved profile in order to increase the optical power of the optical structure.

In many embodiments, the convexly curved profile of the fluid-filled chamber comprises an increased volume in order to change the optical power of the optical structure. Fluid may be drawn into the chamber from a peripheral reservoir in response to the increased volume.

In many embodiments, the haptic structure moves a peripheral portion of the deflectable member radially inward a first distance in response to the radial force directed thereon and the inner region of the deformable member may be urged away from the stiff member a second distance greater than the first distance in response to the rotation of the haptic structure so as to provide amplification of the second movement relative to the first movement and shape the deflectable member with a spherical profile. The deflectable member may comprise a substantially uniform and constant thickness to inhibit distortion.

In another aspect of the disclosure, a method of providing accommodation to an eye of the patient comprises placing an intraocular lens within a lens capsule of the eye. The intraocular lens may have an optical structure and a haptic structure coupled to the optical structure at an outer region of the optical structure. The optical power of an optical structure of the intraocular lens may be changed by rotating the haptic structure at the outer region in response to an inward force of the lens capsule.

In many embodiments, the haptic structure is rotated about an axis extending through a perimeter of the haptic structure. When the intraocular lens is placed in the eye, the perimeter of the haptic structure may be on a plane transverse to the optical axis of the eye, for example. In many embodiments, the method may further include anteriorly translating the at least a portion of the optical structure relative to an outer edge of the haptic structure in response to the rotation of the haptic structure. The translation of the at least a portion of the optical structure may change an optical power of the eye.

In many embodiments, the at least a portion of the optical structure may comprise a deflectable profile member comprising an outer region coupled to the inner edge of the haptic structure, an inner region, and a pivoting region between the haptic structure and the inner region. The inner edge of the haptic structure may exert an inward force on the outer region of the deflectable member to one or more of: decrease a diameter thereof; or pivot the outer and inner regions relative to one another at the pivoting region to deflect the inner region away from the stiff member in response to the rotation of the haptic structure to change the haptic power. The decrease in diameter of the deflectable member and the pivoting of the outer and inner regions of the deflectable member relative to one another may change one or more of a shape or a volume of the fluid-filled chamber to change the optical power of the optical structure. The inner edge of the haptic may move a first distance relative to the inner edge in response to the radial force directed on the inner edge; and the inner region of the deflectable member may be deflected away from the stiff member a second distance greater than the first distance in response to the rotation of the haptic structure.

In another aspect of the disclosure, an intraocular lens is provided. The intraocular lens may comprise an optical structure having an optical power and comprising a deflectable member, a stiff member, and a fluid chamber defined at least partially between the deflectable member and the stiff member. The intraocular lens may comprise a haptic structure coupled to a peripheral region of the stiff member and comprising a first exterior element, a second exterior element, and a fluid reservoir defined at least partially between the first exterior element and the second exterior element. The fluid reservoir may be in fluid communication with the fluid chamber with one or more channels. The haptic structure may be configured to rotate at the peripheral region and the second exterior element may be configured to deflect inward toward the first exterior element to decrease a volume of the fluid reservoir in response to an inward force of a lens capsule in order to change the optical power. In many embodiments, the haptic structure is configured to rotate about an axis extending through a perimeter of the haptic structure. When the intraocular lens is placed in the eye, the perimeter of the haptic structure may be on a plane transverse to the optical axis of the eye, for example. In many embodiments, the second exterior element may have an outer region, an inner region, and a pivoting region between the outer region and the inner region. The outer and inner regions of the second exterior element may pivot relative to one another at the pivoting region to deflect the second exterior element toward the first exterior element. In many embodiments, a volume of the fluid chamber may increase in response to the decrease in the volume of the fluid reservoir to change the optical power. A shape of the fluid-filled chamber may change in response to the increase in the volume of the lens fluid chamber to change the optical power. The shape change of the fluid-filled chamber may comprise a deflection of an inner region of the deflectable member away from the stiff member and a decrease in a radius of curvature of the deflectable member. In many embodiments, an inner edge of the haptic structure may move a first distance in response to the rotation of the haptic structure and the inner region of the deflectable member may be deflected away from the stiff member a second distance greater than the first distance to change the optical power. The shape change of the fluid chamber may leave the geometry of the stiff member substantially undeflected.

In many embodiments, the deflectable member may comprise an outer region coupled to the inner edge of the haptic structure, an inner region, and a pivoting region between the outer and inner regions. The inner edge of the haptic structure may exert an inward force on the outer region of the deflectable member to one or more of: change a diameter thereof; or pivot the outer and inner regions relative to one another at the pivoting region to deflect the inner region away from the stiff member in response to the rotation of the haptic structure to change the optical power of the optical structure. The deflectable member and the stiff member may be supported with the haptic structure and may translate together in a first direction in response to the rotation of the outer end of the haptic structure in a second direction opposite the first direction. The deflectable member may be located on a posterior portion of the optical structure and the stiff member may be located on an anterior portion of the optical structure of the eye. The deflectable member may move posteriorly relative to the stiff member to increase curvature of the deflectable member when the haptic structure rotates in response to the inward force of the lens capsule. The haptic structure may translate the stiff member and the deflectable member anteriorly together such that the optical power of the eye is increased with each of the increased curvature of the deflectable member, deflection of the deflectable member posteriorly relative to the stiff member, and anterior translation of the stiff member and the deflectable member.

This aspect of the disclosure may also provide a method of providing accommodation to a patients eye, such as by providing and using the intraocular lens provided.

In another aspect of the disclosure, a method is provided for providing accommodation to an eye of the patient. The method may comprise placing an intraocular lens within a lens capsule of the eye. A haptic structure of the intraocular lens at a peripheral portion of an optical structure of the intraocular lens may be rotated in response to an inward force of the lens capsule. The rotation may occur about an axis extending through a perimeter of the haptic structure. A member of the optical structure may be deflected to a more curved profile in response to the rotation to change an optical power of the eye. A shape and a volume of a fluid chamber of the optical structure may be changed in response to the rotation to change the optical power. The shape and volume of the fluid chamber may be changed by deflection of one or more of an anterior or posterior member of the optical structure to increase a radius of curvature. The optical structure may be translated in an anterior direction relative to an outer edge of the haptic structure in response to the rotation to change the optical power. In many embodiments, the combination of such separation, deflection, and translation may combine to change the optical power.

In yet another aspect of the disclosure, a method of providing accommodation to an eye of the patient is provided. The method may comprise placing an intraocular lens within a lens capsule of the eye. The intraocular lens may comprise an optical structure and a haptic structure coupled to a peripheral region of the optical structure. An optical power of an optical structure of the intraocular lens may be changed be rotating a haptic structure of the intraocular lens at the peripheral region to decrease a volume of a fluid reservoir of the haptic structure in response to an inward force of the lens capsule. The rotation of the haptic structure of the intraocular lens may occur about an axis extending through a perimeter of the haptic structure. When the intraocular lens is placed in the eye, the perimeter of the haptic structure may be on a plane transverse to the optical axis of the eye, for example. The fluid reservoir of the haptic structure may be defined at least partially between first and second exterior members of the haptic structure. The volume of the fluid reservoir may be decreased by deflecting the second exterior member inward toward the first exterior member in response to the inward force. Changing the optical power of the optical structure may further comprise increasing a volume of a fluid chamber of an optical structure in response to the decrease in the volume of the fluid reservoir. Changing the optical power of the optical structure may further comprise changing a shape of the fluid-filled chamber in response to the increased volume of the fluid-filled chamber.

In many embodiments, changing the shape of the fluid-filled chamber comprises a deflection of an inner region of a deflectable member of the optical structure away from a stiff member and a decrease in a radius of curvature of the deflectable member toward the stiff member. The shape of the fluid-filled chamber may further be changed by translating the inner region and an outer region of the deflectable member away from the stiff member. An inner edge of the haptic structure may move a first distance in response to the rotating of the haptic structure. The inner region of the deflectable member may be deflected away from the stiff member a second distance greater than the first distance to change the optical power. The shape change of the fluid-filled chamber may leave the geometry of the stiff member substantially undeformed. The deflectable member of the optical structure may be located on a posterior portion of the optical structure and the stiff member may be located on an anterior portion of the optical structure when placed in the eye. Changing the optical power of the optical structure may comprise moving the deflectable member anteriorly relative to the stiff member to increase curvature of the deflectable member when the haptic structure rotates in response to the inward force of the lens capsule to increase the optical power of the eye. The stiff member and the deflectable member may be translated anteriorly together with the haptic structure to increase the optical power of the eye. The perimeter of the deflectable member may be separated away from the perimeter of the stiff member to increase the optical power of the eye. In many embodiments, such deflection, translation, and separation can be used in combination to increase the optical power of the eye.

In another aspect of the disclosure, an intraocular lens comprises an optical structure comprising a posterior member, an anterior member, and a fluid-filled chamber between the posterior and anterior members. The intraocular lens may include a haptic structure interlocking peripheral regions of the posterior and anterior members to inhibit leakage of a fluid into and out of the fluid-filled haptic chamber. In many embodiments, the interlocking regions may comprise a fluid tight seal to inhibit leakage of the fluid. The haptic structure may have a first side having one or more male members and a second side having one or more female members. The one or more male members may pass through the peripheral regions of the posterior and anterior members to be received by the one or more female members to interlock the peripheral regions. The peripheral regions of the posterior and anterior members may have one or more aperture through which the one or more members pass through. The peripheral regions of one or more of the posterior or anterior members may have one or more male members to be received by one or more female members of the haptic structure to interlock the peripheral regions. The interlocking of the peripheral regions of the posterior and anterior members by the haptic structure may be maintained as the intraocular lens is one or more of: deformed to change an optical power of the optical structure; or, folded or rolled into a delivery configuration.

In yet another aspect of the disclosure, an intraocular lens is provided. The intraocular lens comprises an optical structure comprising a posterior member, an anterior member, and a fluid-filled chamber between the posterior and anterior members providing an optical power. The intraocular lens may comprise a haptic structure coupled to the optical structure. One or more of a shape or volume of the fluid-filled chamber may be configured to change in response to a radial force exerted on the haptic structure. The change of one or more of the shape or volume of the fluid-filled chamber may change the optical power of the fluid-filled chamber while leaving optical powers provided by the posterior and anterior members substantially unchanged.

In another aspect of the disclosure, a method of providing accommodation to an eye of the patient is provided. The method may comprise placing an intraocular lens within a lens capsule of the eye. One or more of a shape or volume of a fluid-filled chamber of the intraocular lens may be changed to change an optical power of the fluid-filled chamber while leaving optical powers provided by the posterior and anterior members substantially unchanged.

In yet another aspect of the disclosure, an intraocular lens is provided. The intraocular lens may comprise an optical structure for placement in an eye.

In another aspect of the disclosure, a method is provided. The method may comprise placing an optical structure in an eye.

In many embodiments, the deflectable optical members as described herein have the advantage of deflecting while substantially maintaining a thickness of the optical member in order to inhibit optical aberrations when the member deflects.

An aspect of the disclosure provides an intraocular lens for implantation within a lens capsule of a patients eye. The intraocular lens may comprise an optical structure and a haptic structure. The optical structure may have a peripheral portion and may comprise a planar member, a piano-convex member coupled to the planar member at the peripheral portion, and a fluid optical element defined between the planar member and the piano-convex member. The fluid optical element may comprise a fluid having a refractive index similar to either or both the materials comprising the planar member and the piano-convex member. The haptic structure may couple the planar member and the piano-convex member at the peripheral portion of the optical structure. The haptic structure may comprise a fluid reservoir in fluid communication with the fluid optical element and a peripheral structure for interfacing to the lens capsule. Shape changes of the lens capsule may cause one or more of volume or shape changes to the fluid optical element in correspondence to deformations of the planar member to modify the optical power of the fluid optical element. For example, shape changes of the lens capsule may cause the haptic structure to exert a mechanical force on the planar member to deform the member and correspondingly modify the optical power of the fluid optical element. Such deformations of the planar member may in some cases cause no change to the optical power of the planar member, the piano-convex member, or both (i.e., the change in optical power may solely be provided by one or more of the shape or volume changes to the fluid optical element and optionally changes to the anterior-posterior position of the intraocular lens within the lens capsule.)

The haptic peripheral structure may be stiffly coupled to the substantially planar member of the optical structure such that a radially directed force on the haptic peripheral structure may deflect the substantially planar member away from the plano-convex member in order to modify the optical power of the fluid optical element. The planar member may be anchored to a structure along a circular peripheral portion of the planar member. Deflection of the planar member away from the piano-convex member may provide a spherical optical correction. The change in optical power of the fluid optical element may comprise a response to a transfer of fluid into or out of the fluid optical element from the fluid reservoir of the haptic structure.

A force imposed on the haptic fluid reservoir may deform the haptic fluid reservoir to modify the optical power of the fluid optical element. The force imposed on the haptic fluid reservoir may cause fluid to transfer into or out of the fluid optical element from the haptic fluid reservoir to reversibly deform the haptic fluid reservoir.

In many embodiments, volume changes to the fluid optical element are provided by a fluid of the haptic fluid reservoir. In many embodiments, fluid transfer into or out of the fluid optical element leaves the plano-convex member undeformed. The plano-convex member may comprise a stiff member and the planar member may comprise a deflectable member. In these embodiments, the fluid optical element may provide a majority of the optical power of the intraocular lens. Fluid within the fluid optical element and within the fluid reservoir of the haptic structure may have a refractive index of greater than or equal to 1.33.

The fluid within the fluid optical element and the fluid reservoir of the haptic structure may comprise oil such as a silicone oil or a solution such as a high molecular weight dextran. The fluid can be provided with a suitable index of refraction. The high molecular weight dextran configured with a suitable index of refraction greater than 1.33 and an osmolality similar to the aqueous humor of the eye. The high molecular weight dextran may have a mean molecular weight of at least 40 kDa, and the mean molecular weight can be within a range from about 40 kDa to about 2000 kDa, with intermediate ranges having upper and lower values defined with any of 40 kDa, 70 kDa, 100 kDa, 1000 kDa, or 2000 kDa. The high molecular weight dextran may comprise a distribution of molecular weights, and the distribution of molecular weights can be narrow or broad. As the index of refraction can be determined based on the weight of dextran per volume and the osmolality by the number of solute particles per volume, the mean molecular weight and amount of dextran can be used to configure the dextran solution with the appropriate index of refraction and osmolality.

In many embodiments, the haptic structure is configured to orient the intraocular lens in place within the lens capsule of the patients eye. In many embodiments, the haptic structure comprises an anterior haptic structure and a posterior haptic structure, and the anterior haptic structure and the posterior structure are coupled together to define the fluid reservoir therebetween. In many embodiments, the haptic structure comprises an annular structure coupled to the peripheral region of the optical structure. The haptic structure may comprise a plurality of tab structures coupled to and distributed over the peripheral portion of the optical structure.

The peripheral portion may comprise a plurality of apertures and the haptic structure may be coupled to the peripheral portion through the plurality of apertures. The plurality of apertures may be oriented substantially parallel to the optical axis of the intraocular lens. Alternatively, or in combination, the plurality of apertures may be oriented transverse to the optical axis of the intraocular lens. The haptic structure may comprise one or more posts or other structures for placement through the plurality of apertures of the peripheral portion of the optical structure to couple the haptic structure to the peripheral portion. Alternatively, or in combination, the optical structure may comprise posts for mating with structures such as apertures in the haptic structures.

The intraocular lens may be sufficiently flexible to be folded into a reduced cross-section delivery configuration. The reduced cross-section delivery configuration of the intraocular lens may be attained by folding or rolling the intraocular lens around a delivery axis normal to an optical axis of the lens. Alternatively, or in combination, the reduced cross-section delivery configuration of the intraocular lens may be attained by advancing the intraocular lens through a delivery tube or aperture.

In many embodiments, the planar member is posterior of the plano-convex member when the intraocular lens is placed in the lens capsule.

Another aspect of the disclosure provides a method of providing accommodation in an eye of a patient. First, an intraocular lens may be provided. The provided intraocular lens may comprise an optical structure having a peripheral portion and a haptic structure. The optical structure may comprise a planar member, a plano-convex member coupled to the planar member at the peripheral portion, and a fluid optical element defined between the planar and plano-convex members. The fluid optical element may comprise a fluid having a refractive index similar to either or both the materials comprising the between the planar and plano-convex members. The fluid optical element may have an optical power. The haptic structure may couple the planar and plano-convex members together at the peripheral portion of the optical structure. The haptic structure may comprise a fluid reservoir in fluid communication with the fluid optical element and a peripheral structure for interfacing to the lens capsule. Second, the intraocular lens may be folded into a reduced profile configuration. Third, the folded intraocular lens may be implanted into a lens capsule of the patients eye. The folded intraocular lens reverts into a working configuration from the reduced profile configuration when implanted into the lens capsule. Fourth, one or more of the optical structure or the haptic structure may be actuated to cause one or more of volume or shape changes to the fluid optical element in correspondence to deformations in the planar member to modify the optical power of the fluid optical element.

One or more of the optical or haptic structure may be actuated by radially directing a force on the haptic structure to deform the planar member to modify the optical power of the fluid optical element. The haptic peripheral structure may be stiffly coupled to the substantially planar member of the optical structure. The change in optical power of the fluid optical element may be accompanied by a transfer of fluid into or out of the fluid optical element from the fluid reservoir of the haptic structure. Transfer of fluid into or out of the fluid optical element from the haptic fluid chamber may deflect the planar member while leaving the plano-convex member undeflected. In alternative embodiments, transfer of fluid into or out of the fluid optical element from the haptic fluid chamber may deflect the planar member and optionally also the plano-convex member.

Actuating one or more of the optical structure and the haptic structure may be actuated by imposing a force on the haptic fluid reservoir to reversibly deform the haptic fluid reservoir to modify the optical power of the fluid optical element.

In many embodiments, the peripheral portion of the optical structure comprises a plurality of apertures and the haptic structure couples the posterior and anterior members together at the peripheral portion of the optical structure through the plurality of apertures. The haptic structure coupled to the plurality of apertures of the peripheral portion may maintain the substantially planar and plano-convex members coupled together as the intraocular lens is folded and during function or operation of the intraocular lens. The plurality of apertures may be oriented substantially parallel to the optical axis of the intraocular lens. The plurality of apertures may be oriented transverse to the optical axis of the intraocular lens. The haptic structure may comprise one or more posts for placement through the plurality of apertures to couple the haptic structure to the peripheral region. Alternatively, or in combination, the peripheral portion of the optical structure may have one or more apertures through which one or more posts of the haptic structure can pass through to couple the optical and haptic structures together.

The intraocular lens may be folded into the reduced profile configuration by folding or rolling the intraocular lens around a delivery axis normal to an optical axis of the lens. Alternatively, or in combination, the intraocular lens may be folded into the reduced profile configuration by advancing the intraocular lens through a delivery tube or aperture.

The folded intraocular lens may be implanted into the lens capsule by allowing the fluid within the lens fluid chamber to reach an osmotic equilibrium with fluid present in the lens capsule. One or more of the planar or plano-convex members may be water permeable to allow the osmotic equilibrium to be reached. In many embodiments, the porous posterior or anterior member is non-permeable to compounds having a molecular weight of greater than 40 kDa.

In many embodiments, one or more of the planar or plano-convex members has substantially no optical power.

In many embodiments, the planar member is posterior of the piano-convex member when the intraocular lens is placed in the lens capsule.

In another aspect, embodiments provide a method of manufacturing an accommodating intraocular lens. A first lens component comprising a polymer is provided. A second lens component comprising the polymer is provided. The first lens component is bonded to the second lens component with an adhesive. The adhesive may comprise a prepolymer of the polymer.

In many embodiments, the prepolymer is cured to bond the first lens component to the second lens component with the polymer extending between the first lens component and the second lens component.

In many embodiments, the first lens component and the second lens component each comprise a stiff configuration when the first lens component is bonded to the second lens component with the polymer extending between the first component and the second component.

In many embodiments, the first lens component is hydrated, the second lens component and the cured adhesive are hydrated to provide a hydrated, soft accommodating intraocular lens.

In many embodiments, hydrating the first lens component, the second lens component and the adhesive comprises fully hydrating the polymer of each of the components and the adhesive to an amount of hydration corresponding to an amount of hydration of the polymer when implanted.

In many embodiments, each of the first lens component, the second lens component and the cured adhesive each comprise a stiff configuration prior to hydration and soft configuration when hydrated and wherein each of the first lens component, the second lens component, and the cured adhesive expand a substantially similar amount from the first configuration to the second configuration in order to inhibit stress at interfaces between the adhesive and the first and second components.

Many embodiments further comprise providing the polymer material and shaping the first lens component and the second lens component from the polymer material.

In many embodiments, the first lens component and the second lens component are each turned on a lathe when stiff in order to shape the first lens component and the second lens component.

In many embodiments, the first lens component and the second lens component are molded.

In many embodiments, the prepolymer comprises one or more of a monomer, an oligomer, a partially cured monomer, particles, or nano-particles of the polymer.

In many embodiments, the first lens component comprises a disc shaped structure and the second component comprises a disc shaped structure and wherein the first component and the second components define a chamber with the disc shaped structures on opposite sides of the chamber when bonded together.

In many embodiments, one or more of the first component or the second component comprises a groove sized and shaped to receive the opposite component and wherein the adhesive is placed on the groove.

In many embodiments, one or more of the first component or the second component comprises an annular structure extending between the disc structure and the second disc structure in order to separate the first disc structure from the second disc structure and define a side wall of the chamber.

In another aspect, an accommodating intraocular lens comprises a first lens component, a second lens component, and an adhesive. The first lens component comprises a polymer material. The second lens component comprises the polymer material. A cured adhesive comprises the polymer between at least a portion of the first component and the second component in order to bond the first lens component to the second lens component and define a chamber.

In many embodiments, the chamber comprises an optical element.

Many embodiments further comprise a fluid within the chamber having an index of refraction greater than an index of refraction of an aqueous humor of an eye of about 1.336 and wherein one or more of the first component or the second component is configured to deform to increase an optical power of the accommodating intraocular lens.

Many embodiments further comprise one or more haptics to engage a wall of a capsular bag of the eye and increase curvature of one or more of the first lens component or the second lens component in response to the wall of the capsular bag contracting in order to increase optical power of the accommodating intraocular lens.

Many embodiments further comprise a fluid, the fluid comprising one or more of a solution, an oil, a silicone, oil, a solution of high molecular weight molecules, or high molecular weight dextran.

Many embodiments further comprise a seam comprising the adhesive, the seam extending circumferentially along the at least a portion of the first component and the second component.

In many embodiments, the first lens component comprises a first disc shaped structure and the second lens component comprises a second disc shaped structure on opposite sides of the chamber and wherein an annular structure extends between the first disc shaped structure and the second disc shaped structure to separate the first disc shaped structure from the second disc shaped structure and define the chamber.

In many embodiments, the intraocular lens comprises a stiff configuration prior to implantation and a soft configuration when implanted.

In many embodiments, the first lens component comprises a first disc shaped optical structure comprising one or more of a lens, a meniscus, a meniscus lens, or a flat plate, and wherein the second lens component comprises a second disc shaped optical structure comprising one or more of a lens, a meniscus, a meniscus lens, or a flat plate.

Yet another aspect of the disclosure provides an intraocular lens for implantation within a lens capsule of a patients eye. The intraocular lens may comprise an optical structure and a haptic structure. The optical structure may have a peripheral portion and may comprise a posterior member, an anterior member coupled to the posterior member at the peripheral portion, and a fluid optical element defined between the posterior and anterior members. The fluid optical element may comprise a fluid having a refractive index similar to either or both the materials comprising the posterior member and the anterior member. The fluid optical element may have an optical power. The haptic structure may couple the posterior and anterior members at the peripheral portion of the optical structure. The haptic structure may comprise a fluid reservoir in fluid communication with the fluid optical element and a peripheral structure for interfacing to the lens capsule. Shape changes of the lens capsule may cause one or more of volume or shape changes to the fluid optical element in correspondence to deformations in one or more of the posterior or anterior members to modify the optical power of the fluid optical element. One or more of the posterior member or the anterior member of the optical structure may be permeable to water such that water present in the lens capsule of the patients eye may be capable of transferring into or out of the fluid lens chamber there through to achieve an osmotic equilibrium with fluid present in the lens capsule when the intraocular lens is placed therein. The various features of the intraocular lens may further be configured in many ways in accordance with the many embodiments disclosed herein.

In another aspect of the disclosure, an implantable intraocular lens is provided. The intraocular lens may comprise an optical structure having a fluid chamber and a material within the fluid chamber. The material may comprise a less than fully hydrated state. A portion of the optical structure may be configured to provide water to the fluid chamber and inhibit leakage of the material from the fluid chamber in order to fully hydrate the material and expand the fluid chamber when placed in the eye.

In yet another aspect of the disclosure, a method of implanting an artificial lens within a lens capsule of a patients eye is provided. The method may comprise advancing an intraocular lens comprising a less than fully hydrated configuration through an incision of the eye. Water from the lens capsule may pass through at least a portion of the optical structure to fully hydrate the intraocular lens. In many embodiments, material within a fluid chamber of an optical structure of intraocular lens may be inhibited from leakage from the at least a portion of the optical structure while water from the lens capsule passes through to fully hydrate the material.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6 illustrates an AIOL wherein the haptic and support structures are integral and are configured as a toroid like structure, in accordance with many embodiments;

FIG. 7 illustrates a variation of the AIOL of FIG. 6 which incorporates features which help to reduce the delivery cross-section, in accordance with many embodiments;

FIG. 8 illustrates an AIOL which comprises an elastomeric support structure filled with a fluid capable of being hardened after delivery of the AIOL, in accordance with many embodiments;

FIGS. 9A, 9B, and 9C depict alternate collapsible lens support structures, in accordance with many embodiments;

FIGS. 10 through 14B illustrate alternate AIOL structures where an AIOL is inserted into and interfaced to the natural capsule such that the attachment zones seal a semi toroidal region of capsule, and where fluid transfer between the semi toroidal region and the interior of the AIOL causes an accommodation change in the AIOL, in accordance with many embodiments;

FIG. 10 depicts an AIOL with alternate haptic structures where a fluid chamber is formed by sealing the equatorial and posterior regions of the lens capsule incorporating one optical element, in accordance with many embodiments;

FIG. 11 depicts an AIOL with alternate haptic structures where a fluid chamber is formed by sealing the equatorial and posterior regions of the lens capsule incorporating two optical element, in accordance with many embodiments;

FIG. 12 depicts an AIOL with alternate haptic structures where a fluid chamber is formed by a thin membrane sealing the equatorial and posterior regions of the lens capsule incorporating two optical elements; in accordance with many embodiments;

FIG. 13 depicts an AIOL with alternate haptic structures where a fluid chamber is formed by a thin membrane and by sealing the equatorial and posterior regions of the lens capsule incorporating one optical element, in accordance with many embodiments;

FIG. 14B illustrates the installed AIOL of FIG. 14A, post-surgery, where the lens capsule has conformed to the installed device, in accordance with many embodiments;

DETAILED DESCRIPTION

Figure 1:
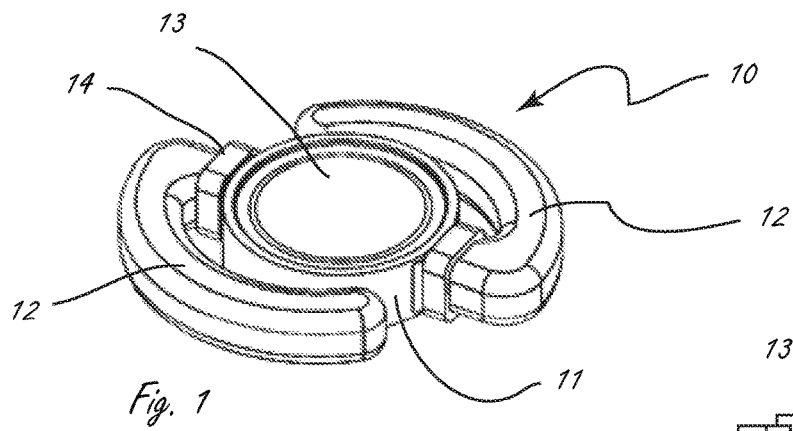
FIG. 1 illustrates an accommodating intraocular lens (AIOL) system, in accordance with many embodiments.

The accommodating intraocular lens (AIOL) as described herein can be used to provide improved vision, and can be combined with one or more of many known surgical procedures and apparatus, such as cataract surgery and intraocular lens inserters. The optical structures of the AIOL are well suited for use with commercially available IOL power calculations based on biometry of the eye, and can be used to provide improved vision. In many embodiments, a physician can insert the AIOL as described herein in a manner similar to prior non-accommodating IOLs such that the AIOLs as described herein can be readily used.

The structures of the AIOL as described herein can be combined in one or more of many ways to provide an improved accommodating IOL. In many embodiments, the AIOL comprises optical structures composed of a soft material, in which the optical structures are coupled to haptics, in order to provide optical power with natural forces of the lens capsule of the eye, as described herein, for example. In many embodiments, the deflectable member comprises sufficient radial strength such that a radially inward force to an outer portion of the deflectable member causes deflection of an inner portion of the deflectable member. The deflection may comprise a first order reversible buckling of the deflectable member, for example. In many embodiments, the deflectable member bends such that the inner portion comprises a convex curvature along the outer surface and the outer portion comprises an opposing convex curvature along the outer surface. The convex inner portion may comprise a disc shape and the outer concave portion may comprise an annular shape adjacent the disc shape. The arrangement of convex disc shape and concave annular shape can provide two inflection points across the diameter of the deflectable member, for example.

The radially extending deflectable member can be configured in one or more of many ways to provide radial strength in order deflect to at least the inner portion, for example with one or more of a modulus of elasticity, a thickness, or a diameter.

The deflectable member can be coupled to the haptics in one or more of many ways so as to deflect when urged radially inward by the haptics engaging the lens capsule. In many embodiments, the deflectable member comprises sufficient radial strength to induce shape changes of at least the inner portion when the outer portion of the deflectable member is urged radially inward, rotated, or combinations thereof. In many embodiments, the deflectable member is coupled to the lens capsule such that rotation of the haptics relative to the stiff member induces a radially inward movement and rotational deflection of an outer portion of the deflectable member. Alternatively, or in combination, the haptics can be arranged to slide radially and in relation to the stiff member in order to urge the deflectable member inward with radial force and deflect the inner portion of the deflectable member with radial strength of the outer portion. The deflectable member may comprise one or more structures on the outer portion to encourage deflection, such as a concave outer portion or thinner annular region to encourage concave deflection of the outer portion and convex deflection of the inner portion, for example.

The present disclosure relates to devices, methods, and systems associated with an improved accommodating intraocular lens (AIOL). Some embodiments will comprise a central optical structure comprised of two deformable lenses spaced apart along their optical axis, such as by a lens support structure concentric with the optical axis of the lenses. The volume bounded by the lenses and optionally the lens support structure may be filled with an ionic solution, such as saline, or non-ionic solutions such as dextran or silicone oil. The optical structure in turn may be bounded by one or more haptic structures, the haptic structures being either fluid-filled or of another embodiment, arranged in a plane normal to the optical axis of the lenses. The haptic structures can be in fluid communication with the fluid bounded by the optical structure. The transfer of fluid between the haptic structures and the fluid-filled optical structure can change the accommodating power of the lenses by deforming one or both of the lenses. Alternatively, or in combination, the haptic structures may directly exert mechanical forces on the lenses of the fluid-filled optical structure to cause deformation and change accommodating power. The improved accommodating intraocular lens system may additionally comprise any combination of the features described herein.

The lenses and some of the support structures described herein will typically be fabricated from a hydrophilic material that is optically clear when hydrated, swells on hydration by more than 10%, and accommodates strain levels of greater than 100% when hydrated. The material can be purchased as small disks and rods. For example, the hydrophilic material may comprise a copolymer of hydroxyethyl methacrylate (HEMA) and methyl methacrylate (MMA) such as C118, C121, or C126 produced by Contamac Ltd. of the UK. Additionally, any of the intraocular lens systems shown and described herein can be made from Benz IOL 25 UVX™ material manufactured by Benz Research and Development of Sarasota, Fla. These materials are also denoted as PMMA herein, and as used herein PMMA refers to a polymer comprising PMMA or a copolymer comprising PMMA, such as one or more of PMMA polymer (also referred to herein as "poly(methyl methacrylate)"), or a copolymer of HEMA and PMMA such as p(HEMA-co-MMA), for example. As used herein p(HEMA-co-MMA) refers to a copolymer of HEMA and PMMA and can also be referred to as p(HEMA-MMA).

The copolymer may comprise one or more of a block copolymer (PPPP-HHHH), alternating copolymer (PHPHPHPH), statistical or random copolymer (PHP-PHPHH), a star copolymer, a brush copolymer, or a graft copolymer, for example, where "P" identifies "MMA" and "H" identifies "HEMA", for example.

In some embodiments, components of a hydrogel AIOL may be fabricated by 3D printing, including but are not limited to any of the following common 3D printing processes: Stereolithography (SLA), Inkjet material jetting (IMJ), Digital Light Processing (DLP), Selective Laser Sintering (SLS), Fused Deposition Modeling, or Fused Filament Fabrication (FDM/FFF). Methods such as SLA, IMJ, and DLP may be particularly suited to the fabrication of AIOL elements comprised of hydrogels such as PMMA's and copolymers such as HEMA. In such embodiments, the starting material may be monomer or oligomer precursors, or combinations thereof, of the hydrogel polymer. One such polymer useful in the fabrication of AIOLs herein described may comprise pHEMA, in which the polymerization reaction can be photo initiated by a UV source of appropriate wavelength and duration. In some such embodiments, photo initiation may be further enhanced by the addition of a photoinitiator compound mixed with the monomers used for printing. Such photoinitiators can release additional free radicals on illumination thereby increasing the rate of the polymerization reactions. A selection of photoinitiators is listed below.

In some embodiments, the complete AIOL may be fabricated by the 3D printing process and the un-polymerized materials on the inside of the structure removed after completion of the build. Alternatively, or in combination, the un-polymerized materials within the lens structure may be treated such that reactive end groups are rendered nonreactive such that no further polymerization of that material may take place. In other embodiments, the AIOL structures may be fabricated as subcomponents for later assembly as described elsewhere herein for machined parts.

A used herein, a positive curvature of an outer surface encompasses a convex curvature and a negative curvature of an outer surface encompasses a concave curvature.

As used herein, like reference numerals refer to like structures. In many embodiments as described herein, the reference numerals comprise three or four digits in which the first one or two digits refer to the number of the drawing and the last two digits refer to like structures among figures having different numbers. For example, the reference numerals 2503 and 3303 refer to similar deflectable members of FIG. 25 and FIG. 33, respectively. A person of ordinary skill in the art will recognize that text describing a structure of one figure applies to similar structure of any other figure as provided herein.

In many embodiments, the deflectable member comprises an inner optical portion and an outer extension portion, so as to concentrate and amplify optical power within the inner optical portion. The inner optical portion can move away from the stiff member to comprise a convexly curved outer surface providing an increased optical power. In addition, the outer portion may be deflected toward the stiff member so as to comprise an opposite curvature and move toward the stiff member. The oppositely curved outer portion can decrease the diameter of the optically corrective portion in order to concentrate the optical power change within the inner portion. The optical power of the inner portion is related to the increased distance of the center of the inner portion from the stiff member, and the decreased distance from the outer extension portion to the stiff member. This combined effect of increased inner separation distance and decreased outer separation distance has a combined effect on increase optical power. Also, as the optical power of the lens can decrease approximately as the square of the diameter of the lens, the decreased diameter of the inner portion provided with the oppositely curved outer portion can further increase the optical power of the lens.

In some embodiments, the intraocular lens/lens system and/or other components defining the lens chamber or fluid optical element are filled with a water-based clear fluid with a refractive index higher than water, in order to increase the optical power of the system. The high refractive index of the lens chamber liquid may be caused by the presence of solutes. Such solutes often comprise large molecules incapable of crossing the chamber defining components. Examples of such large molecules include dextran, with exemplary molecular weights of <40 kD, <70 kD, <500 kD, and <1000 kD. Further examples of such solutes include sugar molecules. The solutes and water may compose a diluted solution having an osmolality. Such osmolality may cause the movement of water into or out of the chamber to achieve an osmotic equilibrium volume. Such volume can be adequate to produce the appropriate optical power in the system to the desired power for the patient.

Each of the accommodating IOLs as described herein comprises an anterior side and a posterior side. A nodal point of the lens is preferably located along an optical axis of the lens at a midpoint located along the optical axis approximately equidistant from the anterior and posterior surfaces of the optical structure of the lens. In many embodiments, the nodal point of the lens is located away from a plane extending between the peripheral haptic lever structures so as to define an anterior to posterior orientation of the lens. The anterior to posterior orientation of the lens can be reversed by a person of ordinary skill in the art based on the teachings disclosed herein.

The soft material of the optical structures of the AIOL can be shaped in one or more of many ways, and may comprise machined components, molded components, or combinations thereof, for example.

An improved accommodating intraocular lens can have a reduced delivery cross-section. The reduced delivery cross-section can be facilitated by an optical structure capable of translating from a delivery configuration to an operational configuration. The optical structure may have a small dimension along the optical axis in the delivery configuration and larger dimension along the optical axis in operational configuration. Also, a lens support structure can be configured to maintain the distance between the peripheries of the two lenses in the operational configuration and to allow fluid to pass between the haptic structures and the fluid volume bounded by the optical structure in either configuration.

The delivery cross-section may be attained by folding or rolling the AIOL around a delivery axis normal to the optical axis. The delivery cross-section may be measured as the largest dimension in the delivery configuration measured in a plane normal to the delivery axis. Delivery cross-sections attainable for the AIOLs disclosed herein may be less than 4.5 mm, and preferably less than 2.5 mm. In alternate embodiments, the delivery cross-section can be attained by forcing the AIOL through a tube or delivery aperture. Such a tube may be conical in cross-section such that the AIOL may be compressed as it progresses down the tube. The distal end may be sized to interface with an incision in the eye. Delivery may be facilitated by syringes or plungers.

The intraocular lens system may be comprised of at least two hydrophilic PMMA lenses where PMMA denotes a compound comprising one or more of poly(methyl methacrylate) (PMMA), poly(hydroxyethyl methacrylate) (PHEMA), (Hydroxyethyl)methacrylate (HEMA), or Methyl methacrylate (MMA), for example. The lens system may include other elements comprised of any or any combination of the following materials: NiTi, polyurethane, hydrophilic PMMA, photo-activated polymers, precursors to PMMA, Ethylene glycol dimethacrylate (EGDMA), silicones, silicone copolymers, among others.

One or more of the substantially planar member or the plano-convex member may comprise a polymeric material. The polymeric material may comprise a material, for example available from Contamac Ltd. of the UK or Vista Optics Ltd. of the UK. For example, the PMMA copolymer may be selected from the list comprising a Definitive 50 material, a Definitive 65 material, a Definitive 74 material, a Filcon V3 material, a Filcon V4 material, a Filcon V5 material, an Optimum Classic material, an Optimum Comfort material, an Optimum Extra material, an Optimum Extra 16 material, an Optimum Extra 18.25 mm material, an Optimum Extra 19 mm material, an Optimum Extra 21 mm material, an Optimum Extreme material, an F2 material, an F2 Low material, an F2 Mid material, an F2 High material, a Focon III 2 material, a Focon III 3 material, a Focon III 4 material, a Hybrid FS material, a Contaflex GM Advance material, a Contaflex GM Advance 49% material, a Contaflex GM Advance 58% material, a Filcon I 2 material, a Filcon II 2 material, a Contaflex GM3 49% material, a Contaflex GM3 58% material, a Contaflex material, a Contaflex 58% material, a Contaflex 67% material, a Contaflex 75% material, a Polymacon 38% material, a Hefilcon 45% material, a Methafilcon 55% material, a Filcon II material, a Filcon IV 2 material, an HI56 material, a PMMA material, a CI26 material, a CI26Y material, a CI18 material, and other variants available from Contamac Ltd. of the UK and a Vistaflex GL 59 material, a HEMA/GMA material, an Advantage+49 material, an Advantage+59 material, a Filcon I 1 material, a Filcon 12 material, a VSO nVP material, a nVP/MMA material, a VSO 60 material, a VSO 68 material, a VSO 75 material, a Filcon II 1 material, a Filcon II 2 material, a VSO pHEMA material, a pHEMA material, a HEMA material, a VSO 38 material, a VSO 42 material, a VSO 50 material, a Vistaflex 67 Clear UV material, a polysiloxy-acrylate material, an AddVALUE Silicone Acrylate material, an AddVALUE 18 material, an AddVALUE 35 material, a poly-fluoro-silicon-acrylate material, an AddVALUE Fluor Silicone Acrylate material, an AddVALUE 25 material, an AddVALUE 50 material, an AddVALUE 75 material, an AddVALUE 100 material, a Scleral Rigid Gas Permeable material, a hydrophobic intraocular lens material, a VOPhobic Clear Tg 16 material, a VOPhobic Yellow Tg 16 material, a hydrophilic intraocular lens material, a HEMA-MMA copolymer material, an IOSoft material, an IOSoft clear material, an IOSoft yellow material, a PMMA material, a Vistacryl CQ UV material, a Vistacryl XL blue material, a Vistacryl CQ material, and other variants available from Vista Optics Ltd. of the UK. Often, the polymeric material may be one or more of water permeable and hydrophilic. Water present in the lens capsule of the patients eye may transfer into or out of the fluid optical element through the polymeric material to achieve an osmotic equilibrium with fluid present in the lens capsule when the intraocular lens is placed therein. The polymeric material may be non-permeable to silicone oil. The polymeric material may be non-permeable to compounds having molecular weights of greater than 40 kDa.

In some embodiments, an AIOL is inserted into and interfaced to the natural capsule such that the interface zones create a seal which forms a semi toroidal region of capsule, where fluid transfer between the semi toroidal region and the interior of the AIOL causes an accommodation change in the AIOL. In such embodiments, fluid such as saline may be injected into the semi toroidal region.

In some embodiments, the optical structure is comprised of a material which is changed from a delivery configuration to an operation configuration after introduction into the capsule of the eye. One such material may comprise a photoactive polymer which in the delivery configuration is a liquid which is hardened by photo activation after introduction. Another such material may comprise a memory metal such as an NiTi alloy which in the delivery configuration has a thin dimension in a plane normal to the optical axis and after introduction is initiated to change to an operational configuration by heating via inductive coupling. In other embodiments, the NiTi may rely on its super elastic characteristics to shift from a delivery to an operational configuration.

The optical structure in some embodiments is mechanically more stable in the operational configuration than in the delivery configuration, and spontaneously changes from a delivery configuration to an operational configuration after introduction into the capsule of the eye. In such a configuration, the optical structure may be coaxed into a delivery configuration just prior to delivery or at manufacture. One such system may comprise a super elastic metal element which springs from the delivery configuration upon introduction of the device into the capsule.

In some embodiments, the lens support structure and one lens are machined or molded as a single structure and the second lens is affixed to the support structure by a bonding means. In many other embodiments, the AIOL is comprised of two halves, each incorporating a lens, which are bonded together to form the optical structure. Such embodiments may incorporate the haptic structures. In yet other embodiments, a second machining operation can be performed on the bonded structure. Alternate bonding means may include mechanical interfaces such as threading where the outer periphery of the lens is threaded and the inner surface of the support structure is threaded. In alternate embodiments, the interface can be a simple interference fit. In some embodiments, affixing comprises bonding the materials by treating the one or both of the separate bonding surfaces with a precursor monomer, then assembling the structure, applying a load across the bonding surfaces, and heating the assembly for a period of time. Such a process may facilitate crosslinking between the material comprising both parts. In some instances, the precursor monomer may be mixed with small particles of the polymer. Bonding agents may additionally include urethanes, silicones, epoxies, and acrylics among others.

In the devices of the present disclosure, the lenses may be compromised of a water and ion permeable material. In some embodiments, the AIOL can be allowed to self-fill after implantation, thereby minimizing the delivery cross-section.

In alternate embodiments, the AIOL is filled after implantation.

FIG. 1 illustrates an accommodating intraocular lens (AIOL) system or intraocular lens 10 comprised of a central lens support structure 11, two haptic structures 12, two deflectable lenses 13 of which only one is visible in FIG. 1, and two compression bands 14. The haptics structures 12 may comprise thin walled structures configured to deform under minimal loads and comprised of an elastomeric material. The internal volume of the AIOL 10 can be filled with a clear fluid such as saline of comparable osmolality to that of the fluids in the eye around the lens capsule. Alternatively, the AIOL 10 can be filled with fluids of high refractive index as described elsewhere herein. The lenses 13 are interfaced to the support structure 11 such that as fluid transfers from the haptics into the internal volume of the support structure the lenses are caused to deflect thereby changing their accommodative power.

Figure 2:
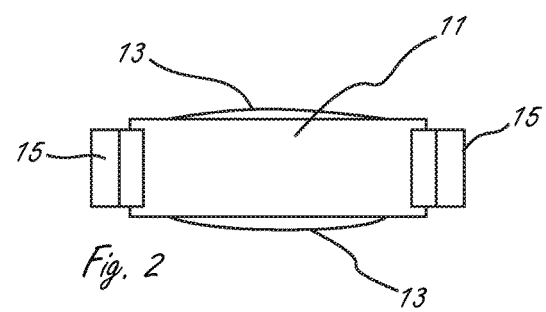
FIG. 2 illustrates a side view of a lens support structure and lens, in accordance with many embodiments.

A side view of the lens support structure 11 of FIG. 1 along with two lenses 13 is illustrated in FIG. 2. The lenses 13 may be of the same shape or may have differing shapes. Also visible in FIG. 2 are the haptic structure interface features 15 comprised in the lens support structure 11. The open end of the haptics structures 12 are fit over the haptic structure interface features 15 and are further affixed to the lens support structure interface feature 15 using compression bands 14. Additionally, in some embodiments, an adhesive or sealant such as silicone may be used. In alternate embodiments, a press fit may be used. In yet other embodiments, the haptics 12 may be molded onto a haptic interface. In one embodiment, the haptic 12 is molded onto a PMMA barb which is then bonded to the support structure 11. Said bonding may be by adhesive or facilitating cross linking between the barb and the support structure as described below herein. Materials for the haptic structures 12 and haptic structure interfacing may include any or any combination of silicone, PEBAX, urethane, copolymers of PMMA and silicone, and other elastomeric material. The distance between the periphery of the lenses 13 may be maintained by the support structure 11 while the center of the lenses are allowed to deflect as the fluid volume within the support structure 11 increases, thereby changing the accommodative power of the structure. In some embodiments, the haptic structures 12 may be fabricated from an extrusion.

Figure 3:
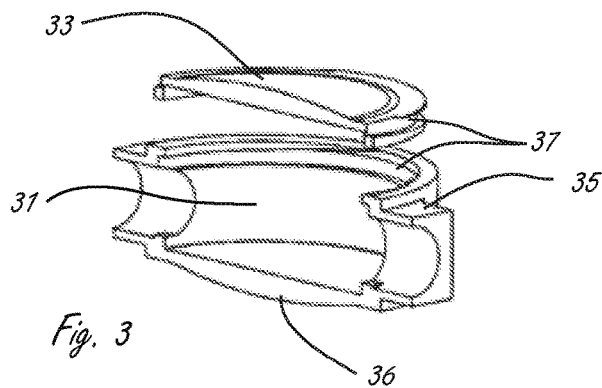
FIG. 3 illustrates a sectioned view of a lens support structure incorporating a lens interface using threads, in accordance with many embodiments.

FIG. 3 illustrates a lens support structure 31 in which one of the two lenses, first lens 36, is comprised in or integral with the support structure 31. The second lens, lens 33, in the embodiment of FIG. 3 is configured to interface to the support structure 31 via threads 37. A structure 35 extends outward to couple the lens body to haptics.

Figure 4:
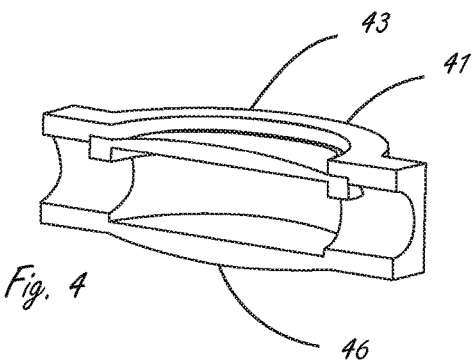
FIG. 4 illustrates a sectioned view of a lens support structure incorporating a lens interfaced using an interference fit, in accordance with many embodiments.

Another embodiment for a central support structure similar to that shown in FIG. 3 is illustrated in FIG. 4. In this embodiment, the second lens 43 is interfaced via an interference fit. In some embodiments, the interference fit may be further sealed through the use of a sealant or adhesive. The interference fit is further facilitated by the procedure used to assemble and rehydrate the components. One such procedure as implemented on the support structure 41 shown in FIG. 4 is as follows: the bottom of the support structure 41 comprising lens 46 is hydrated, lens 43 in the unhydrated condition is then fitted into the groove comprised in the support structure 41, the support structure 41 and lenses 43 and 46 are allowed to completely hydrate, and, if required, a sealant or adhesive is then applied. The use of interference fits can minimize the requirement and or amount of bonding agent.

Figure 5:
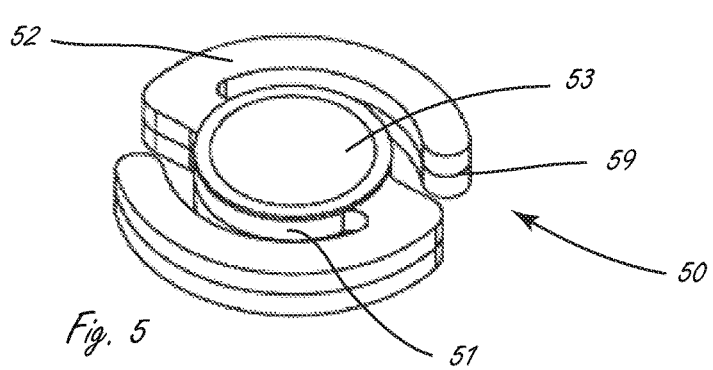
FIG. 5 illustrates an AIOL in which half of the support structure and haptic structures are comprised in an upper and lower half of the AIOL and all fabricated from the same material, in accordance with many embodiments.

FIG. 5 illustrates another embodiment of an AIOL 50 in which half of the support structure 51 and haptic structures 52 are comprised in an upper and lower half of the AIOL 50 and thereby all fabricated from the same material. The two halves are bonded together at seam 59 to form the complete haptic and support structure 51. Lens 53 may either be integral to the half structures or bonded to the support structure 51. In the manufacturing environment, allowing one lens to be aligned and bonded after the fabrication of the rest of the structure can provide an advantage in assuring the optical axis of the two lenses are precisely aligned.

In the embodiments shown in FIG. 1 and FIG. 2, the haptic structures 12 are configured in such a fashion that they may be folded out and away from the support structure 11 in a plane normal to the optical axis of the lenses. Such a configuration can facilitate a reduction in delivery cross-section for a fluid-filled device. In the embodiments shown in FIG. 6 and FIG. 7, the haptic structures are both integral to the lens support structure and attached continuously around the perimeter of the lens support structure.

FIG. 6 illustrates an embodiment of an AIOL 60 wherein the haptic structure 62 and support structure 61 are integral and are configured as a toroid-like structure; the inner radius of the toroid-like structure comprising the support structure 61. Fluid may be allowed to flow between the haptic structure 62 and the inner volume of the support structure 61 through openings 67. The AIOL 60 can be fabricated by bonding the two halves at seam 69. Lens 63 may be integral with the halves or bonded separately to the halves.

A variation on the embodiment of FIG. 6 is illustrated in FIG. 7. The embodiment of the AIOL 70 incorporates features which help to reduce the delivery cross-section. Half of the support structure may be comprised on each the upper and lower halves on the AIOL 70 and may be comprised of a series of structures 71 each separated by a space forming a castellated ring. Castellated structures can be meshed at assembly prior to bonding at seam 79. Spring ring 79' can fit in a grove and can lock the upper and lower halves of the structure relative to displacements along the optical axis. As shown in FIG. 7, lenses 73 can be integral to the half structures comprising the AIOL 70. In other embodiments, the lenses 73 may be separate and bonded at another time. In such embodiments, the support structure can be capable of greater deformation during delivery as the castellated elements can fold over a greater radius of curvature. AIOL 70 may also comprise feature 78, which can allow for a means of applying pressure directly across seam 79 during the bonding process. The surfaces which comprise the seam may additionally incorporate chamfers or fillets to direct the flow of bonding agents and minimize the likelihood of creating voids.

FIG. 8 represents an embodiment of an AIOL 80 which comprises an elastomeric support structure 81 filled with a fluid capable of being hardened after delivery of the AIOL. Such fluids may be optically cured and may comprise, for example, a UV curing silicone or epoxy, a pH cured fluid such as a collagen solution, or a heat cured fluid where the material comprises a suspension of particle capable of being inductively heated such as magnetite particles. Channels 87 can allow fluid to pass between the haptic and the central volume of the support structure.

In alternate embodiments, the support structure 81 of AIOL 80 may be replaced with a support structure 91 comprising channel structures 97 as indicated in the expanded configuration of AIOL 80 shown in FIG. 9A, or by support structure 98 as indicated in FIG. 9B and FIG. 9C, which may be comprised of a memory metal which can be flattened to comprise a flattened configuration 99 as indicated in FIG. 9B prior to assembly then heated by inductive coupling allowing it to take an operational configuration after delivery as indicated in FIG. 9C. Such a configuration may provide for a reduced cross-section.

Embodiments described herein also allow for sequencing the assembly and the use of long setting, heat, pressure, and/or optical initiated bonding materials to insure proper optical alignment of the lenses.

Bonding of a copolymer of HEMA and MMA may be facilitated by treating the bond surfaces with EGDMA or Triethylene glycol dimethacrylate (TEGDMA) and then subjecting the bonded surfaces to pressure and temperature. Treatments may include but are not limited to vapor treatment, wetting, wetting and allowing for evaporation, applying a mixture of EGDMA or TEGDMA and particles of a copolymer of hydroxyethyl methacrylate and methyl methacrylate. In one such procedure, 40 micron beads of a copolymer of HEMA and MMA can be mixed with EGDMA and used as a bonding agent. Such a bonding scheme can provide advantage in that there can be no or minimal seam and the mechanical properties of the bonded interface have the same mechanical properties as the structure.

Delivery procedures may vary and will depend on the embodiment of the device. In one delivery procedure for an AIOL, which is typically pre-filled with an operating fluid at manufacturing and ready for use, a device can be selected for size and base accommodating power to match the patient's requirements. The eye can be prepared according to standard procedures typical for the instillation of non-accommodating lenses, with the possible exception that the incision may be larger in some embodiments. The AIOL may be loaded into an injector and then injected into the prepared eye capsule. The AIOL can then be adjusted for position. In an alternate delivery procedure, the lens may be filled at the time of surgery. In such a procedure filling can comprise sizing the AIOL and or setting the base power of the AIOL. To accommodate such a procedure the device may incorporate a filling port which can be sealable by bonding prior to implantation or a port comprising a self-sealing material such as an elastomeric material.

In yet a further alternative, the AIOL may be filled after implant, thereby minimizing the delivery cross-section. In such embodiments, after implant, the device may be filled via a filling port as previously described. In alternate embodiments, the device may be initially be in a less than fully hydrated state and allowed to become fully hydrated after implantation, such as by self-filling with fluids naturally available in the eye. For example, the AIOL may comprise a material in a less than fully hydrated state, such as a fluid element within the AIOL, which can be fully hydrated by fluid from the eye and is inhibited from leaking from the AIOL during the hydration process. Such embodiments may rely on the permeability to water and small molecules of materials comprised in the AIOL. In such procedures, a device properly sized and filled with an appropriate operating fluid, typically a saline solution with an osmolality and ionic balance comparable to the fluids naturally occurring in the eye, can be prepared for implant by subjecting it to a hypertonic solution of large molecules such as a solution of super high molecular weight dextran. This pretreatment can draw fluid out of the AIOL prior to implant, thereby decreasing its delivery cross-section. The AIOL can then be implanted through an incision of the eye. After implant, the AIOL may scavenge fluid from the eye renewing its fluid and optic equilibrium. In some embodiments, the osmolality of the AIOL may further be adjusted by the incorporation of a molecule too large to diffuse through materials comprising the AIOL at the time of manufacture. In such systems, the equilibrium fill pressure for the AIOL may be adjusted or set on filling.

Figure 10:
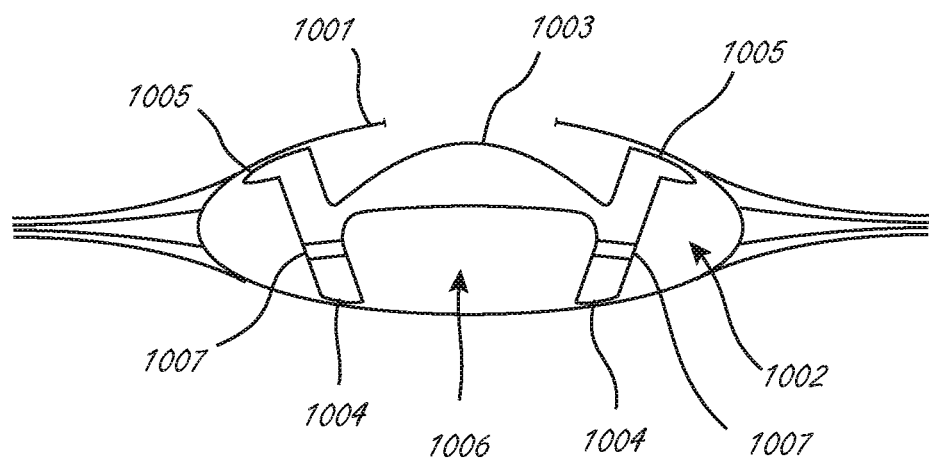

FIG. 10 depicts an AIOL with alternate haptic structures where a fluid chamber is formed by sealing the equatorial region of the capsule 1002 at the locations 1004 and 1005. Equatorial chamber 1002 can communicate with posterior chamber 1006 by holes 1007 in the structure of the AIOL. Movement of the ciliary body can cause the fluid of chamber 1002 to go in and out of chamber 1006, deflecting the single optical element 1003 and providing accommodation.

Chambers 1002 and 1006 can be filled either naturally, as with aqueous, or with other fluids such as saline; viscous cohesive fluids may be used to prevent leakage at contact locations 1004 and 1005.

Various methods to improve sealing may be employed at locations 1004 and 1005. Glue may be applied as a bond to the capsule; fibrogenic mechanisms may be induced; sharp protrusions may be provided at contact points to increase sealing against the capsule by indenting it; anterior contact location 1005 can be provided with means to capture the edge of the capsulorhexis 1001.

Optical element 1003 can be provided with means of hinging along the edges of the optical area to increase deflection and displacement, and therefore optical power.

The assembly could have external envelope with dimensions close to the crystalline, and therefore minimize the chance of capsular contraction.

There could be less sizing issues due the absence of conventional haptics, the only relevant capsular dimension may be its height.

The system may be indifferent to osmotic variations in the aqueous humor.

To reduce the chance of leakage, the as-cut dimensions could be in the accommodated geometry.

Figure 11:
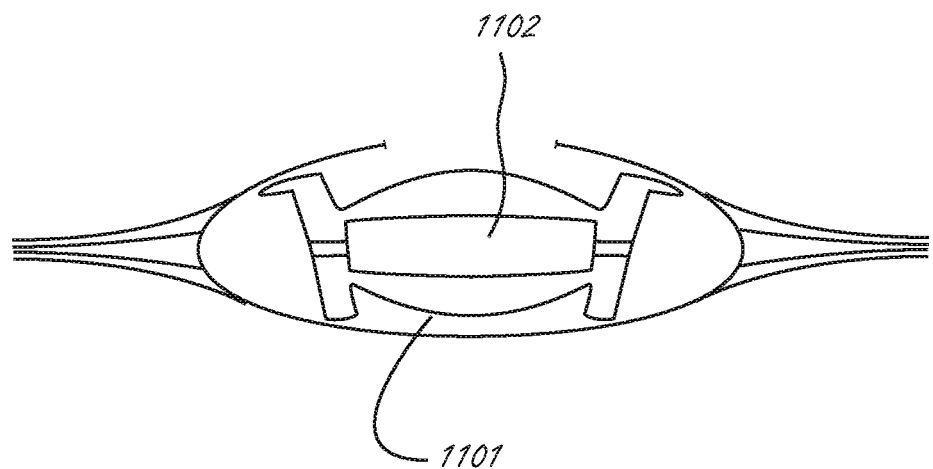

FIG. 11 shows an alternative AIOL, in accordance with many embodiments, which incorporates two optical element lens system with haptic structures configured to form a fluid chamber by sealing the equatorial and posterior regions of the lens capsule. Additional posterior optical element 1101 defines the fluid optical element or fluid chamber 1102 and may be provided for optical reasons (e.g., establishing fluid chamber 1102 and providing improved optical accommodation.)

Figure 12:
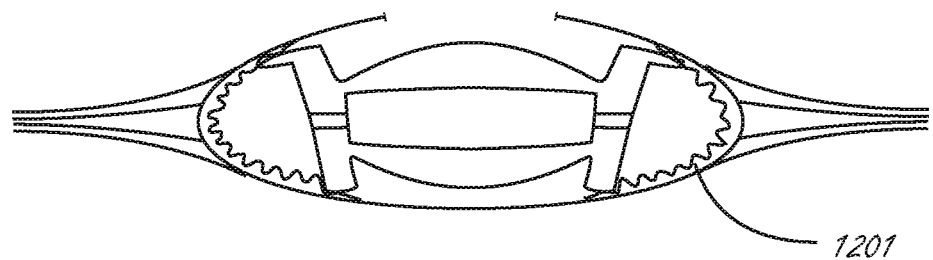

FIG. 12 shows an alternative AIOL, in accordance with many embodiments, which incorporates two optical elements with haptic structures configured to form a fluid chamber by sealing the equatorial and posterior regions of the lens capsule and where a thin membrane 1201 can be attached to the structure to contain the fluid.

Figure 13:
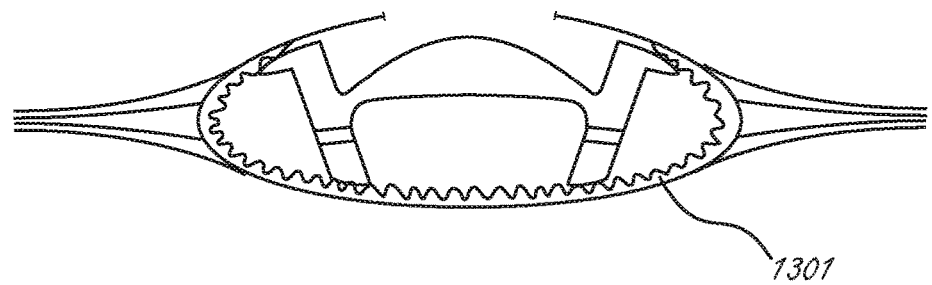

FIG. 13 shows an alternative AIOL, in accordance with many embodiments, which has haptic structures configured to form a fluid chamber by sealing the equatorial and posterior regions of the lens capsule incorporating one optical element and where a thin membrane 1301 can be attached to the structure to contain the fluid on a single optical element implementation.

Figure 14A:
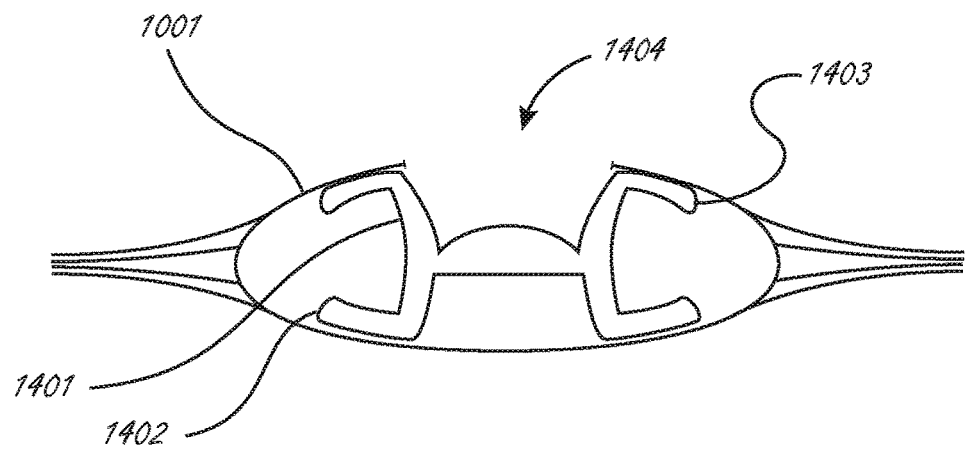
FIG. 14A illustrates an alternate embodiment after implantation of the AIOL, in accordance with many embodiments.
Figure 14B:
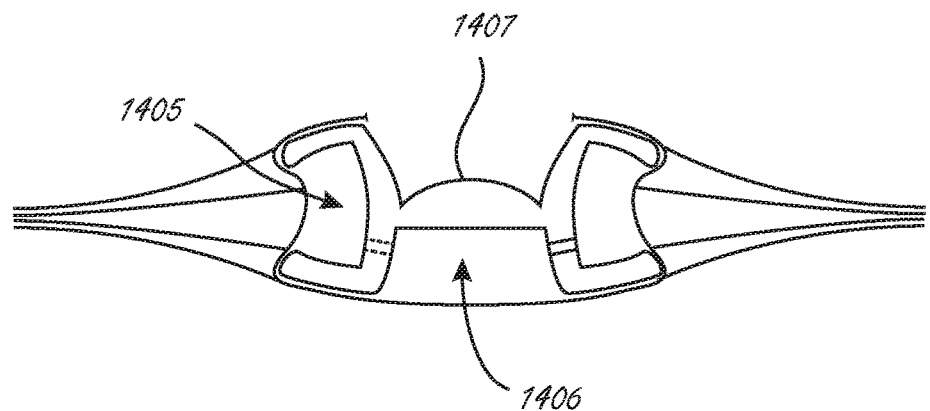

FIG. 14A and FIG. BIB illustrate an alternate AIOL, in accordance with many embodiments, where a single optical element lens support structure 1401 is uniformly open circumferentially along the perimeter of the device and where said lens support structure is not connected to fluid-filled or other conventional haptics. The AIOL device is shown in FIG. 14A and FIG. BIB as resting in lens capsule receiving structure or chamber 1405, and lens support structure 1401 is in contact with the posterior lens capsule at 1402 and is also in contact with the anterior lens capsule at 1403. The device can be positioned such that the anterior capsule opening 1404 and lens support structure 1401 may be aligned with the capsulorhexis 1001 in some fashion as to affect a working mechanical seal, described below. FIG. BIB illustrates the installed AIOL, post-surgery, where the lens capsule has conformed to the installed device and provides the seal required to create chambers 1405 and 1406 for the activation and relief of accommodation in the lens. The AIOL can be inserted into and interfaced to the natural capsule such that the attachment zones seal a semi toroidal region of capsule. Fluid transfer between the semi-toroidal region and the interior of the AIOL can causes an accommodation change in the AIOL, such as a deflection of lens surface 1407.

Figure 15:
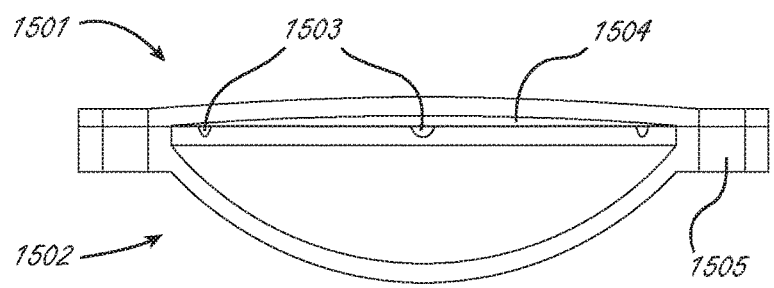
FIG. 15 depicts an optical structure comprising an anterior and posterior surface, in accordance with many embodiments.

FIGS. 15 through 23B illustrate alternate AIOL embodiment with an emphasis on their manufacture. FIG. 15 is an optical sub-assembly comprised of anterior lens element 1501 and posterior lens element 1502. Optical fluid channels 1503 allow fluid to enter fluid optical element or optical chamber 1504 and the sub-assembly is bonded to lens support structure 1601 at mounting hole 1505.

Figure 16A:
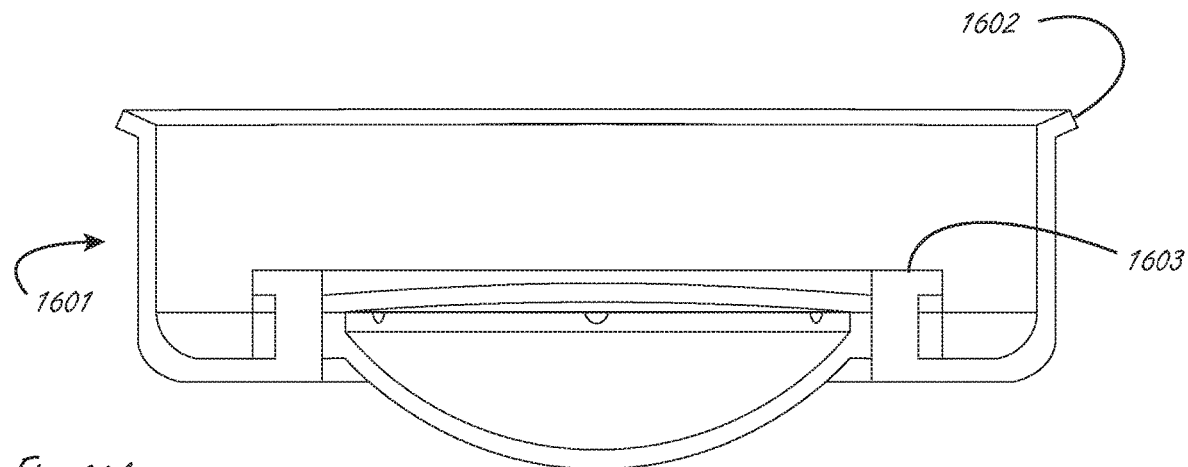
FIG. 16A illustrates a lens support structure joined to an optical structure prior to bonding, in accordance with many embodiments.
Figure 16B:
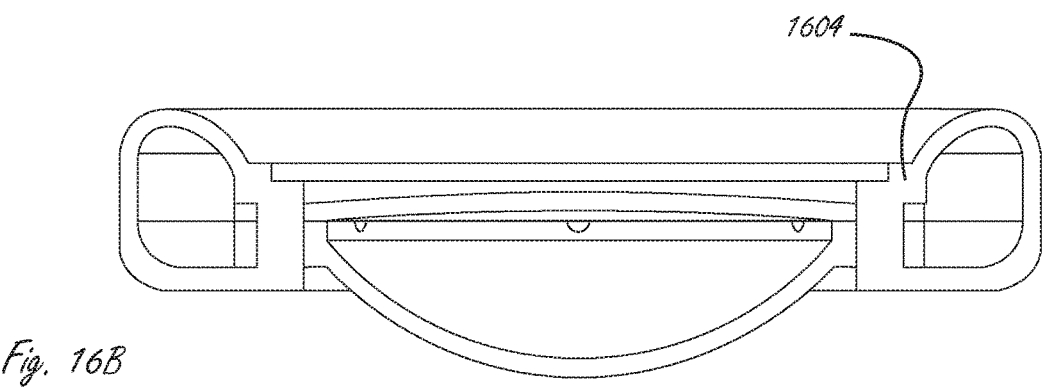
FIG. 16B represents a final AIOL with points bonded together providing a seal along the perimeter, in accordance with many embodiments.

FIG. 16A and FIG. 16B depict the optical sub-assembly of FIG. 15 insert molded into lens support structure 1601 and with contact points 1602 and 1603 bonded together at 1604 to complete the AIOL assembly.

Figure 17:
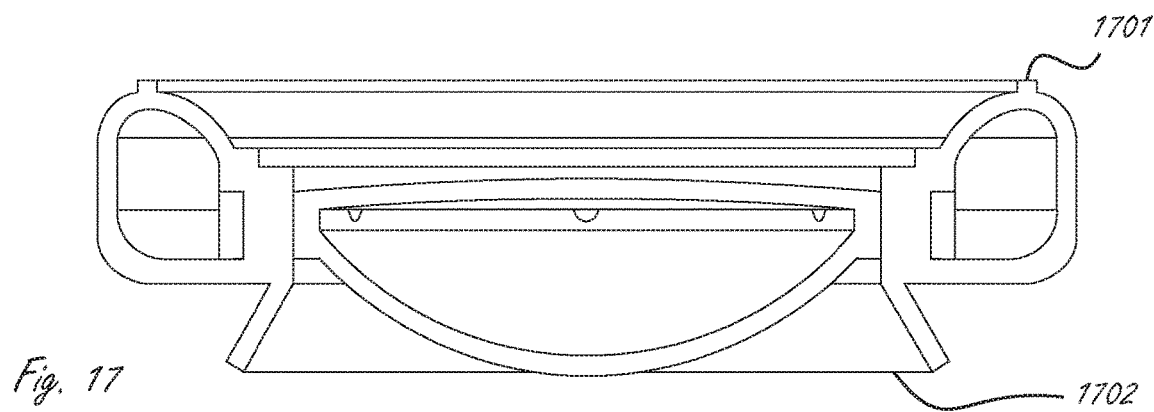
FIG. 17 represents the addition of alternate posterior opacification cell dam and anterior capsulorhexis support to the AIOL of FIG. 16B, in accordance with many embodiments.

FIG. 17 shows a modified embodiment of the aforementioned in FIG. 16 incorporating posterior opacification cell dam 1701 and capsulorhexis support flange 1702.

Figure 18:
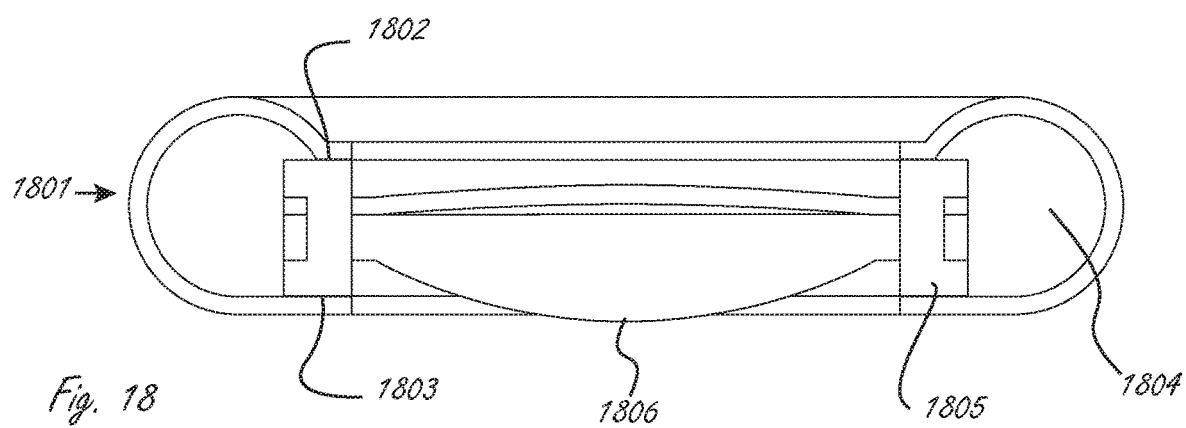
FIG. 18 depicts an alternate AIOL, in accordance with many embodiments.

FIG. 18 illustrates an AIOL final assembly where optical sub-assembly 1806 is insert molded into lens support structure 1805 with haptic structure 1801 bonded to 1805 at points 1802 and 1803, creating haptic fluid chamber 1804. This configuration may alternately incorporate a lens such as that illustrated in FIG. 19 where optical assembly 1901 is bonded, using either solvent or heat, to support structure 1903 at insert posts 1902. The lens system of FIG. 19 seals after assembly by hydrating the lens system until it swells approximately 10% thereby resulting in a fluid-tight force-fit.

Figure 19:
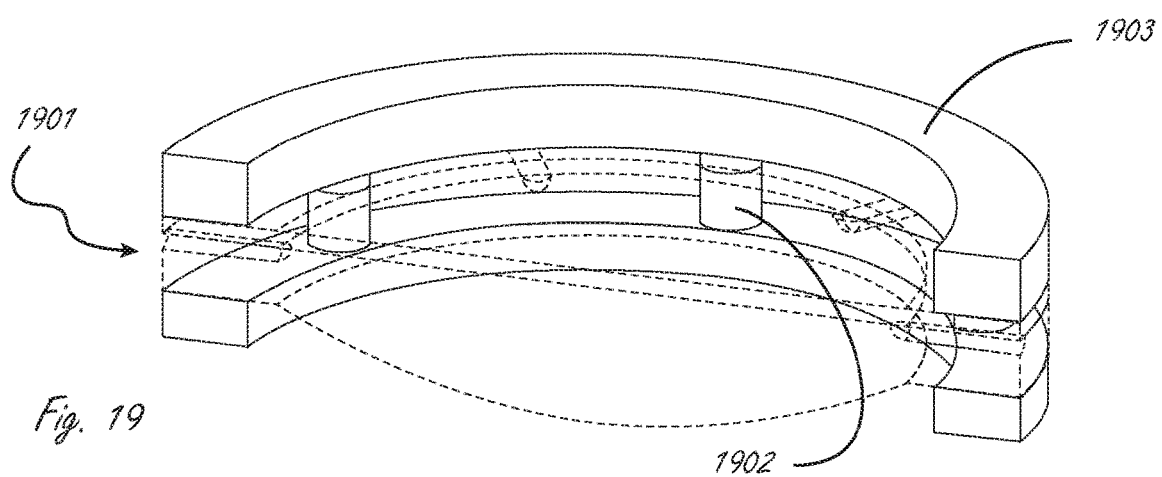
FIG. 19 depicts an alternate optical structure, in accordance with many embodiments.
Figure 20:
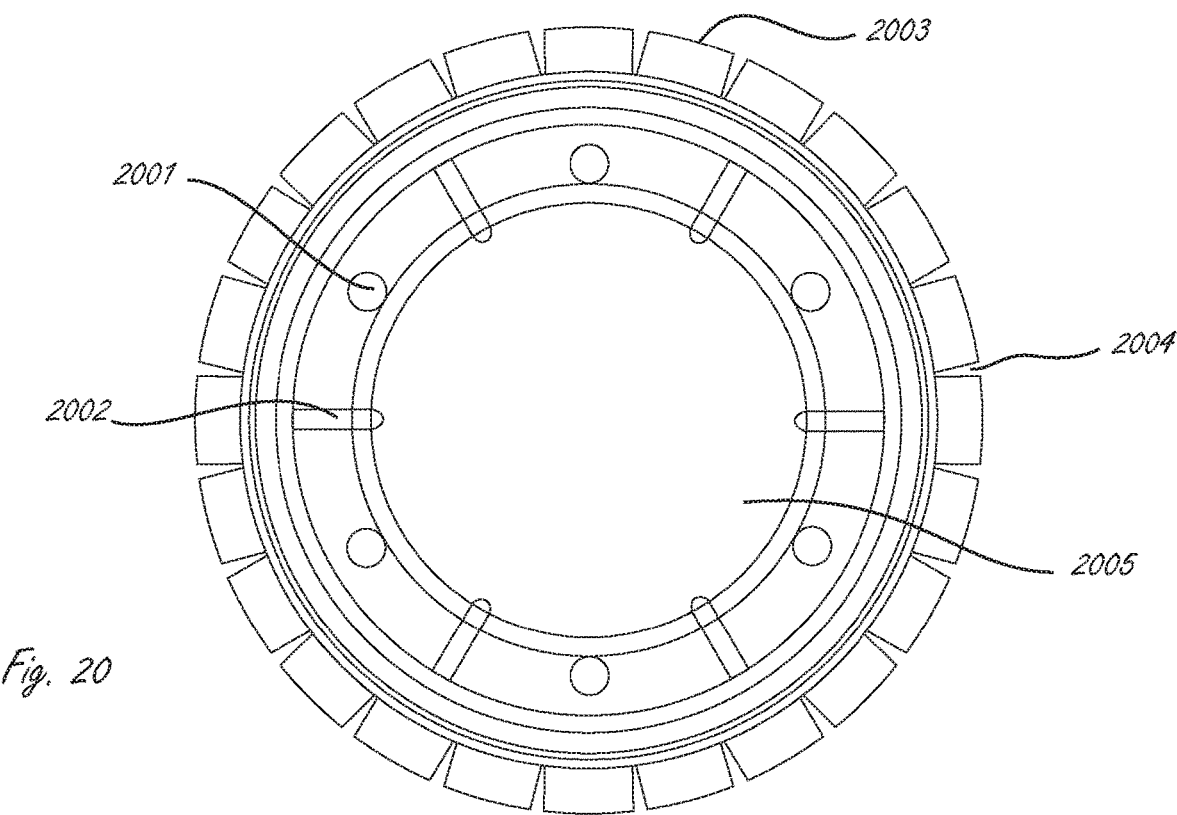
FIG. 20 is a top sectional view of an AIOL incorporating the optical assembly depicted in FIG. 19.

FIG. 20 is a top view of an AIOL incorporating an optical assembly such as that depicted in FIG. 19. Insertion and bonding points 2001 are shown. Accommodation can occur when fluid channels 2002 allow transfer of fluid into a central fluid optical element or lens chamber as haptic structures 2003 are compressed by the equatorial perimeter of the lens capsule (not shown). Haptic relief 2004 can provide for minimal circumferential stress during compression and quick recovery to the non-accommodating position when compression is relaxed.

Figure 21A:
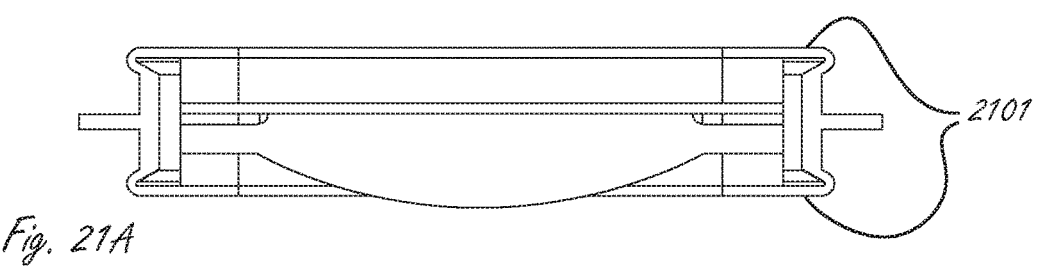
FIG. 21A is a lateral sectional view of the AIOL of FIG. 20.
Figure 21B:
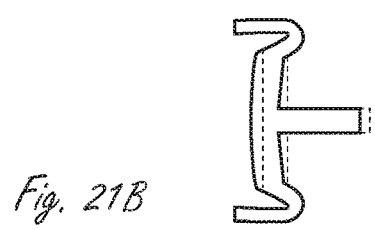
FIG. 21B is a modeled view of the haptic structure of FIGS. 20-22 under radial and pressure loading associated with forces generated by a capsular structure of the eye, in accordance with many embodiments
Figure 22:
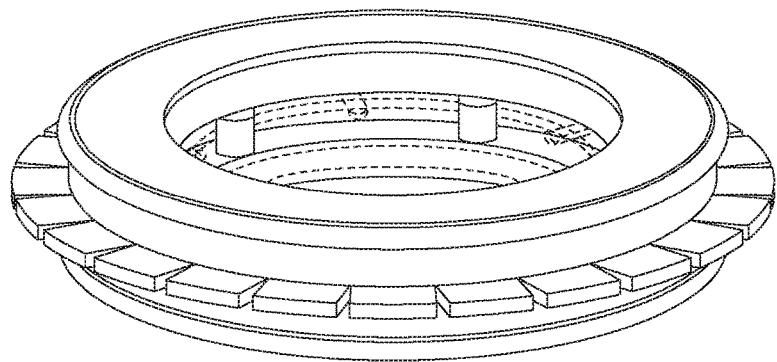
FIG. 22 is a view of a final AIOL assembly comprised of elements depicted in FIGS. 19-21, in accordance with many embodiments.

FIG. 21A is a lateral sectional view of the AIOL in FIG. 20 indicating points 2101 of minimal deformation in the haptic structure, and FIG. 21B depicts the deformations of the haptic structure given physiologically relevant loadings on the haptic structure. FIG. 22 is an isometric view of the AIOL assembly of FIGS. 20, 21A, and 21B.

Figure 23A:
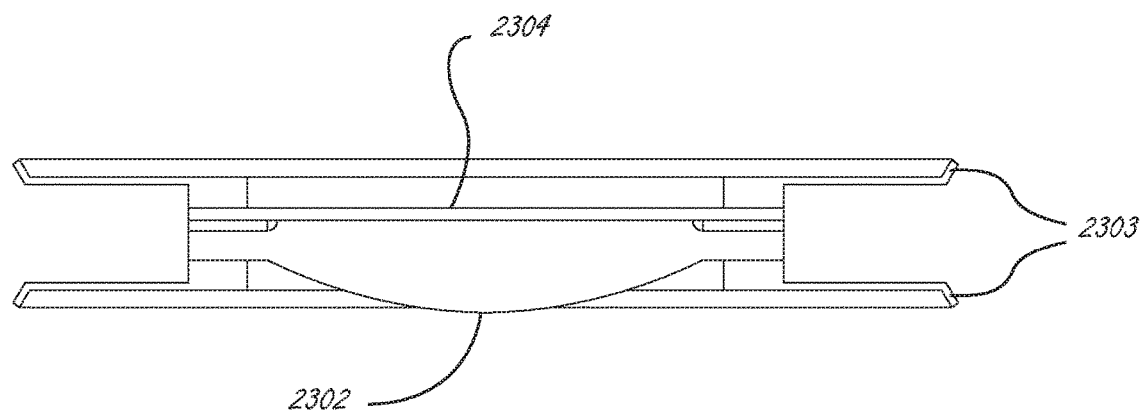
FIGS. 23A and 23B illustrate an alternate AIOL embodiment and method of manufacture, in accordance with many embodiments.
Figure 23B:
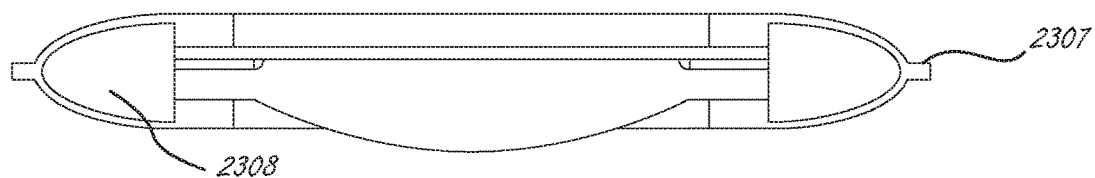

FIG. 23A is an alternate embodiment and assembly method wherein lens system 2302 is insert molded into haptic structure enclosure 2303. FIG. 23B shows the completed AIOL assembly with sealed haptic seam 2307, creating haptic chamber 2308, and a central fluid optical element or lens chamber 2304.

Figure 24:
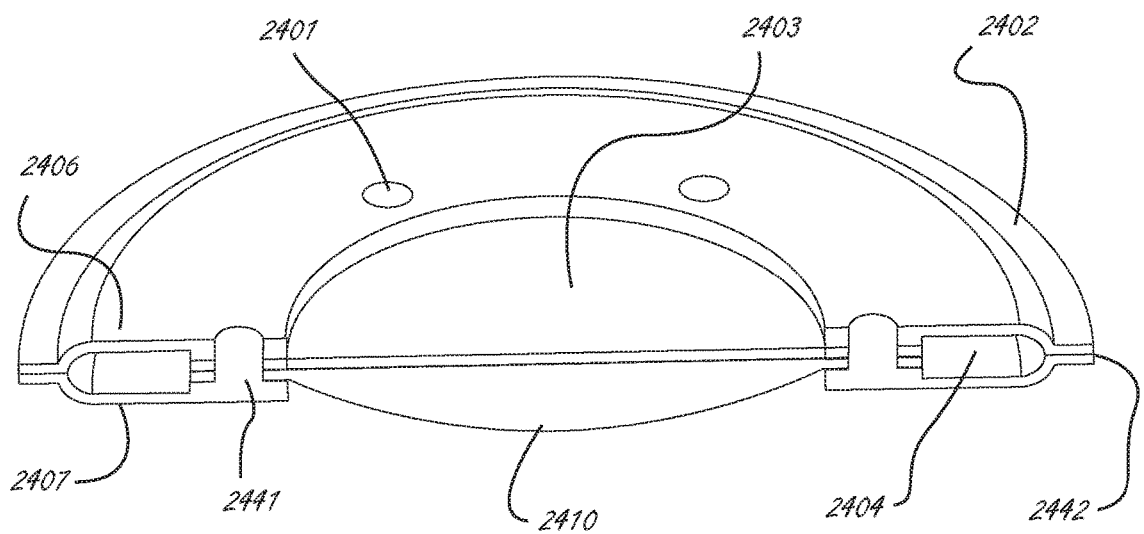
FIG. 24 depicts an alternate low-profile AIOL with alternate haptics and support structure, in accordance with many embodiments.

FIG. 24 depicts an alternate low-profile AIOL with alternate haptic structures and support structure comprised of the optical structure as described herein, posterior haptic structure 2406, and anterior haptic structure 2407. The optical structure can be aligned and secured via mounting to post 2441 and post 2441 can be bonded at point 2401. A haptic seam 2442 at the periphery 2402 of the AIOL can be bonded to form a seal and create a haptic fluid reservoir 2404. In such embodiments, the bonding at point 2401 and the haptic seam 2442 can form a fluid-tight seal to prevent fluid from leaking into and/or out of the haptic fluid reservoir 2404. The central optical structure may comprise an anterior planar member 2403 that may be deflectable and a posterior piano-convex member 2410 that may be resistant to deflection.

The embodiments described herein can be combined in one or more of many ways. For example, the embodiments of FIGS. 25A to 28B and 31 to 35B can be combined so as to include similar or alternative structures as described herein, and combinations thereof, in which the last two digits of the identifying numbers of the figures identify like structures.

Figure 25A:
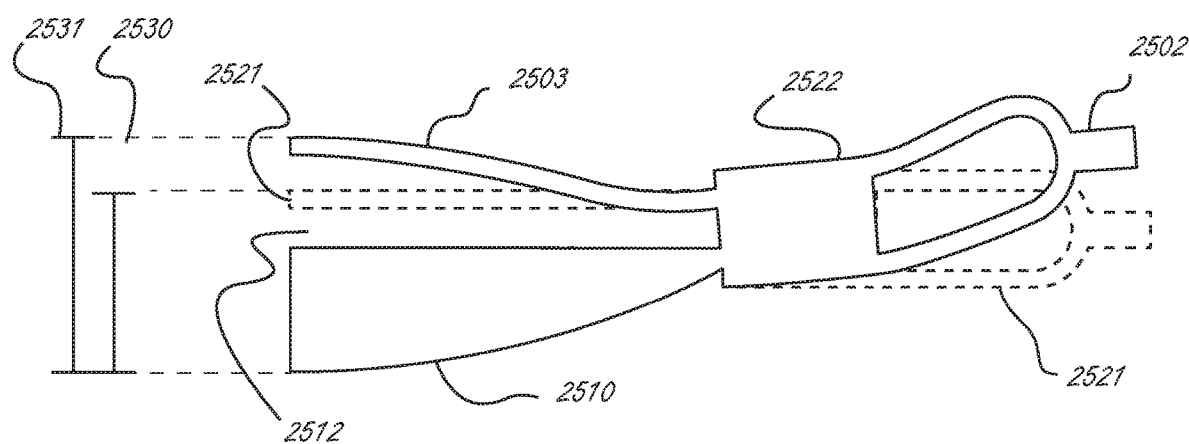
FIG. 25A is a model of the accommodation potential an AIOL similar that that of FIG. 24, in accordance with many embodiments.

FIG. 25A shows a model of the accommodation potential of the AIOL similar to that of FIG. 24. The AIOL comprises an undeflected configuration 2521 for far vision and a deflected configuration 2522 for near vision. The AIOL is shown in a non-accommodating configuration with a planar configuration of anterior planar deflectable member 2503 coupled to lever haptic structure 2502. An outer structure of haptic 2502 is configured to engage the lens capsule, and may comprise structures to reduce pressure on the capsule as described herein. A stiff member 2510 may comprise a lens to provide optical power for far vision. The deflectable member 2503 may comprise a substantially planar member having a substantially constant thickness, for example. The deflectable member 2503 comprises an inner optical portion and an outer, peripheral extension. The extension extends between the inner optical portion and the rotating haptic structure 2502. When the inner optical portion comprises the convex deflection, the fluid of the chamber beneath the inner optical portion is shaped to provide an optical correction.

The deflectable member 2503 and stiff member 2510 define at least a portion of an inner chamber 2512. The inner chamber 2512 comprises a fluid having an index of refraction greater than an index of refraction of an aqueous humor of the eye. When the deflectable member 2503 comprises an increased curvature, the internal fluid comprises a convex lens shape and provides additional optical power.

The AIOL comprises a central thickness extending from an outer surface of the stiff member 2510 to an outer surface of the deflectable member 2503. The central thickness may comprise a first central thickness 2530 of the AIOL lens in a far vision configuration, and a second central thickness 2531 of the AIOL lens in a near vision configuration. The increase in thickness of the lens centrally is related to the increased optical power of the lens. The increased optical power of the lens is also approximately inversely related to a square of the diameter of the central optical portion. The extension portion can decrease the diameter of the optical portion and provide increased optical power for an amount of change between first distance 2530 and second distance 2531.

The stiff member 2510 is connected to haptic structure 2502, such that the haptic structure 2502 rotates when the lens accommodates for near vision. The haptic structure 2502 extends to a first anchor region such as an anchor point (in a similar location to anchor point 2640 shown in FIG. 26) about which the haptic rotates relative to the stiff member 2510. The haptic structure extends a distance from the first anchor region to the wall of the lens capsule. The haptic structure 2502 extends to a second anchor region such as second anchor region or point (in a similar location to anchor region or point 2641 shown in FIG. 26). The second anchor region couples to the deflectable member 2503 in order to induce inward force on the deflectable member. The distance from the first region to the outer structure of the haptic engaging the lens capsule is greater than the distance from the first region to the second region. This difference in distance provides mechanical leverage of the lens capsule forces on the deflectable member 2503. The force of the lens capsule on the deflectable member 2502 induces a convex deflection 2524 of the deflectable membrane. The extension 2511 comprises an opposite concave curvature.

Although the extension portion may comprise an opposite concave curvature, this curvature can be provided in one or more of many ways to decrease visual artifacts. The amount of accommodative optical correction can be approximately 2 to 10 Diopters, such that the opposite curvature of the extension portion may comprise no patient perceptible optical affect. Also, the eye naturally comprises spherical aberration, and small amounts of aberration may not be perceptible. Further, the lens can be sized such that the pupil covers at least a portion of the oppositely curved concave portion. In at least some embodiments, the thickness profile of the extension portion of the deflectable component can be thinner to localize the opposing curvature to the thinner outer portion of the deflectable member. Work in relation to embodiments suggests that the substantially planar deflectable member decreases visual artifacts that may occur with internal reflections, for example, although a curved deflectable member can be provided and configured to inhibit visual artifacts related to internal reflections.

In many embodiments, the haptic 2502 comprises an outer reservoir coupled to chamber 2512, and forces of the haptic to the outer reservoir can urge fluid toward the chamber 2512 when the eye accommodates, in addition to inward forces of the haptic 2502 at anchor point 2541, for example.

The AIOLs as described herein can be studied with finite element modeling. While the finite element modeling can be performed in one or more of many ways, in many embodiments, the finite element modeling is performed with known commercially available software such as Abaqus, known to a person of ordinary skill in the art. The lenses as described herein can be modeled with a finite element mesh and known material properties of one or more materials as described herein, and the response of the AIOL to lens capsule forces determined.

A person of ordinary skill in the art can take the finite element modeling output of the lenses as described herein and determine the optical power of the AIOL in response to lens capsule force, for example, in order to determine appropriate AIOL parameters to provide accommodation to the eye. At least FIGS. 25A to 28B and 31 to 35B show responses of an AIOL to forces of the capsular bag in accordance with embodiments.

Figure 25B:
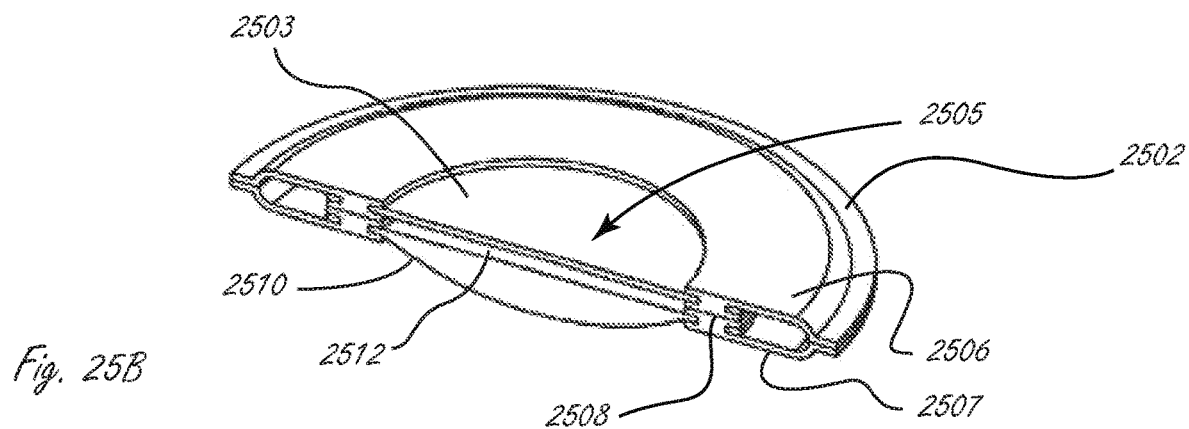
FIGS. 25B and 25C show perspective sectional views of the AIOL of FIG. 25A.

FIG. 25B shows a sectional view of the model from which FIG. 25A was developed. Note that the lens or optical structure 2505 comprises additional space between the individual lenses and that the posterior and anterior haptic structures 2506 and 2507 incorporate an additional mating surface 2508. In such embodiments, the haptic structures 2506, 2507 may be over molded onto the lens or optical structure(s) 2503. The haptic structures 2506, 2507 may be comprised of a thermoplastic or solvent weldable material thereby facilitating the joining of the two halves. The features comprising mating surface 2508 may also include fluid paths 2509 as shown in FIG. 25C or locating and alignment features not shown.

Figure 25C:
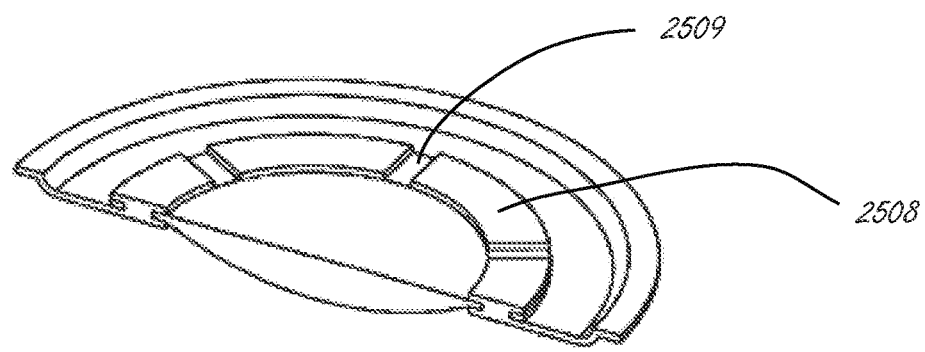

In embodiments according to the AIOL of FIGS. 25A-25C, the deflection of the deflectable structure or lens 2503 may be primarily driven by mechanical forces applied to the peripheral edge of haptic structure 2502 transmitted to the deflectable structure or lens 2503 by the intermediary portion of the haptic structure 2502. Since the deflectable structure or lens 2503 does not sit directly on the non-deflecting lens 2510, the deflectable structure or lens 2503 may be allowed to buckle as shown. In such embodiments, the deflection experienced by the deflectable lens or structure 2503 will increase the accommodating power of fluid optical element or lens created between the deflectable structure or lens 2503 and non-deflecting structure or lens 2510 and the volume of the fluid optical element will increase as accommodating power increases. Additional optical fluid may therefore be required and provided from the reservoir comprised in the haptic structure 2502 via channels 2509.

Figure 26:
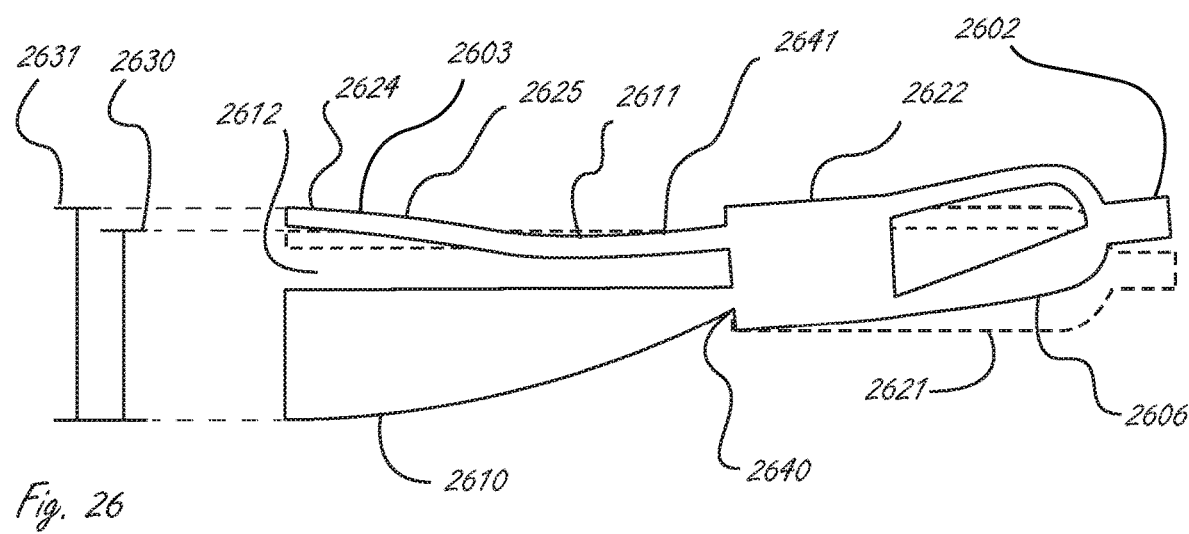
FIG. 26 shows a model of an AIOL similar to that of FIG. 25A deformed.

FIG. 26 represents a variation on the AIOL of FIGS. 25A-25C, wherein the anterior haptic structure 2602 has been stiffened at haptic structure wall 2606 to better couple forces into the deflectable structure 2603. Forces provided from the equatorial region of the capsular structure of the eye are coupled via the periphery of the haptic structure 2602 creating a moment around flexural point 2611. The moment produces an outward deflection of deflectable structure 2603. The FIG. 26 AIOL may include elements similar to those in that of FIGS. 25A-25C, such as a stiff member 2610, an inner chamber 2612, a deflected configuration 2622, a convex deflection 2624, an inner optical portion 2625, a first central thickness 2630, a second central thickness 2631, an anchor point 2640, and an anchor point or region 2641.

Figure 27:
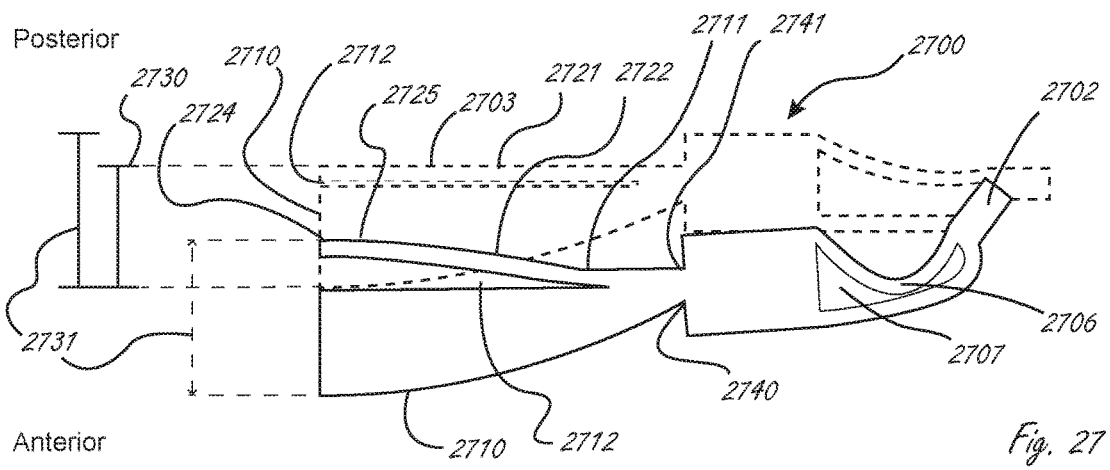
FIG. 27 shows a model of the accommodation potential of the AIOL of FIG. 24.

FIG. 27 is a representation of the accommodating potential of the AIOL 2700 similar to that of FIG. 24. The AIOL includes a deflectable structure or anterior lens 2703, a stiff or non-deflectable member 2710, and a haptic structure 2702 supporting the deflectable structure 2703 and stiff member 2710. The deflectable member 2703 can be located on the anterior portion of the AIOL and the stiff member 2710 can be located on the posterior portion of the AIOL when placed in the eye. In this embodiment, the haptic wall 2706 of haptic structure 2702 is coupled to a haptic reservoir 2707 in fluid communication (e.g., through fluid channels) with a fluid lens structure of inner chamber 2712 of the AIOL. Deflections of deflectable member 2703 of the optical structure can be provided at least in part by fluid pressure created by the deflection of the haptic structure 2702 and haptic wall 2706. For example, the periphery of the haptic structure 2702 can be rotated by forces applied to the periphery of the haptic structure 2702 (e.g., inward forces of the capsular structures), causing in turn an inward collapse in the haptic reservoir 2707 thereby increasing the pressure within and transferring fluid from the haptic reservoir 2707 into the fluid lens structure 2712. The increase in volume of fluid lens structure 2712 can cause the deflectable member 2703 to move anteriorly relative to the stiff member 2710, thereby increasing in curvature and increasing the optical power of the eye. In some embodiments, the rotation of the haptic structure 2702 can further cause the deflectable structure 2703 and the stiff member 2710 to move together relative to the haptic structure 2702 in a direction opposite of the direction of rotation to increase the optical power of the eye. The AIOL 2700 may further include elements similar to those of the AIOLs described in FIGS. 25A-25C and 26. For instance, the AIOL 2700 may further include a flexural point 2711, a deflected configuration 2722, a convex deflection 2724, an inner optical portion 2725, a first central thickness 2730, a second central thickness 2731, an anchor point 2720, and an anchor point or region 2741.

Figure 28A:
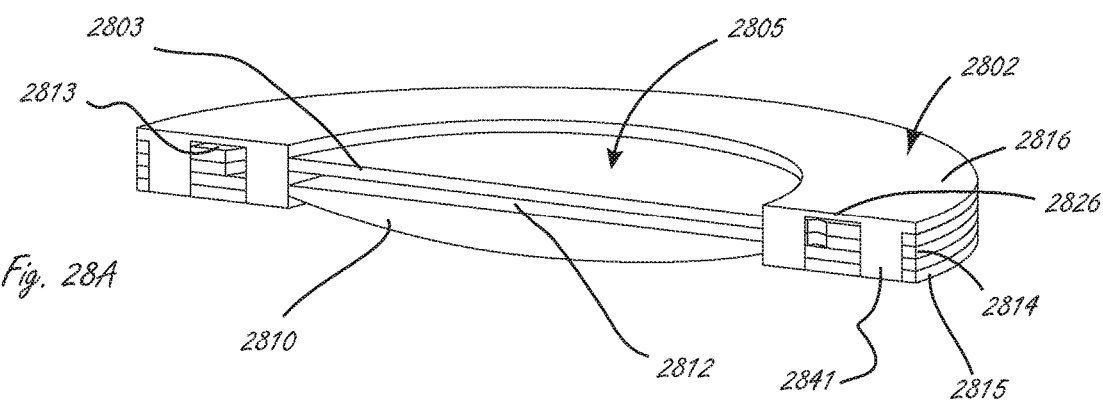
FIG. 28A shows a perspective sectional view of another AIOL, in accordance with many embodiments.
Figure 28B:
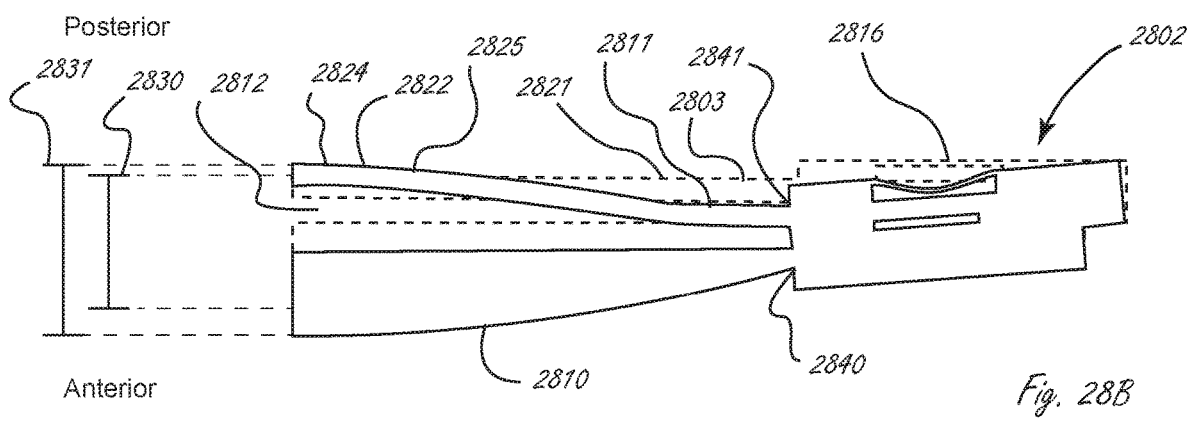
FIG. 28B shows a model of the accommodation potential of the AIOL of FIG. 28A.

FIG. 28A and FIG. 28B illustrate a variation on the AIOL of FIG. 25 and FIG. 26. FIG. 28A shows a half section of the AIOL. The AIOL is comprised of an optical or lens structure 2805, in turn comprised of a deflectable structure or member 2803, a stiff or non-deflectable lens or member 2810, and a fluid-filled lens chamber or fluid optical element 2812. The optical or lens structure 2805 can be held together by a haptic structure 2802. The haptic structure 2802 may comprises an alignment structure 2816 upon which the elements of the AIOL can be stacked during assembly. The alignment structure 2816 may also comprise alignment posts 2822 and a diaphragm element 2826. The other elements include a spacer 2814 and a cover seal 2815. The materials from which the haptic structure 2802 is comprised are typically solvent and or heat weldable. The spacer element 2814 comprises channeling which facilitates fluid communication between the fluid-filled lens chamber 2812 and the haptic reservoir 2813 comprising diaphragm 2826. The fluid-filled lens chamber 2812 and the haptic reservoir 2813 may form a closed system such as a sealed reservoir. In this embodiment, the haptic reservoir 2813 is not deformed as by the activation forces applied to the periphery of the haptic structure 2802. Instead, the diaphragm element 2826, which may be isolated from experiencing direct forces delivered from the capsular structure of the eye, deflects in accommodation of the pressure changes within the fluid-filled lens chamber or fluid optical element 2812. Diaphragm element 2826 may be fluidly coupled to the fluid-filled lens chamber 2812 such that an anterior deflection of diaphragm element 2826, as shown in FIG. 28B, corresponds to an increase in the volume of fluid-filled lens chamber 2812 and a posterior deflection of deflectable structure 2803. Such embodiments may have advantage when it is desired to use only the forces generated at the equatorial region of the capsule to mediate accommodation. In such embodiments, pressure in internal lens chamber can be negative. The AIOL of FIGS. 28A-28B may further include elements similar to those of the AIOLs described in FIGS. 25A-25C, 26, and 27 such as a flexural point 2811, an undeflected configuration 2821, 2821, a convex deflection 2824, an inner optical portion 2825, a first central thickness 2830, a second central thickness 2831, an anchor point 2820, and an anchor point or region 2841.

In many of the embodiments described above, such as those of FIGS. 24 through 28B, the AIOL will be assembled when all of its components are in a dry state. Where the optical or lens structures are comprised of hydrophilic PMMA copolymers, the system will be hydrated at the completion of assembly. When hydrated, the hydrophilic lens components will swell thereby enhancing the sealing of the chambers within the structure.

Figure 29:
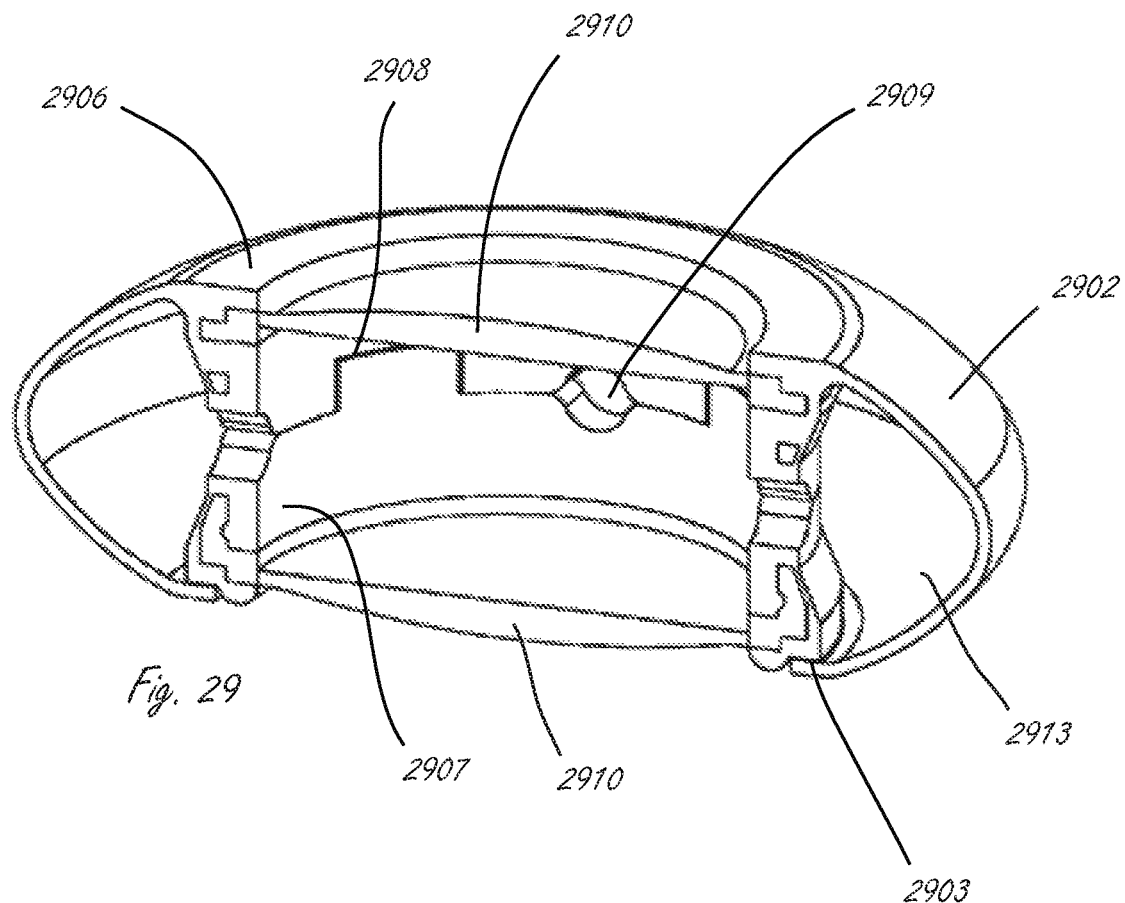
FIG. 29 shows a perspective sectional view of yet another AIOL, in accordance with many embodiments.

FIG. 29 shows an embodiment of an AIOL wherein the lens or optical structure is created by over molding a lens 2910 into each of two halves of the AIOL 2906 and 2907. As shown, the lenses are the same. In some embodiments, however, it may be desirable that they are different such as when one lens is deflectable and the other not. The haptic structure 2902 comprising the haptic fluid chamber 2913 can be created on assembly by folding the peripheral element of the structure 2906 and bonding it to a bond surface 2903. In this embodiment, the seam 2908 may be left un-bonded such as at location 2909. In such embodiments, as pressure is applied to the outer surface of the haptic structures 2902, lenses 2910 will be displaced and deflected. Such structures may also provide advantage by minimizing the delivery cross-section, as the upper and lower halves can telescope on each other when the structure is compressed.

Figure 30:
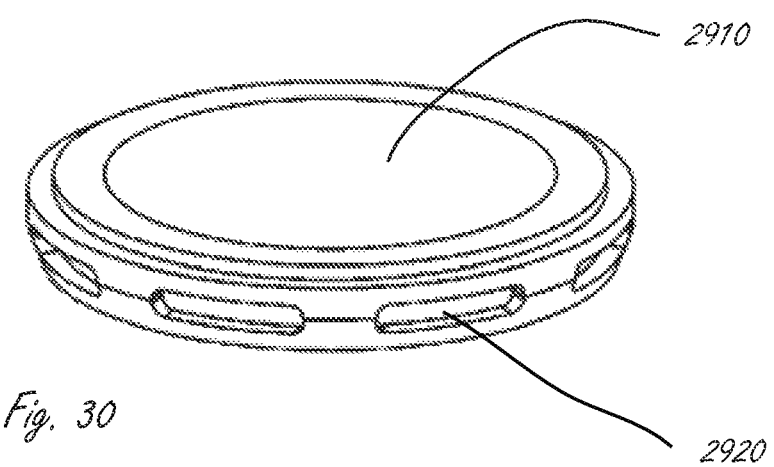
FIG. 30 shows the lenses associated with the AIOL of FIG. 29.

FIG. 30 illustrates a lens structure from the AIOL of FIG. 29 incorporating a hole feature 2920 which facilitates fixation of the components of the haptic structure 2902 when the lens is over-molded into a either half of the AIOL structure.

Figure 31:
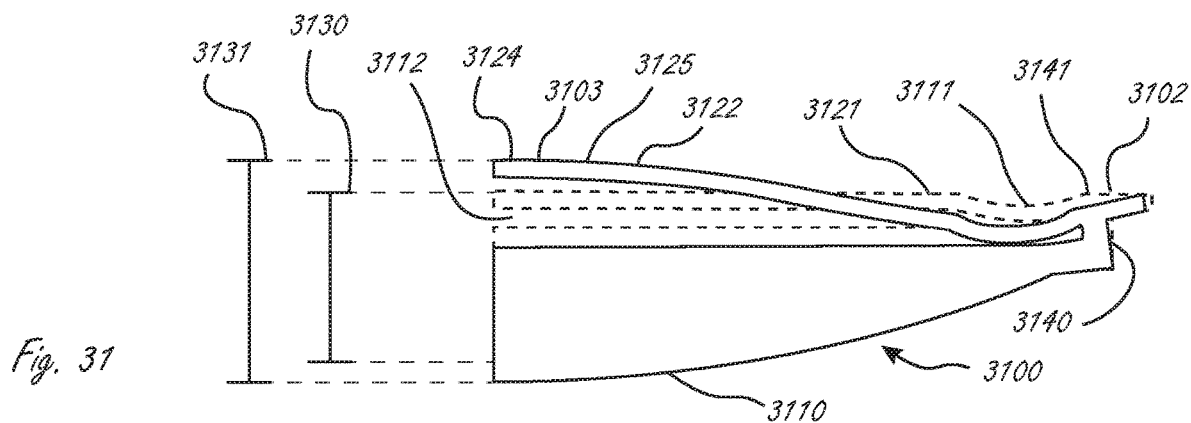
FIG. 31 shows a model of the accommodation potential of another AIOL, in accordance with many embodiments.

FIG. 31 shows an embodiment of an AIOL 3100 comprising a deflectable member 3103 comprising a concave region 3111, a stiff or non-deflectable member 3110, and a fluid-filled chamber 3112. In this embodiment, the concave surface of concave member 3111 causes an inward deflection of the central portion of the concave region 3111 relative to the stiff or non-deflectable member to produce an outward deflection of deflectable member 3103 relative to the stiff or non-deflectable member into a convex configuration. In many embodiments, the inward deflection of the concave region 3111 is in the anterior direction and the outward deflection of the central portion of the concave member 3111 is in the posterior direction when the AIOL 3100 is placed in the lens capsule, or vice versa in alternative embodiments. In many embodiments, the concave region 3111 has a uniform thickness. The AIOL 3100 may further include elements similar to those of the AIOLS described above (such as in FIGS. 25A-25C, 26, 27, and 28A-28B), such as an inner chamber 3112, a deflected configuration 3122, a convex deflection 3124, an inner optical portion 3125, a first central thickness 3130, a second central thickness 3131, an anchor point 3140, and an anchor point or region 3141.

Figure 32:
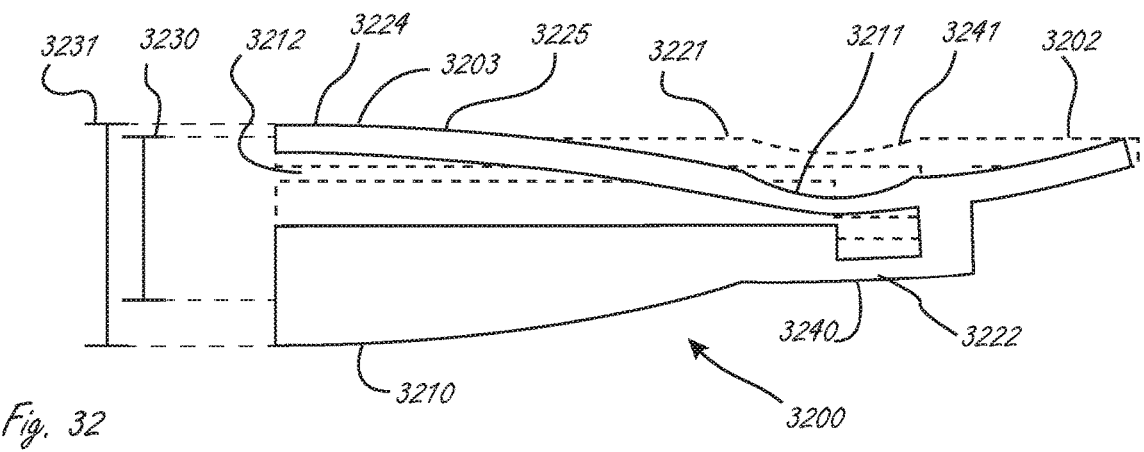
FIG. 32 shows a model of the accommodation potential of yet another AIOL, in accordance with many embodiments.

FIG. 32 shows an embodiment of an AIOL 3200 comprising a deflectable member 3203 comprising a concave region 3211, a stiff or non-deflectable member 3210, a fluid-filled lens chamber 3212, and a haptic structure comprising a wall 3221. In this embodiment, the concave surface of concave member 3211 converts a rotation of the haptic and haptic structure wall 3221 relative to stiff member 3210 into an outward deflection of deflectable member 3203 relative to stiff member 3210, such that a center of the deflectable member 3203 separates from stiff member 3210 as the outer portion of the deflectable member moves toward the stiff member. In many embodiments, the inward deflection of the concave region 3211 is in the anterior direction and the outward deflection of the central portion of the concave member 3211 is in the posterior direction when the AIOL 3200 is placed in the lens capsule, or vice versa in alternative embodiments. In many embodiments, the concave region 3211 thins the remainder of the deflectable member 3203 so as to act as a hinge. For example, the concave region 3211 may comprise a concave cut-out of an external surface region of the deflectable member 3203. The AIOL 3200 may further include elements similar to those of the AIOLs described above (such as in FIGS. 25A-25C, 26, 27, 28A-28B, and 31), such as a deflected configuration 3222, a convex deflection 3224, an inner optical portion 3225, a first central thickness 3230, a second central thickness 3231, an anchor point 3240, and an anchor point or region 3241.

Figure 33:
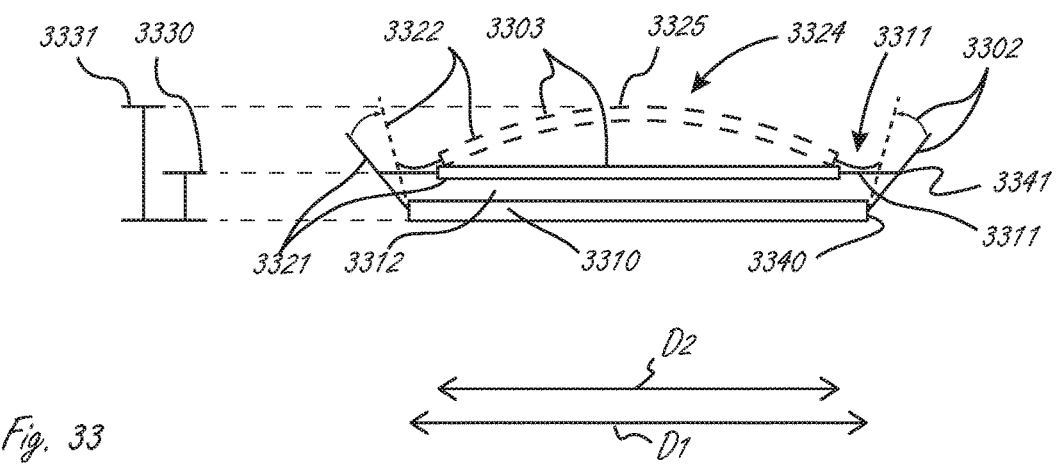
FIG. 33 shows a schematic of the accommodation potential of an AIOL, in accordance with many embodiments

FIG. 33 shows a schematic of an AIOL in an undeflected configuration 3321 and a deflected configuration 3322. The AIOL comprises a stiff or non-deflectable member 3310 (e.g., one more convexly curved optical surface), a deflectable member 3303 (e.g., an optical material having a uniform and constant thickness to inhibit distortion) that can be deflected to a deflected configuration 3325, a fluid-filled chamber 3312, and a lever or cantilevered haptic structure 3302. The lever structure haptic 3302 is connected to the stiff member 3310 at a first anchor point 3340 or region, such as a thin portion near an outer edge of the stiff member 3310. The first anchor point 3340 or region may be any point or region along an axis extending though the outer edge of the stiff member 3310 and the perimeter of the lever structure haptic 3302. When the AIOL is placed in the lens capsule of the eye, the perimeter of the lever structure haptic 3302 may extend in a direction transverse or normal to an optical axis of the eye. The lever structure haptic 3302 is also connected to the deflectable member 3303 through a resilient extension 3311 at a second anchor point 3341 or region. In many embodiments, the resilient extension 3311 has a thickness less than the thickness of the deflectable member 3303. In these embodiments, the lever structure haptic 3302 has a thickness and a length greater than the thickness. The length of lever structure haptic 3302 can be greater than the distance between the first anchor point 3340 and second anchor point 3341, such that mechanical leverage (e.g., an inward force from the lens capsule or pressure of the eye) can be applied to the second anchor point 3341 from the end of the lever structure haptic 3302 contacting the lens capsule of the eye.

In many embodiments, the rotation of lever structure haptic 3302 about the first anchor point 3340 of stiff member 3310 can exert a force on resilient extension 3311 in order to deflect resilient extension 3311 and deflectable member 3303 in opposite directions with opposite curvatures. For example, the rotation may cause resilient extension 3311 to move closer to the stiff member 3310 with an outer concave surface and deflectable member 3303 to separate further away from the stiff member 3310 with a convex outer surface. The deflection of deflectable member 3303 can involve a transition from a first diameter DI to a second diameter D2, the second diameter D2 being a smaller than the first diameter DI. The decrease in diameter size can cause a convex deflection 3324 such as a spherical deflection of the deflectable member 3303 away from the stiff member 3310. In the deflected configuration 3322, the convex deflection 3324 of the deflectable member 3303 can be characterized by a curvature, and the resilient extension 3311 can be characterized by an opposite curvature. The curvature of the convex deflection 3324 can be the opposite of the curvature of the resilient extension 3311. For example, curvature of the convex deflection 3324 may be a positive curvature along an outer surface of the AIOL and the curvature of the extension may comprise a negative curvature along the outer surface of the AIOL.

The change in diameter of the deflectable member 3303 from DI to D2 may produce a corresponding amplified movement away from the stiff member 3310, such that the deflection height between a first height 3330 and a second height 3331 is greater than the corresponding change in diameter. In such embodiments, the positive curvature of the spherical deflection can cause the fluid-filled chamber 3312 to assume a more convexly curved profile to change the optical power of the AIOL. The change in shape of the fluid-filled chamber 3312 can cause an increase in volume and thereby pull fluid into the fluid-filled chamber 3312, such as from a peripheral reservoir. Alternatively, or in combination, the change in shape of the deflectable member 3303 and fluid chamber 3312 may occur without a substantial change in volume of the chamber 3312. For example, the change in the shape of the fluid-filled chamber 3312 can cause a redistribution of the internal fluid to change optical power such as by drawing fluid from an outer portion of the chamber 3312 and without drawing fluid from a peripheral reservoir. Also, the rotation of the lever structure haptic 3302 may cause the deflectable member 3303 and the stiff member 3310 to translate together in the anterior direction relative to the outer edge of the lever structure haptic 3302 when the AIOL is placed in the lens capsule. Such translation may further change the optical power of the eye. The separation of the deflectable member 3303 away from the stiff member 3310, the deflection of the deflectable member 3303 to increase its curvature, and the translation of deflectable member 3303 and the stiff member 3310 together in the anterior direction may combine to change the optical power of the eye. For example, this combination can amplify a small contraction in the lens capsule housing the AIOL into a significant change in optical power of the AIOL. Such a change in optical power may be significantly greater than any of one of separation, deflection, and translation motions alone.

The haptic structures described herein may comprise of silicones, urethanes, or other suitable thermoplastics, PMMA and PMMA copolymers. In many embodiments, the haptic structures comprise the same or similar materials as the optical structure.

Figure 34A:
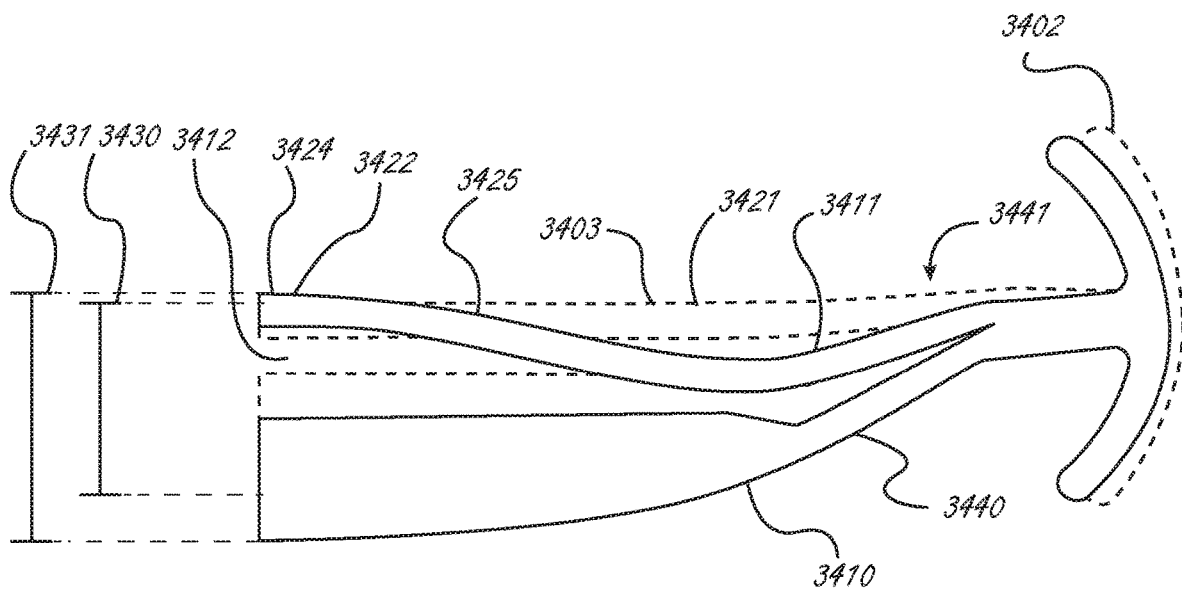
FIG. 34A shows an AIOL, in accordance with embodiments.

FIG. 34A shows an AIOL in accordance with embodiments. As noted herein, the undeflected configuration 3421 is shown in dashed lines and the deflected configuration 3422 is shown with solid lines. The AIOL comprises the inner optical portion 3425 and the extension as described herein. Similar structures identified with similar last two digits are identified herein.

Figure 34B:
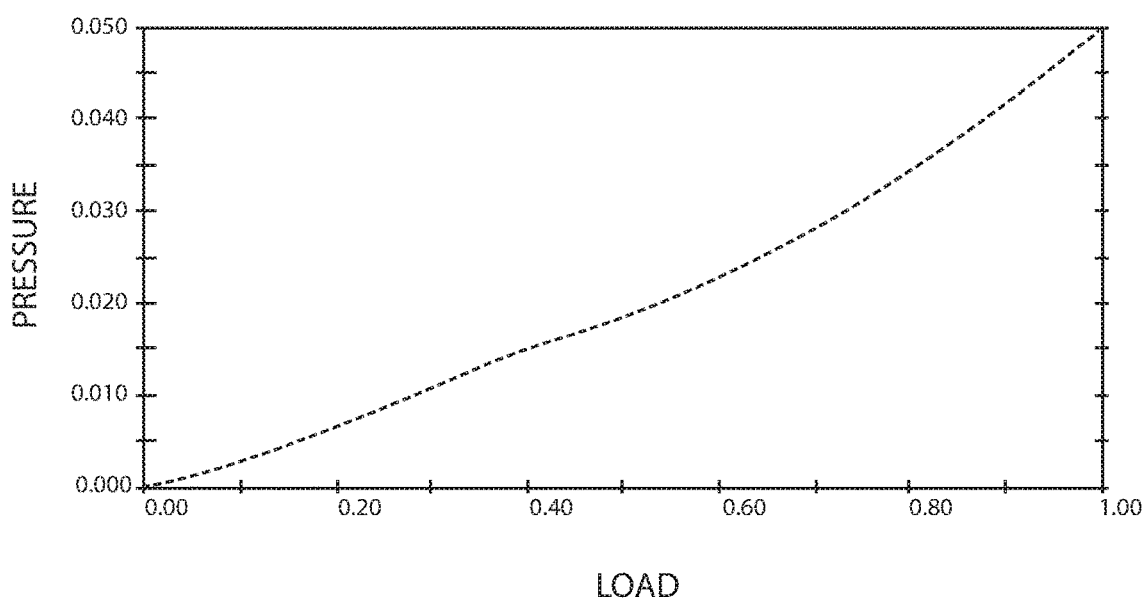
FIG. 34B shows internal pressure of the AIOL chamber as in FIG. 34A.

FIG. 34B shows internal pressure of the AIOL chamber as in FIG. 34A. The pressure of the internal chamber 3412 is shown to increase with load. This increased pressure with load indicates that both the inward force of the lever haptic structure and internal pressure of the AIOL contribute to the convex deflection 3424 of the inner optical structure 3425.

The AIOL of FIGS. 34A-34B may further include elements similar to those of the AIOLs described above (such as in FIGS. 25A-25C, 26, 27, 28A-28B, 31, and 32), such as a haptic structure 3402, a deflectable structure or anterior lens 3403, a stiff member 3410, a flexural point 3411, a first central thickness 3430, a second central thickness 3431, an anchor point 3440, and an anchor point or region 3441.

Figure 35A:
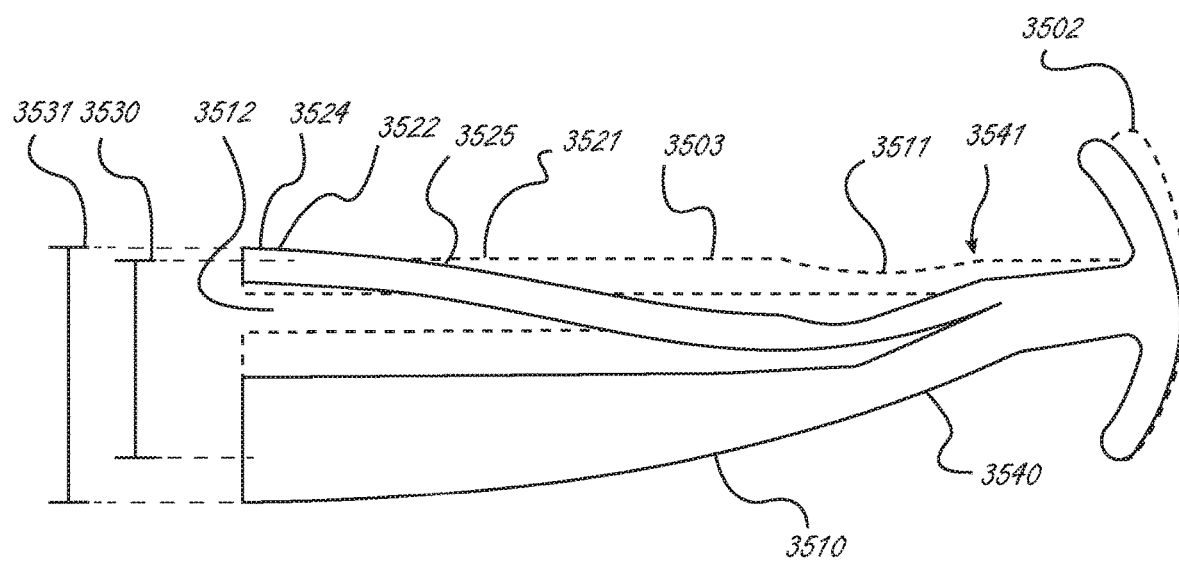
FIG. 35A shows an AIOL, in accordance with embodiments.

FIG. 35A shows an AIOL in accordance with embodiments. As noted herein, the undeflected configuration 3521 is shown in dashed lines and the deflected configuration 3522 is shown with solid lines. The AIOL comprises the inner optical portion 3525 and the extension as described herein. Similar structures identified with similar last two digits are identified herein.

Figure 35B:
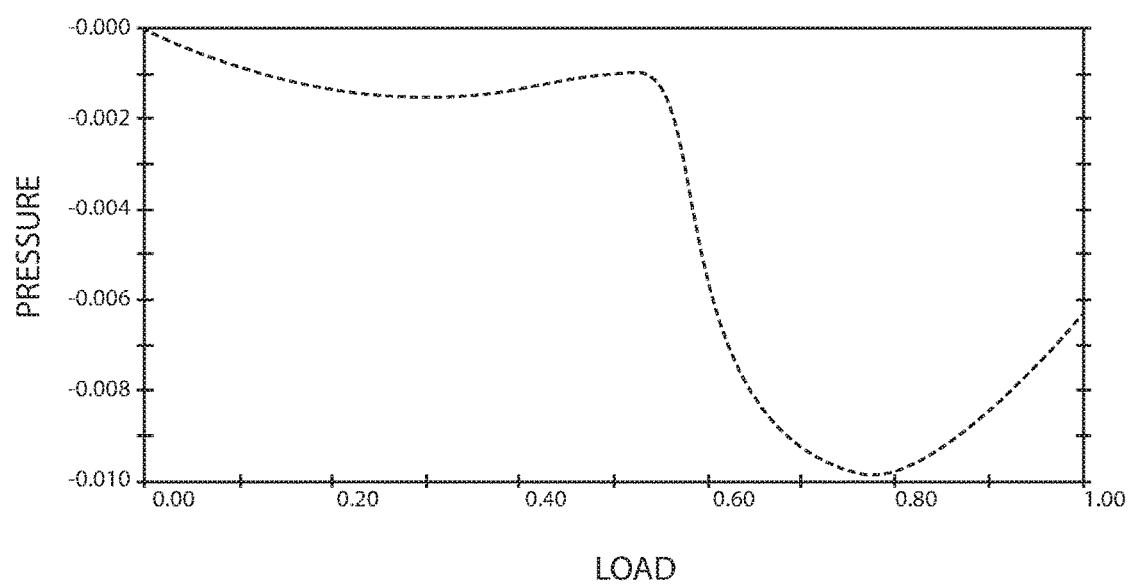
FIG. 35B shows internal pressure of the AIOL chamber as in FIG. 35A.

FIG. 35B shows internal pressure of the AIOL chamber as in FIG. 35A. The pressure of the internal chamber 3512 is shown to decrease with load. This decreased pressure with load shows that the inward force of the lever haptic structure is capable of providing the convex deflection 3524 of the inner optical structure 3525. Furthermore, as the pressure is negative, this pressure response curve shows that the deflection and change in optical power are the result of mechanically driven inward radial loading as opposed to from pressure from the fluid of the chamber. FIG. 35B shows that the inward force of the lever haptic structure is capable of deflecting deflectable member 3503 with negative pressure of the internal chamber.

The AIOL of FIGS. 35A-35B may further include elements similar to those of the AIOLs described above (such as in FIGS. 25A-25C, 26, 27, 28A-28B, 31, 32, and 34A-34B), such as a haptic structure 3502, a deflectable structure or anterior lens 3503, a stiff member 3510, a flexural point 3511, an inner chamber 3512, a convex deflection 3512, a first central thickness 3530, a second central thickness 3531, an anchor point 3540, and an anchor point or region 3541.

Bonding

Bonding can be used to adhere one or more of many AIOL structures as disclosed herein. The structures can be bonded in one or more of many ways as described herein, and the steps, processes and materials can be combined to provide improved bonding of the AIOL structures.

The bonding of components as described herein can be used with one or more of many IOL components, can be used with one or more of many IOL materials, can be used with accommodating and non-accommodating IOLs, and can be used with one or more of many AIOLs as described herein, for example. The accommodating IOL may comprise one or more haptics to couple the disc shaped components to the capsular bag in order to change the optical power of the lens in response to deformations of the capsular bag. In many embodiments, the one or more haptics comprise chambers fluidically coupled to the chamber comprising the first and second lens components. The haptics can be made of a soft material as described herein, such as an acrylate polymer or a silicone polymer, or combinations thereof, for example.

Although reference is made to bonding stiff, machined polymer, the bonding as disclosed herein can be used with one or more of hydrated polymer, soft hydrated polymer, machined polymer, molded polymer, molded dry polymer, molded stiff polymer, molded soft polymer, or molded hydrated polymer, and combinations thereof, for example.

In many embodiments, the AIOL comprises a first component and a second component. A first component comprises a first disc-shaped structure and the second component comprises a second disc-shaped structure. An annular structure extends between the first disc shaped structure and the second disc shaped structure to define a chamber containing a fluid having an index of refraction greater than about 1.336, which is the index of refraction of the aqueous humor of the eye. When one or more of the first disc structure or the second disc structure increases in curvature, optical power of the AIOL increases.

The first and second components can be bonded to each other at one or more bonding surfaces. The location of the bonding surface(s) can be selected to decrease the impact of the bonding surface(s) on the optical properties of the AIOL. For example, a bonding surface can extend circumferentially around one or more of the annular structure, the first disc shaped component, the second disc shaped component, and combinations thereof. In many embodiments, the bonding surface is located in or near a seam extending circumferentially around the one or more of the annular structure, the first disc shaped component, the second disc shaped component, and combinations thereof, which bonds the components together. Locating the seam away from the optical portions of the first and second components provides improved optical properties.

In many embodiments, the first and second components are machined on a lathe to provide rotationally symmetric structures, such as the first disc shaped structure and the second disc shaped structure. One or more of the first component or the second component may comprise the annular structure prior to bonding the components together. One or more annular grooves can be provided on the first component and the second component in order to align optically the first component with the second component. One or more portions of the annular grooves, or other shaped groove or grooves, can be used as bonding surfaces for bonding the first and second components together.

Various techniques can be used to bond the first and second components to each other. For example, direct bonding methods can be used to join the bonding surfaces described herein. Direct bonding methods can advantageously provide a continuous bonded interface having similar material and mechanical properties as the rest of the structure. For example, the bonded interface may swell similarly to the first and second components of the structure. Exemplary direct bonding methods may include thermal bonding, solvent bonding, localized welding, or surface modification.

Thermal bonding of the first and second components can involve heating the components (e.g., at or near the bonding surfaces) to a temperature near or above the glass transition temperature of one or both of the components. During the heating process, pressure can be applied to increase the contact forces between the components at the bonding surfaces. The use of suitable temperature and pressure conditions can cause the polymer chains of the components to interdiffuse between the bonding surfaces and entangle with each other, thereby bonding the first and second components together.

Solvent bonding can involve applying a suitable solvent to the bonding surfaces of the first and second components. The solvent can solvate the polymer chains of the components at the bonding surfaces, thereby increasing chain mobility and interdiffusion between the bonding surfaces. For instance, solvent bonding of components fabricated from a copolymer of HEMA and MMA may be facilitated by treating the bond surfaces with a suitable solvent. Exemplary solvents can include EGDMA, diethylene glycol dimethacrylate (DEGDMA), triethylene glycol dimethacrylate (TEGDMA), water, methanol, ethanol, acetone, dimethyl sulfoxide, acetonitrile, isopropanol, n-hexanol, ethylene dichloride, methylene dichloride, cydohexane, or suitable combinations thereof. The bonding surfaces can be cleaned and then wetted with the solvent. The bonding surfaces can be brought into contact with each other and bonded by being subjected to suitable pressure and temperature conditions (e.g., using a press, oven, heated plates, etc.) for a predetermined length of time.

Localized welding can involve the focused application of energy at or near the bonding surfaces to heat and soften the bonding surfaces, thereby bonding the components together. Suitable forms of energy may include ultrasonic energy, microwave energy, or infrared energy. In some instances, suitable components can be formed in one or more of the components so as to direct the applied energy to the appropriate regions of the bonding surfaces.

As another example, suitable surface modification techniques can be applied to one or more of the bonding surfaces described herein in order to achieve direct bonding. Surface modification can involve treating the bonding surfaces in order to increase the surface energies thereof, thus improving surface contact and increasing the extent of polymer chain entanglement between the bonding surfaces. In many embodiments, the bonding surfaces can be modified by plasma activation, UV exposure, and/or ozone exposure.

The parameters of the surface modification treatments described herein (e.g., treatment time) can be selected so as to optimize the extent of surface rearrangement of polymer chains at the bonding surfaces.

Alternatively or in addition, indirect bonding techniques utilizing suitable adhesives can be used to bond first and second components of an AIOL. The adhesive can be applied to at least a portion of the bonding surfaces described herein. In many embodiments, the adhesive is selected to have similar material and mechanical properties as the first and second components. For example, the adhesive may comprise a prepolymer of the polymer of the components. The prepolymer may comprise one or more of a monomer, an oligomer, a partially cured monomer, particles, and nanoparticles of the polymer, for example. Such bonding embodiments can provide advantage in that there is no or a decreased seam—the bonded interface has similar mechanical properties as the structure. For example, the adhesive may swell similarly to the first and second components. This can be helpful when the adhesive is provided circumferentially around the first and second components as described above, as such components can swell substantially along the diameter and circumference, for example. Decreasing stresses along the bonding surfaces of an AIOL can be helpful, as the AIOL can be made smaller to decrease insertion size and may comprise thin deformable structures configured to deform with decreased stresses.

In many embodiments, the adhesive (e.g., the prepolymer) is cured to bond the first and second components together. The curing process may involve the polymerization of one or more constituents of the adhesive using techniques known to one of skill in the art. For example, precursor monomers in a prepolymer may be partially or fully polymerized by the addition of an initiator. The initiator may be a photoinitiator such as Irgacure 651 (I651, Ciba-Geigy), or a radical initiator such as 2,2'-azobis(isobutyronitrile), 2,2'-azobis(2,4-dimethylvaleronitrile), dilauroyl peroxide, or bis(4-t-butylcyclohexyl)peroxydicarbonate, for example. In many embodiments, the monomers are polymerized in the presence of a crosslinking agent. The crosslinking agent may comprise one or more of EGDMA, DEGDMA, or TEGDMA. The polymerization of the monomers and crosslinking agent may form an interpenetrating polymer network (IPN), which may be entangled with the first and second components, thereby joining them together. In some instances, the bonding surfaces can be activated using suitable activating agents to provide exposed reactive groups, thereby enabling the formation of chemical bonds between the bonding surfaces and the prepolymer and/or crosslinking agent. Following the polymerization process, excess reagents can be removed by rinsing, immersion in a suitable solvent, or other methods known to those of ordinary skill in the art.

The bonding techniques described herein can be applied at any point during the fabrication of the AIOLs described herein. For example, the first and second components can be bonded to each other while in the stiff, substantially dry configuration. Each of the components can be provided in a stiff configuration for machining and bonded together with the adhesive while in a stiff configuration. The components can be subsequently hydrated. Alternatively, the components can be bonded while in a partially or fully hydrated configuration.

In many embodiments, the first and second lens components comprise a copolymer of hydroxyethyl methacrylate and methyl methacrylate. When cured, the adhesive comprises the copolymer of hydroxyethyl methacrylate and methyl methacrylate. This configuration can allow the lens to expand from a stiff less than fully hydrated configuration, to the fully hydrated configuration with substantially swelling and inhibited stress to the components and the adhesive located along the seam. The stiff, less than fully hydrated configuration of the polymer material will be understood by a person of ordinary skill in the art to comprise a polymer having a sufficiently low amount of water to provide stiffness to the polymer material of the first and second components. The less than fully hydrated configuration may comprise a substantially dry configuration composed of no more than about 5% water, for example 0.2-3% water, such that the polymer material comprises sufficient stiffness for machining the material to optical tolerances as will be readily understood by a person of ordinary skill in the art. When the AIOL is placed in the lens capsule or placed in a hydration buffer as understood by a person of ordinary skill in the art, for example, the polymer may swell to a hydrated state and gradually to a fully hydrated state. The polymer in the fully hydrated state may be composed of about 15% to 30% water, for example, depending on the material selected. The polymer in the fully hydrated state may swell by more than 10%, such as 10% to 15%.

Figure 36:
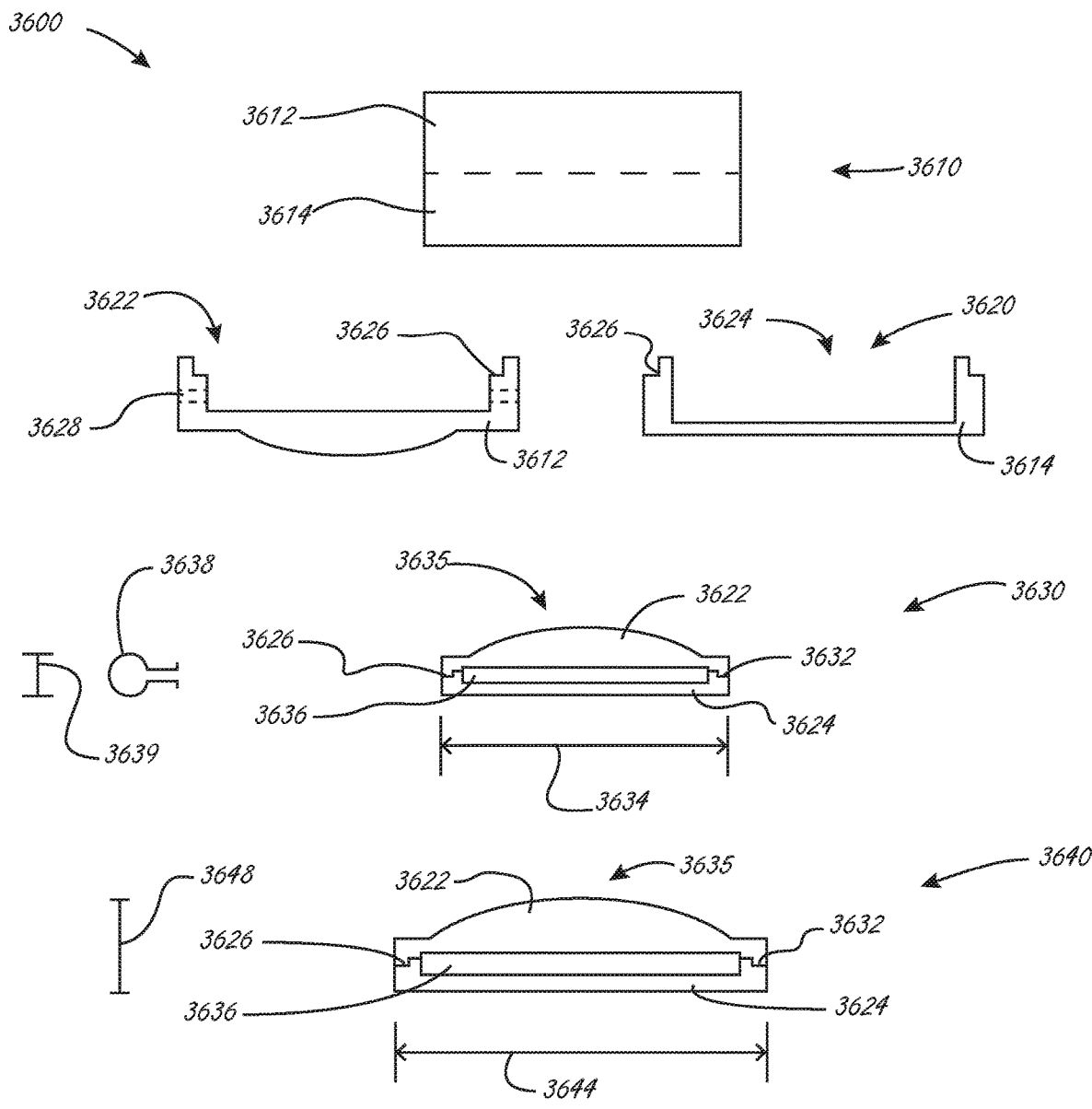
FIG. 36 shows a method of manufacturing an AIOL, in accordance with many embodiments.

FIG. 36 shows a method 3600 of manufacturing and providing an AIOL.

At a step 3610, a block of polymer material as described herein is provided. The block of material is cut into a first component 3612 and a second component 3614. The polymer material comprises a stiff configuration as described herein.

At a step 3620, the first component 3612 and the second component 3614 are shaped into first lens component 3622 and second lens component 3624 of the AIOL. The components can be shaped in one or more of many ways such as turning on a lathe, cutting, ablation, and other known methods of shaping optical lenses. Alternatively, or in combination, the components may be molded. One or more of the components 3622, 3624 comprises a feature 3626 shaped to receive the opposing component (the feature 3626 may comprise an annular groove, for example). A channel 3628 can be provided to allow fluidic communication with the chamber 3636 of the AIOL. Alternatively, or in combination, the channel 3628 can be formed when the first and second components are bonded together.

At a step 3630, the first and second components 3622, 3624 are bonded together with an adhesive 3632 provided in the feature 3626. The first component 3622 and the second component 3624 define a chamber 3636.

The adhesive 3632 comprises a prepolymer of the polymer of the components 3612 and 3614. Although the components are shown provided from a single block, the polymer material can be provided with separate blocks of material having similar polymer composition.

A haptic 3638 can be affixed to the AIOL 3635, such that an internal chamber of the IOL is fluidically coupled to the chamber of the haptic. The haptic may comprise a material similar to the AIOL, or a different material. The haptic 3638 may have a thickness 3639. For example, the AIOL may comprise an acrylate as described herein and the haptic 3638 may comprise a soft silicon material. The haptic may comprise a soft material inserted into the AIOL when the AIOL comprises a stiff configuration, for example.

The AIOL in the stiff configuration comprises a dimension 3634 across, such as a diameter. The AIOL may comprise a thickness 3648 extending between an anterior most portion of the AIOL body and the posterior most portion of the AIOL body.

At a step 3640, the AIOL 3635 is hydrated to a substantially hydrated configuration to decrease stiffness, such that the AIOL comprises a soft material. In the hydrated configuration dimensions of the AIOL increase, and may increase proportionally to each other. In many embodiments, the increase comprises a similar percentage increase along each dimension.

In many embodiments, the amount of hydration in the stiff configuration comprises a predetermined amount of hydration in order to accurately machine the lens components to an appropriate amount of refractive power when the AIOL comprises the fully hydrated state when implanted in the eye.

The disc shaped optical structure of the upper component 3622 can be flat, or lens shaped, for example. The disc shaped optical structure of the lower component 3624 can be flat, or lens shaped, for example, such that one or more of the optical structures deforms to provide optical power.

Figure 37:
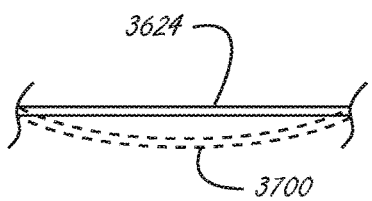
FIG. 37 shows an optical structure deformed to provide optical power.

FIG. 37 shows the optical structure deformed with a deflected surface profile in order to provide optical power with a curved spherical surface profile 3700 as described herein. The fluid of the AIOL can be greater than the index of refraction of 1.33 of the aqueous humor in order to provide the increased optical power with curved surface 3700. The optical component 3624 may comprise a substantially planar shape providing no significant optical power in a first configuration, and can be deformed to a deflected curved spherical surface profile 3700 that provides optical power for accommodation.

While reference is made to acrylates, the polymer and prepolymer may comprise silicone hydrogel materials, for example.

Figure 38A:
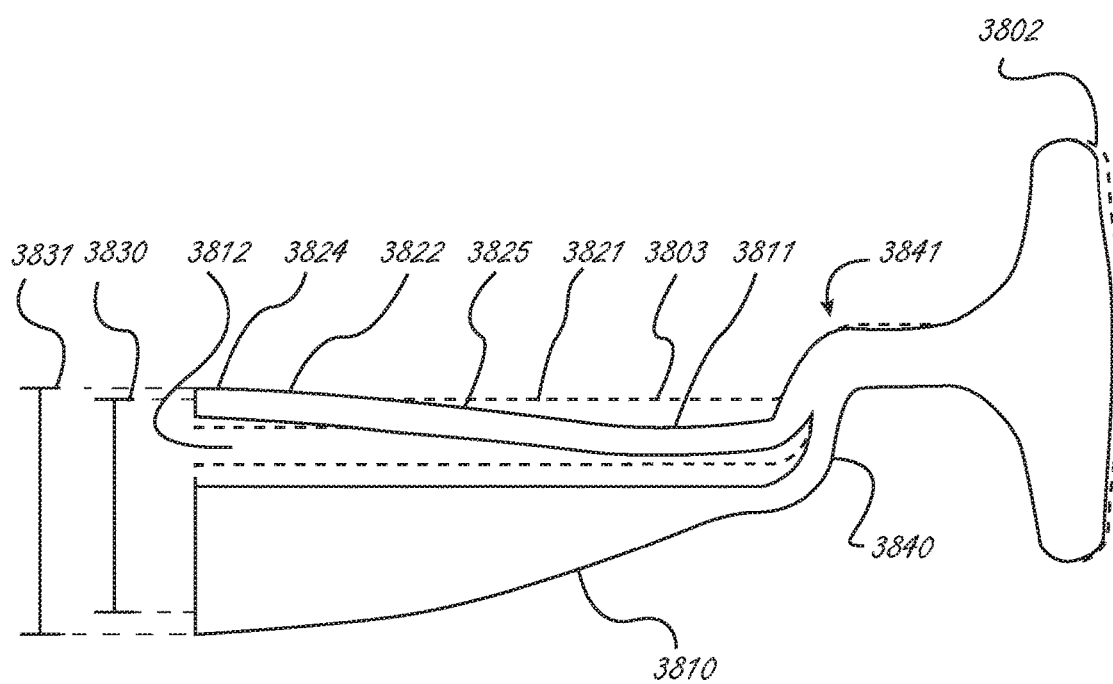
FIG. 38A shows an AIOL with an anterior-most portion of the AIOL anterior to the anterior most-portion of the haptic, in which the deflectable member of the AIOL is configured to deflect in response to translational and rotational movement of the haptic, in accordance with embodiments.

FIG. 38A shows an AIOL with an anterior-most portion of the AIOL anterior to the anterior most-portion of the haptic (both shown lower on the page), in which the deflectable member of the AIOL is configured to deflect in response to translational and rotational movement of the haptic. In alternative embodiments, the lens can be placed with an opposite anterior posterior orientation as described herein. The deflectable member 3803 comprises sufficient radial strength such that a radially inward force to an outer portion of the deflectable member causes deflection of an inner portion of the deflectable member as described herein.

The deflectable member can be configured in one or more of many ways to provide radial strength in order deflect to at least the inner portion, for example with one or more of a modulus of elasticity, a thickness, or a diameter.

The deflectable member can be coupled to the haptics in one or more of many ways so as to deflect when urged radially inward by the haptics engaging the lens capsule. In many embodiments, the deflectable member comprises sufficient radial strength to induce shape changes of at least the inner portion when the outer portion of the deflectable member is urged radially inward, or rotated, and combinations thereof. In many embodiments, the deflectable member is coupled to the lens capsule such that rotation of the haptics relative to the stiff member induces a radially inward movement and rotational deflection of an outer portion of the deflectable member. Alternatively, or in combination, the haptics can be arranged to slide radially and in relation to the stiff member in order to urge the deflectable member inward with radial force and deflect the inner portion of the deflectable member with radial strength of the outer portion. The deflectable member may comprise one or more structures on the outer portion to encourage deflection, such as a concave outer portion or thinner annular region to encourage concave deflection of the outer portion and convex deflection of the inner portion, for example.

The AIOL comprises undeflected configuration 3821 for far vision and deflected configuration 3822 for near vision. The AIOL is depicted in a non-accommodating configuration with a planar configuration anterior planar deflectable member 3803 coupled to lever haptic structure 3802. An outer structure of haptic 3802 is configured to engage the lens capsule, and may comprise structures to reduce pressure on the capsule as described herein. A stiff member 3810 may comprise a lens to provide optical power for far vision. The deflectable member 3803 may comprise a substantially planar member having a substantially constant thickness, for example. The deflectable member 3803 comprises an inner optical portion 3825 and an extension 3811. Extension 3811 extends between the inner optical portion 3825 and the translating and rotating haptic structure 3802. When the inner optical portion 3825 comprises the convex deflection 3824, the fluid of the chamber beneath the inner optical portion is shaped to provide an optical correction for near vision.

The deflectable member 3803 and stiff member 3810 define at least a portion of an inner chamber 3812 as described herein.

The AIOL comprises a central thickness extending from an outer surface of the stiff member 3810 to an outer surface of the deflectable member 3803. The central thickness may comprise a first central thickness 3830 of the lens in a far vision configuration, and a second central thickness 3831 of the lens in a near vision configuration. The increase in thickness of the lens centrally is related to the increased optical power of the lens. The increased optical power of the lens is also approximately inversely related to a square of the diameter of the central optical portion. The extension portion can decrease the diameter of the optical portion and provide increased optical power for an amount of change between first distance 3830 and second distance 3831.

The stiff member 3810 is connected to haptic structure 3802, such that the haptic structure 3802 rotates when the lens accommodates for near vision. The haptic structure 3802 extends to a first anchor region such as an anchor point 3840 about which the haptic translates and rotates relative to the stiff member 3810. The haptic structure extends a distance from the first anchor region to the wall of the lens capsule. The haptic structure 3802 extends to a second anchor region such as second anchor point 3841. The second anchor region 3841 couples to the deflectable member 3803 in order to induce inward force on the deflectable member. The distance from the first region to the outer structure of the haptic engaging the lens capsule is greater than the distance from the first region to the second region. In at least some embodiments, this difference in distance can provide at least some mechanical leverage of the lens capsule forces on the deflectable member 3803. The radial force of the lens capsule on the deflectable member 3803 induces a convex deflection 3824 of the deflectable membrane. The extension 3811 comprises an opposite concave curvature.

The components of the AIOL such as the stiff member, the deflectable member, and the one or more haptics may comprise the same polymer as described herein. These components can have varying amounts of softness and stiffness depending on the thickness, for example. In many embodiments the haptic comprises a thickness so as to reversibly deform at least partially when urging the deflectable member radially inward with one or more of rotation or translation in response to radially inward force from the lens capsule.

Figure 38B:
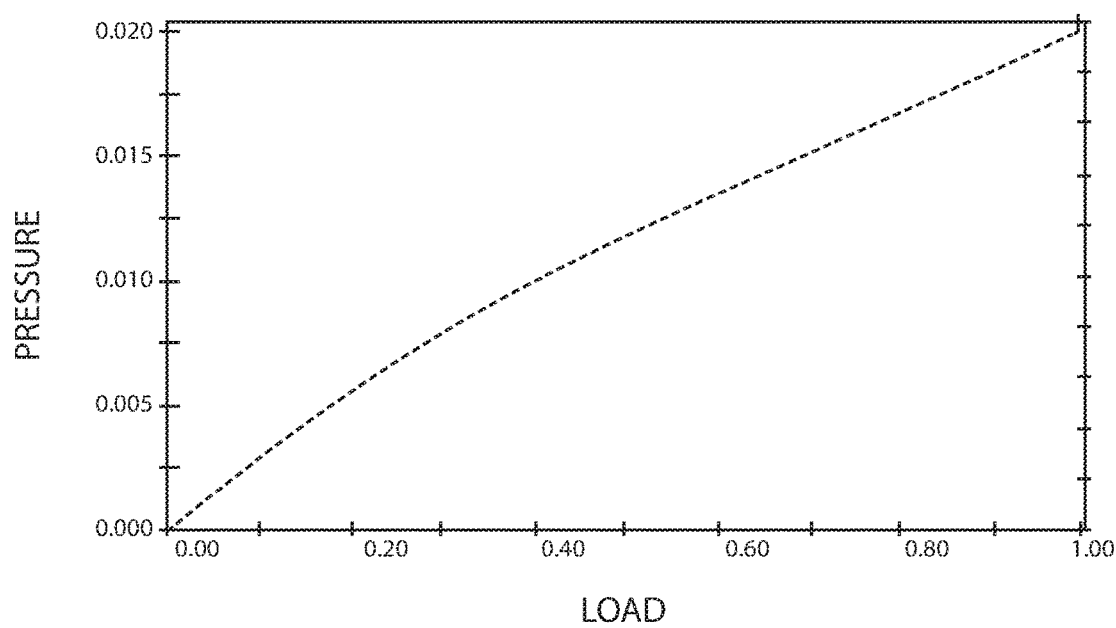
FIG. 38B shows internal chamber pressure in response to loading of the AIOL as in FIG. 38A.

FIG. 38B shows internal chamber pressure in response to loading of the AIOL as in FIG. 38A. The internal pressure of the AIOL increases approximately linearly with the load of the AIOL. The combination of internal pressure and radially inward force can deflect the member 3803 to provide optical power when the eye accommodates as described herein. The load modeled was normalized with respect to one or more published maximum load values corresponding to force of lens capsule on the AIOL, which can be readily determined by a person of ordinary skill in the art based on published data. The material properties of the AIOL as modeled herein can be readily determined based on published data for the materials as described herein.

Figure 39A:
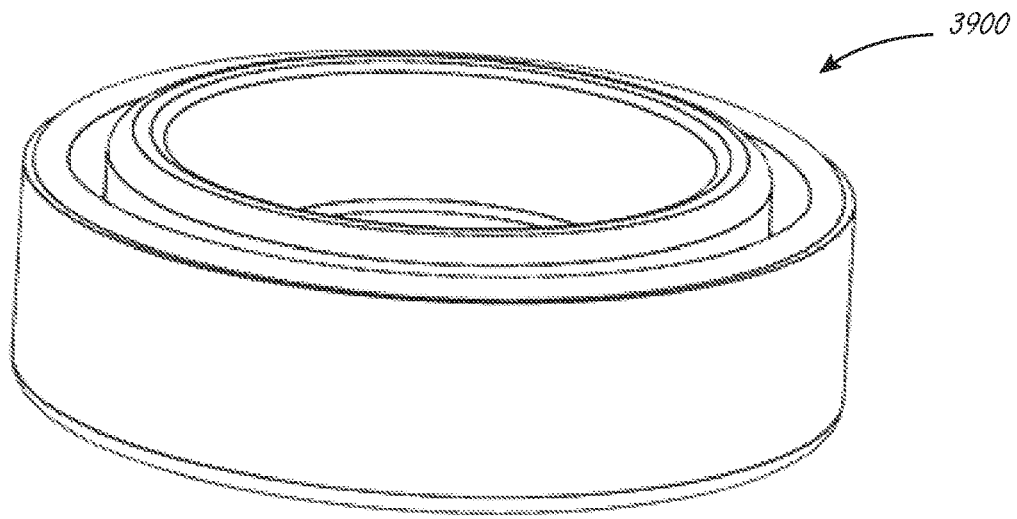
FIG. 39A shows a perspective view of an intraocular lens, in accordance with embodiments.

FIG. 39A shows an accommodating intraocular lens 3900. The intraocular lens 3900 may comprise a central lens region 3904 and a peripheral bellows region 3903 with two bellows 3903a, 3903b. The intraocular lens 3900 may be manufactured in two components, a top half 3900a and a bottom half 3900b. The material used may be compliant, as for example a hydrophilic acrylic or a hydrogel. Other materials can be used Alternatively, or in combination. The two halves 3900a, 3900b can be assembled as shown in the FIG. 39B by gluing the top half 3900a to the bottom half 3900b at joint 3901. The cavity 3905 between the two halves 3900a, 3900b may be filled with a high refractive index fluid, causing the intraocular lens 3900 to function as a lens.

A function of the double bellows feature 3903 may be to increase the response of the intraocular lens 3900. The outermost part 3903c of the bellows 3903 may interact with the capsular bag of the eye. When the bag exerts pressure on the bellows 3903, fluid may be displaced from the bellows region 3903 into the central lens cavity. The increased pressure may cause the top lens part 3900a to deform upwards, changing its radius of curvature and therefore produce power change and accommodation. The innermost bellows 3903a may be adapted so that its outermost wall may be very compliant. Any pressure exerted from the innermost wall of the outermost bellows 3903b may be translated in fluid displacement out of the innermost bellows 3903a cavity. In this fashion, if there is an increase in stiffness due to the glue line along the outermost bellows 3903, the deformation may still be allowed to occur in the innermost bellows 3903a.

Figure 39B:
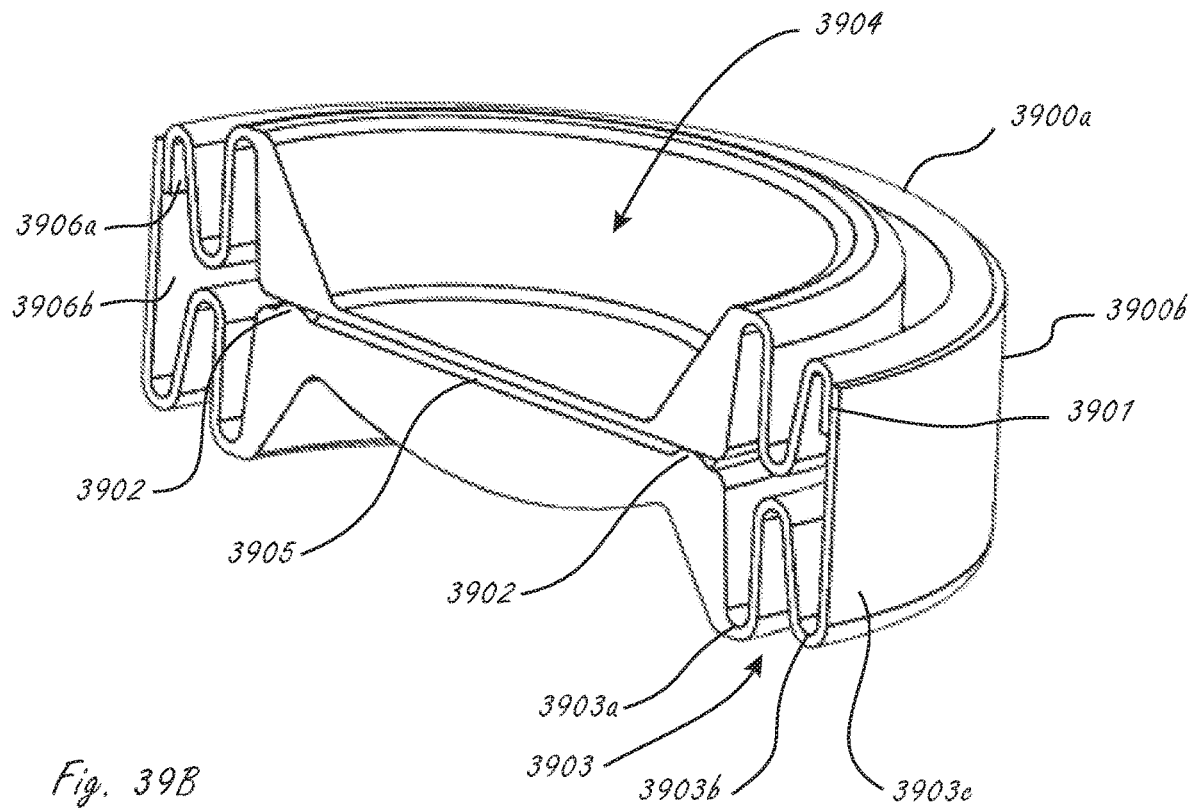
FIG. 39B shows a cross-sectional view of the intraocular lens of FIG. 39A, in accordance with embodiments.

A line of discrete protrusions, or bumps 3902, may be built on the inner surface 3906b of the bottom half 3900b as shown in FIG. 39B, or alternatively the inner surface 3906a of the top half 3900a. The bumps 3902 may serve to preserve the gap between the two halves thereby facilitating fabrication.

Any of the features of the intraocular lens 3900 may be combined with any of the features of the other intraocular lenses described herein any vice versa.

Figure 40A:
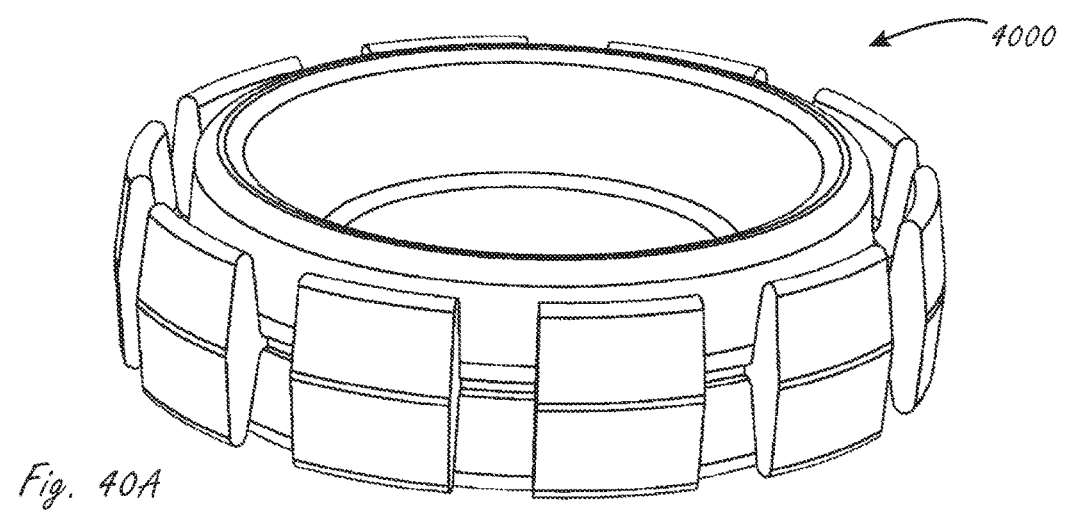
FIG. 40A shows a perspective view of an intraocular lens, in accordance with embodiments.
Figure 40B:
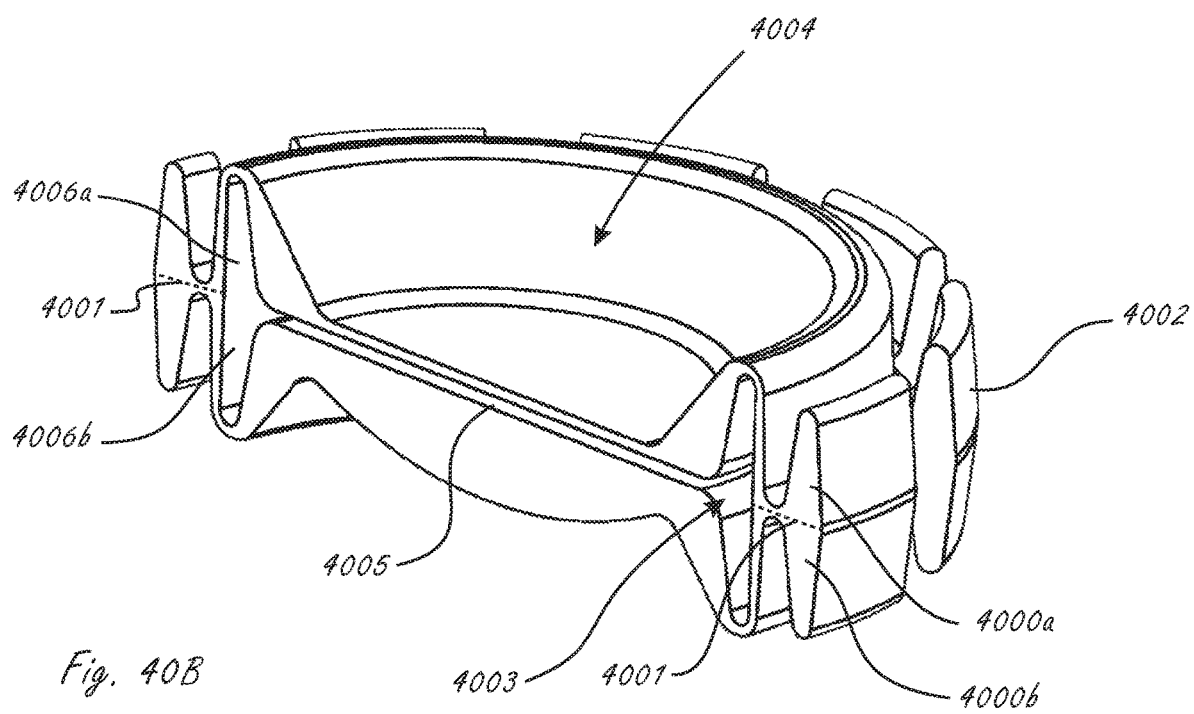
FIG. 40B shows a cross-sectional view of the intraocular lens of FIG. 40A, in accordance with embodiments.

FIGS. 40A and 40B show an accommodating intraocular lens 4000. The intraocular lens 4000 may comprise a central lens region 4004 and a peripheral bellows region 4003. The intraocular lens 4000 may be manufactured in two components, a top half 4000a and a bottom half 4000b. The material used may be compliant, as for example a hydrophilic acrylic or a hydrogel. Other materials can be used Alternatively, or in combination. The two halves 4000a, 4000b may be assembled as shown in FIG. 40B by gluing the top half 4000a to the bottom half 4000b at joint 4001. The cavity 4005 between the two halves 4000a, 4000b may be filled with a high refractive index fluid, causing the intraocular lens 4000 to function as a lens.

A series of discrete paddles 4002 may be built alongside the outermost wall of the bellows 4003. When the bag exerts pressure on the paddles 4002, the paddles 4002 may transfer the forces to the outermost wall of the bellows 4003, causing said wall to deform radially inwards. In such manner, fluid may be displaced from the bellows region 4003 into the central lens cavity 4005. The paddles 4002 may not be continuous along the circumferential periphery of the intraocular lens 4000 as shown in FIG. 40A to reduce the circumferential and therefore radial stiffness of the assembly or lens 4000.

The displaced fluid may cause an increase in pressure and this pressure increase may causes the top lens part 4000a to deform upwards, changing its radius of curvature and therefore produce power change and accommodation. Similarly to the intraocular lens 3900, a line of discrete protrusions, or bumps, could be built on the inner surface 4006b of the bottom half 4000b as shown in FIG. 39B, or alternatively the inner surface 4006a of the top half 4000a. The bumps may serve to preserve the gap between the two halves 4000a, 4000b thereby facilitating fabrication.

Any of the features of the intraocular lens 4000 may be combined with any of the features of the other intraocular lenses described herein and vice versa.

Figure 41A:
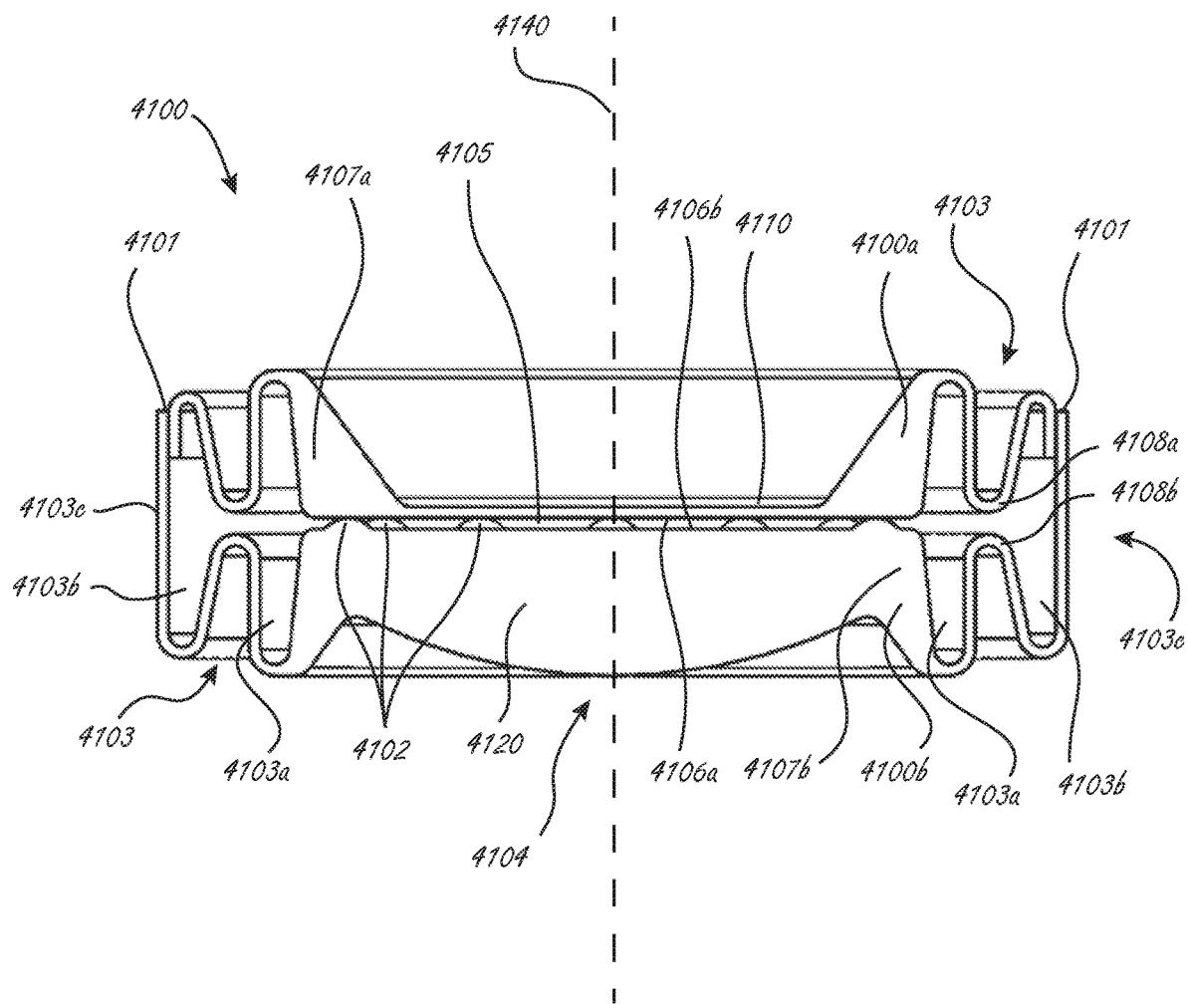
FIG. 41A shows a cross-sectional view of an accommodating intraocular lens, in accordance with embodiments.

FIG. 41A shows an accommodating intraocular lens 4100. An optical axis 4140 extends through the central lens region 4104. The intraocular lens 4100 may comprise a central lens region 4104 and a peripheral bellows region 4103 with two bellows, for example. An annularly-shaped stiff coupling structure can extend circumferentially around the central lens region 4104 comprising the optical axis. The annularly-shaped stiff coupling structure may comprise a first annularly-shaped stiff coupling structure 4107a located on the first component, and a second annularly-shaped stiff coupling structure 4107b located on the second component.

The two bellows may comprise an inner continuous bellow 4103a and an outer continuous bellow 4103b in fluid communication with one another. In many embodiments the bellows comprise one or more folds. The folds of the bellows have the advantage of decreasing resistance to the capsular bag as the capsular bag urges inward, and allowing the bellows to move radially outward as the capsular bag expands. The folds may also provide a very gentle outward force against the capsular bag to improve coupling with the capsular bag. A person of ordinary skill in the art can use biometry such as optical coherence tomography to size the bellows region to the capsular bag. The bellows region 4103 may comprise a first fold 4108a on the first component and a second fold 4108b on the second component. The first fold 4108a and the second fold 4108b can extend inwardly and toward each other in a direction similar to the optical axis. The first fold and the second fold can extend continuously and circumferentially around the optical axis, for example for 360 degrees around the optical axis. This arrangement of the folds can provide coupling of the lens to the lens capsule with deflection of the folds.

The bellows region can be configured in many ways and comprises one or more folds to allow the outer reservoir to couple to the inner chamber. While two circumferentially extending bellows with a fold extending therebetween are shown, different numbers of bellows such as three or more bellows may be provided, for example. The bellows 4103a, 4103b may be continuous along the periphery of the central lens region 4104. The bellows 4103a, 4103b may be annular, elliptical, or rotationally symmetric in shape. Fluid may be present within the continuous inner volumes of the bellows 4103a, 4103b. The inner bellow 4103a may be in fluid communication with the central lens region 4104.

The stiff coupling structure can be configured in many ways to inhibit radially inward movement or forces from the bellows region to the central lens region 4104 when the lens capsule urges against the bellows region and transfers fluid from the bellows region into the central lens region 4104. The stiff coupling structures similarly inhibit radially outward movement of the central lens region 4104 when the bellows region moves radially outward in response to decreased force of the lens capsule. The first annularly-shaped stiff coupling structure 4107a may comprises a first radial thickness greater than a first thickness of the first bellows region 4103a, and the second annularly-shaped structure 4107b may comprise a second radial thickness greater than the second thickness of the second bellows region 4103b. Although the stiff coupling structure can be relatively stiff compared with other structures of the lens such as the folds, the stiff coupling structure can be configured to be one or more of rolled, folded, or compressed for insertion through a small incision in the eye, for example. The intraocular lens 4100 may be manufactured in many ways, for example with one or more of lathe turning to shape one or more components, molding to form one or more components, or direct fabrication to form one or more component. Alternatively, or in combination, the components can be manufactured with direct fabrication based on a computer model of the lens. The lens components can be fabricated separately or together with direct fabrication. The lens can be fabricated directly as a single piece lens comprising the components described herein.

In many embodiments, the intraocular lens is manufactured in two component pieces, a top component 4100a and a bottom component 4100b. The material used may be compliant, as for example a hydrophilic acrylic or a hydrogel. Other materials can be used Alternatively, or in combination. The two components 4100a, 4100b can be assembled as shown in the FIG. 41A by bonding the top component 4100a to the bottom component 4100b at joint 4101. The cavity 4105 between the two components 4100a, 4100b may be filled with a high refractive index fluid, providing a deformable fluid space within the intraocular lens 4100 that function as a lens with a variable optical power.

The peripheral bellows region 4103 may comprise a continuous fluid reservoir or chamber defined by a plurality of folds of the top component 4100a and bottom component 4100b, with the folds defining the inner bellow 4103a and outer bellow 4103b. The top and bottom components 4100a, 4100b may be folded inward between the inner and outer bellows 4103a, 4103b to define a compliant region between the inner and outer bellows 4103a, 4103b. This compliant region may define one or more fluid channels between the inner and outer bellows 4103a, 4103b. The fluid channel(s) may be annular, peripheral, or rotationally symmetric in shape much like the inner and outer bellows 4103a, 4103b. In the anterior-posterior direction, this compliant region may be thinner than the inner and outer bellows 4103a, 4103b.

Figure 41B:
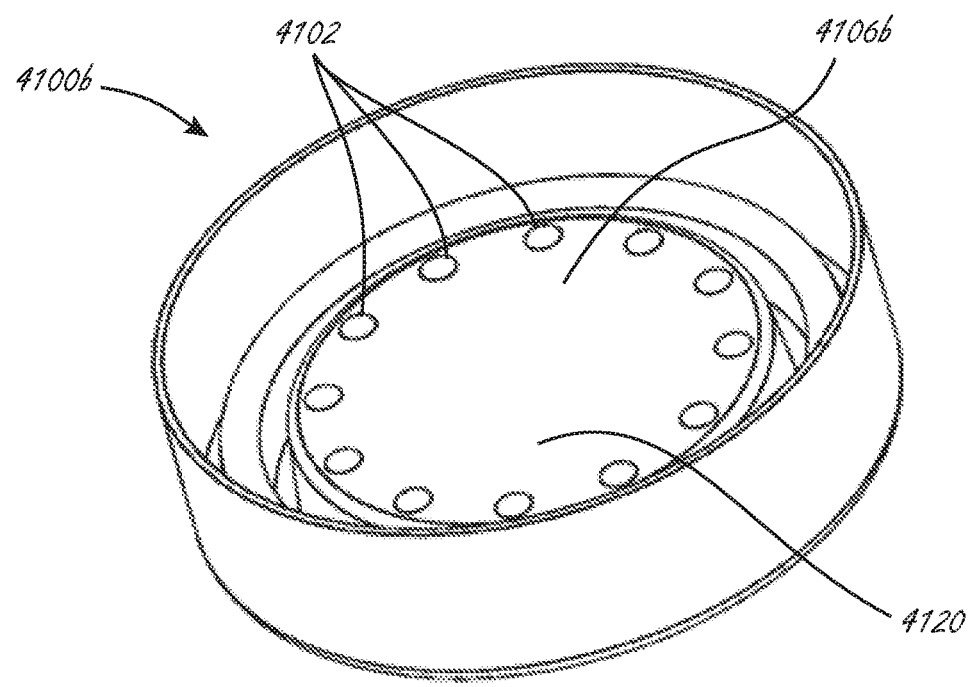
FIG. 41B shows a perspective view of a lens component of the intraocular lens of FIG. 41A.
Figure 41C:
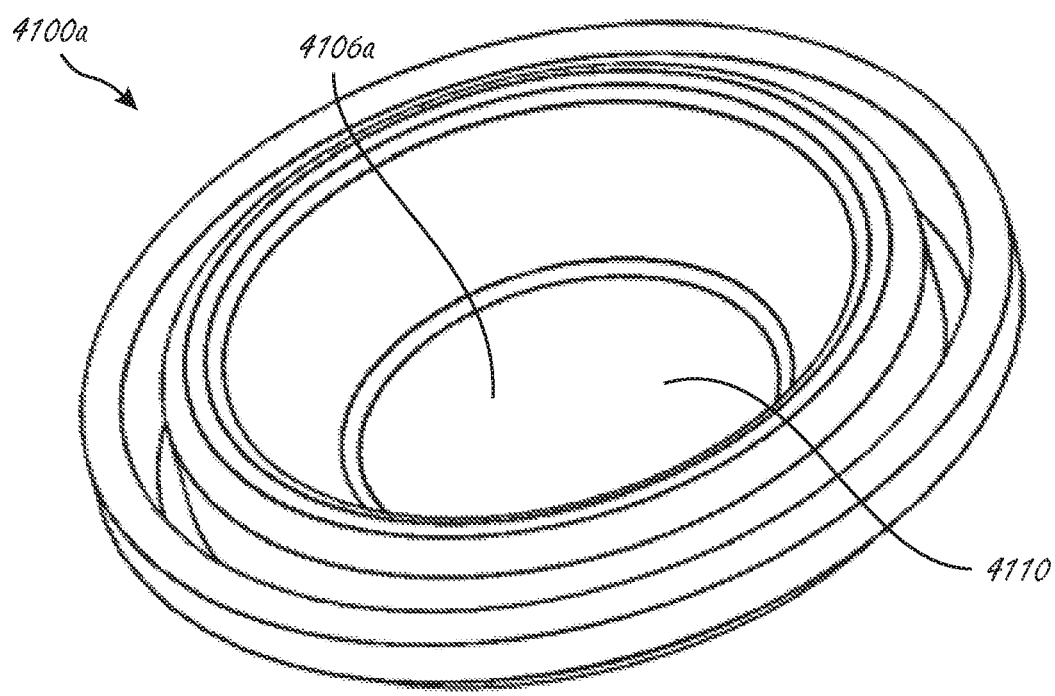
FIG. 41C shows a perspective view of the opposite lens component of the intraocular lens of FIG. 41A.

The top component 4100a may comprise a deflectable, planar member 4110 (FIG. 41C) and the bottom component 4100a may comprise a piano-convex member 4120 which may provide optical power (FIG. 41B). Alternatively, the bottom component 4100a may comprise a planar member providing substantially no optical power; and, the top component 4100b may be pre-curved (or in the form of a shell) to provide a shape to the cavity 4105 which may be filled with a refractive fluid to provide the optical power. When placed in the lens capsule, the top component 4100a may be in the anterior position and the bottom component 4100b may be in the posterior position. Alternatively, the top component 4100a may be in the posterior position and the bottom component 4100b may be in the anterior position.

A function of the double fold in the multiple bellows feature 4103 may be to increase the mechanical response of the intraocular lens 4100. The outermost part 4103c of the bellows 4103 may interact with the capsular bag of the eye. When the bag exerts pressure on the bellows 4103, fluid may be displaced from the bellows region 4103 into the central lens cavity 4105. The increased pressure and volume of fluid in the central lens cavity 4105 will typically cause the top lens part 4100a to deform upwards and change its radius of curvature and therefore produce power change and accommodation. For instance, the planar member 4110 may deflect upward and experience a decrease in radius of curvature. Alternatively, or in combination, a separation distance between the two components 4100a, 4100b increases in response to the increased pressure to change the optical power (i.e., the regions of the components 4100a, 4100b which define the periphery of central lens region 4104 may separate in the anterior-posterior direction). The innermost bellows 4103a may be adapted so that its outermost wall may be very compliant. A pressure exerted from the innermost wall of the outermost bellows 4103b resulting from forces applied to the outermost fold in the bellows may be translated in fluid displacement out of the innermost bellows 4103a cavity. In this fashion, if there is an increase in stiffness due to the bonding line along the outermost bellows 4103, the deformation may still be allowed to occur in the innermost bellows 4103a.

The bellows region 4103 can be rotationally symmetric about an optical axis of the lens region in order to facilitate manufacturing. The rotationally symmetric structures of the bellow can be readily turned on a lathe, or formed from a mold that can be readily lathed.

A plurality of protrusions, or bumps or posts 4102, may be radially disposed on the inner surface 4106b of the bottom component 4100b as shown in FIG. 41A and FIG. 41B, or alternatively the inner surface 4106a of the top component 4100a, and combinations thereof, for example. The bumps or posts 4102 may serve to preserve the gap between the two components thereby facilitating fabrication. In some embodiments, the bumps or posts 4102 may be bonded to the other component of the intraocular lens 4100 after the top and bottom components 4100a, 4100b are brought together. The space between adjacent bumps or posts 4102 may serve as conduits for fluid between the bellows 4103 and the cavity 4105. In some embodiments, the bumps or posts 4102 may be free from the other component of the intraocular lens 4100 to minimize non-symmetric deformation of opposing planar member. In some embodiments, the planar member opposing the bumps or posts 4102 may comprise an outer annular region in contact with the bumps or posts 4102 and a deflectable, inner circular region raised and separated from the outer annular region and the bumps or posts 4102.

The top and bottom portions 4100a, 4100b comprising the top and bottom components can be formed in many ways. For example, the top and bottom portions 4100a, 4100b can be formed by turning each portion on a lathe or by molding, for example. In many embodiments, the top and bottom portions each comprise rotationally symmetric structures such as the bellow and other components as described herein. The protrusions can be formed in many ways. The rotationally symmetric components can be bonded together to form the lens as disclosed herein.

The bellows 4103a, 4103b as disclosed herein can provide improved coupling of the fluid reservoir with the lens capsule of the eye. The folded structures of the bellows 4103a, 4103b can provide a resilient spring function to the reservoir such that the reservoir can urge gently against the lens capsule and allow the lens capsule to move inward to transfer fluid from the reservoir to the inner lens structure to provide optical power.

The protrusions 4102 can be formed in many ways to provide fluid transfer and separation of the anterior and posterior lens components 4100a, 4100b. For example, the protrusions 4102 can provide discrete protrusions, bumps, or posts. Alternatively, the protrusions 4102 may comprise portions of an annular structure such as a rim. The rim may have channels cut at least partially into the rim in order to allow fluid transfer. The plurality of protrusions can be separated from each other to define a plurality of channels 4107 defined by the plurality of protrusions in order to fluidically couple the chamber to the reservoir.

The protrusions 4102 can be located away from the optically used portion of the lens 4100 in order to inhibit optical aberrations and artifacts.

Any of the features of the intraocular lens 4100 may be combined with any of the features of the other intraocular lenses described herein any vice versa.

Figure 42:
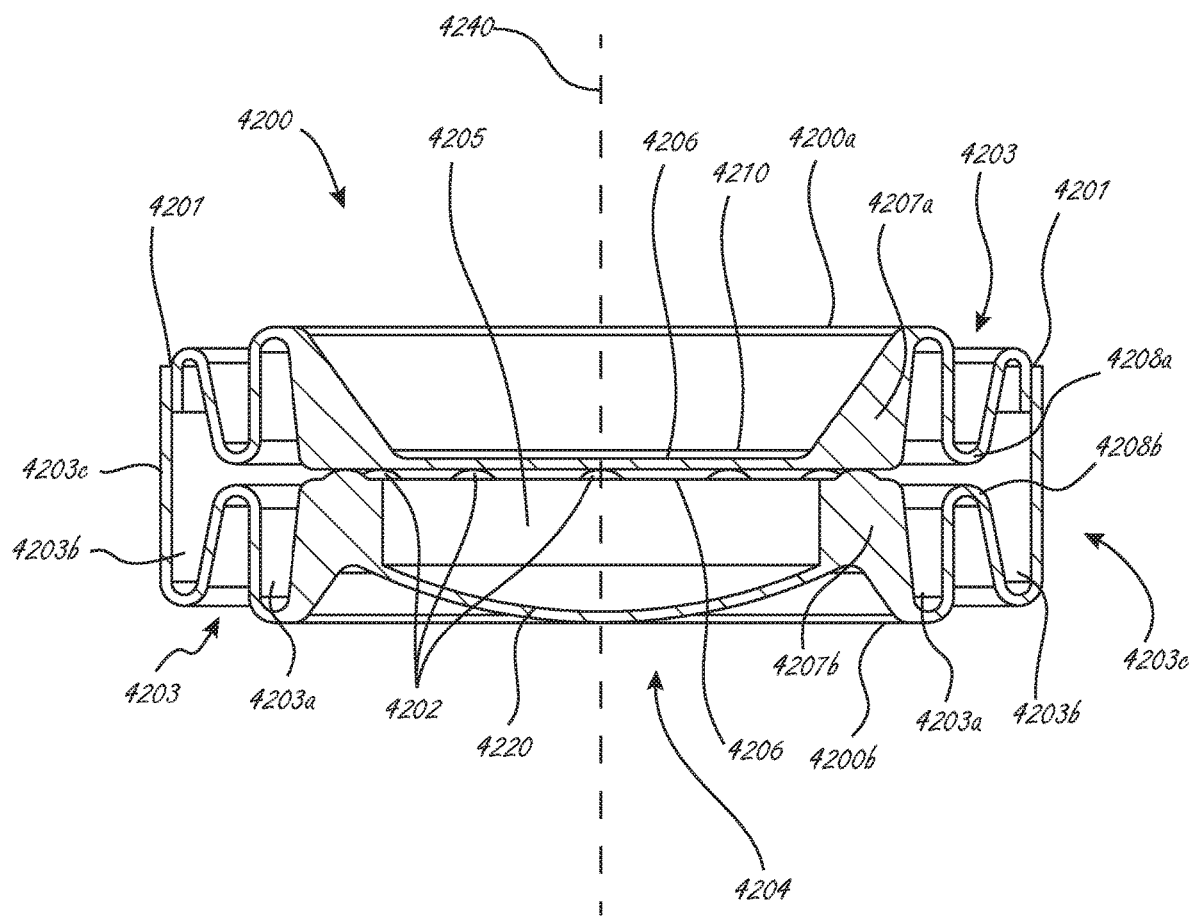
FIG. 42 shows a cross-sectional view of an intraocular lens, in accordance with embodiments.

FIG. 42 shows a cross-sectional view of an accommodating intraocular lens 4200, the embodiment of which comprises structures similar to accommodating intraocular lens 4100. First component 4200a may comprise a deflectable, planar member 4210 and second component 4200b may comprise a shell member 4220 bounding an optical gel or fluid which may provide optical power. First component 4200a and second component 4200b are affixed at seam 4201. A plurality of protrusions 4202 may be radially disposed on the inner surface 4206 and may serve to preserve the gap between the two components thereby facilitating fabrication. Protrusions 4202 can define a plurality of channels 4207 to fluidically couple the chamber to the bellows.

Accommodating intraocular lens 4200 is configured such that the chamber 4205 extends into the second component. The second component can comprise decreased amounts of solid material as compared with lens 4100, which can facilitate folding, rolling, or compressing lens 4200 into a smaller cross-section in order to configure the lens with a narrow insertion profile in order to fit within a narrow incision of the eye.

Optical axis 4240 extends through the central lens region 4204 of accommodating lens system 4200; first component coupling structure 4207a and second component coupling structure 4207b extend circumferentially around the central lens region 4204 comprising the optical axis. Multiple bellows feature 4203 illustrates a double fold bellows configuration comprising innermost bellows 4203a, outer bellows 4203b, and outermost bellows region 4203c. Bellows feature 4203 may comprise a first fold 4208a on the first component and a second fold 4208b on the second component.

Figure 43:
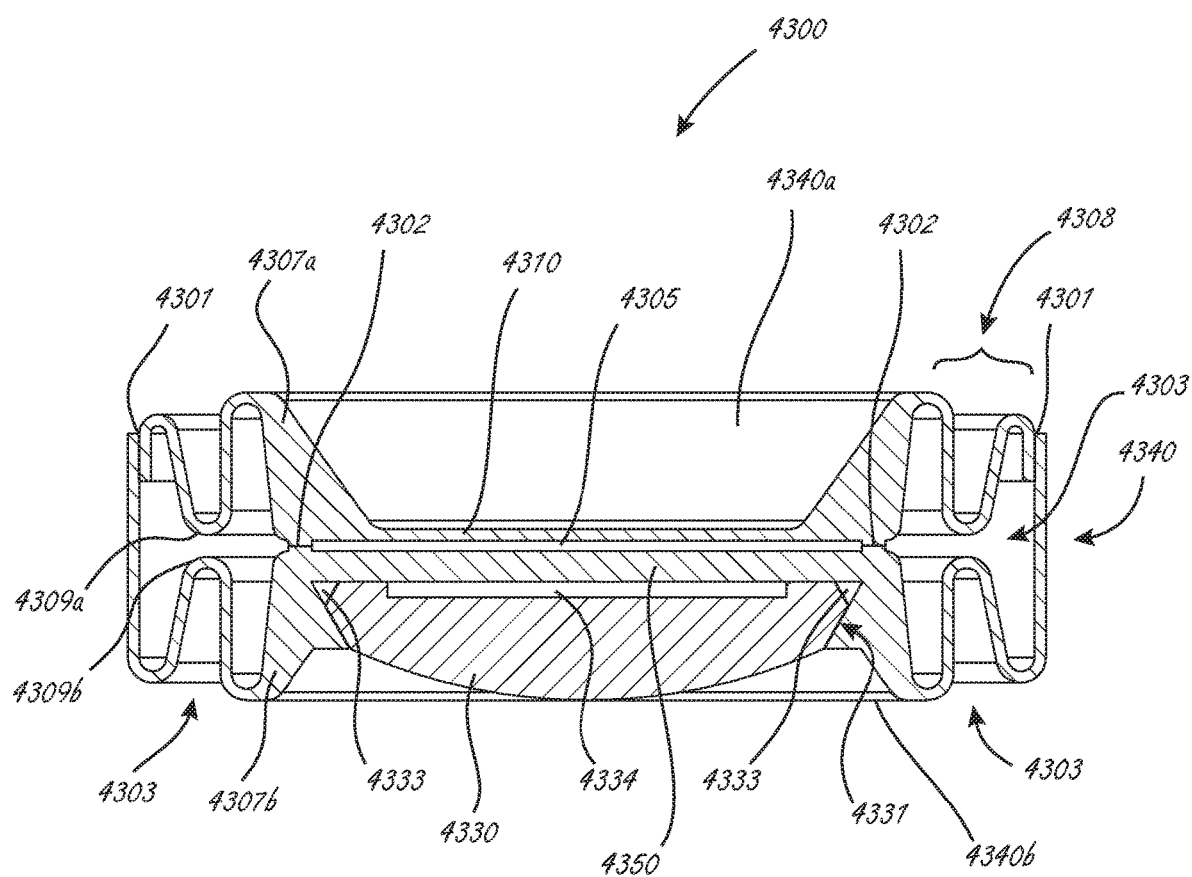
FIG. 43 shows a cross-sectional view of a fluid filled accommodating lens system comprising a bellows structure in accordance with embodiments.

Any of the features of the intraocular lens 4200 may be combined with any of the features of the other intraocular lenses described herein and vice versa FIG. 43 illustrates an AIOL system 4300 comprising a fixed lens 4330 (e.g., a fixed-power lens) and an accommodating lens unit having a fluid-filled structure 4340. The fluid-filled structure 4340 is related to the structure of AIOL 4200 in operation, but the fluid-filled structure 4340 may have negative base power, no base power or positive base power associated with the structural elements when the AIOL system 4300 is in a relaxed condition (e.g., a state in which external pressure is not applied to the bellows structure 4303). The fluid-filled structure 4340 may include a first component 4340a (e.g., a first structural element) and a second component 4340b (e.g., a second structural element) affixed to one another at a seam or joint 4301 using, for example, a glue or bonding agent as described previously herein. The joint 4301 may be substantially similar to any of the joints or seams described previously herein. For example, the joint 4301 may extend circumferentially around the first component 4340a and the second component 4340b. The first component 4340a and/or the second component 4340b can have protrusions 4302 (also referred to herein as posts) located on the inner surface of one or more of the first component 4340a and the second component 4340b, and the first and second components 4340a and 4340b can optionally be affixed to one another at the protrusions 4302 as well as the joint 4301. Alternatively, or in combination, the protrusions 4302 may be located on a first stiff coupling structure 4307a of the first component 4340a and/or a second stiff coupling member 4307b of the second component 4340b. The protrusions 4302 may, for example, provide a gap between the first component 4340a and the second component 4340b to separate the first and second components 4340a, 4340b as previously described herein.

The fluid-filled structure 4340 may include a chamber 4305 and an outer portion 4308 defining, at least in part, a fluid reservoir 4303 that extends at least partially around the chamber 4305. The fluid reservoir 4303 may comprise a continuous baffle structure disposed about a periphery of the fluid chamber 4305. The fluid reservoir 4303, for example, can define a bellows region. The continuous structure of the fluid reservoir 4303 may have an annular, elliptical, and/or rotationally symmetric shape as previously described herein. In other embodiments, the outer portion 4308 of the fluid-filled structure 4340 may be rotationally asymmetric with respect to the optical axis of the AIOL 4300. The fluid reservoir 4303 may comprise a haptic structure to engage the lens capsule as previously described herein.

The fluid-filled structure 4340 may contain an optical fluid of relatively high refractive index in the fluid reservoir 4303 and the chamber 4305. The chamber 4305 and the fluid reservoir 4303 are in fluid communication with each other such that the optical fluid can flow between the fluid reservoir 4303 and the chamber 4305 in response to forces exerted on the fluid reservoir 4303. In the embodiment illustrated in FIG. 43, the fluid reservoir 4303 is more specifically the volume between an inner surface of an outer region of the first component 4340a and an inner surface of an outer region of the second component 4340b as previously described herein. The fluid reservoir 4303 may comprise one or more folds 4309a, 4309b that extend continuously circumferentially around an optical axis of one or more of the first and second components 4340a, 4340b as previously described herein, and the folds 4309a, 4309b may extend towards each other such that the fluid reservoir 4303 comprises a plurality of bellows including an inner bellows and an outer bellows. The fluid reservoir 4303 may comprise a compliant fold region between inner and outer bellows of the plurality of bellows as previously described herein.

The chamber 4305 may be defined between an inner surface of a first optical component 4310 defined be the inner region of the first component 4340*a* and an inner surface of a second optical component 4350 defined by an inner region of the second component 4340*b*. The first and second optical components 4310 and 4350, respectively, can be surrounded by the fluid reservoir 4303. In the embodiment illustrated in FIG. 43, the fluid reservoir 4303 extends continuously circumferentially around the first and second optical components 4310 and 4350. Additionally, in the embodiment of the AIOL system 4300 illustrated in FIG. 43, the protrusions 4302 are disposed between the optical components 4310, 4350 and the fluid reservoir 4303 to define a plurality of fluid channels or conduits between the chamber 4305 and the fluid reservoir 4303 as previously described herein. The fluid reservoir 4303 and the chamber 4305 are accordingly in fluid communication with each other to change the optical power of the AIOL in response to shape changes of the lens capsule as previously described herein.

The first stiff coupling region 4307*a* and the second stiff coupling region 4307*b* may be configured to inhibit radial movement of the optical components 4310 and 4350 with respect to the outer regions as previously described herein. The first and second coupling regions 4307*a-b* accordingly maintain the optical integrity of the optical components 4310, 4350 while forces are exerted against the fluid reservoir 4303 (e.g., the outer circumferences of the optical components 4310, 4350 are maintained within desired operational dimensions).

The second component 4340*b* may further comprise an interfacing feature 4331 (e.g., coupling feature), such as a releasable locking feature or capture feature, which can capture (e.g., hold) the fixed lens 4330 such that the fixed lens 4330 may be coupled to the second component 4340*b* as illustrated. Alternatively, the fixed lens 4330 may be coupled to the first component 4340*a* instead of the second component 4340*b*. The periphery of the fixed lens 4330 is configured to be within a periphery of the first component 4340*a* and/or the second component 4340*b*. The fixed lens 4330 is configured to snap-fit onto the first or second components 4340*a*, 4340*b*, and in several embodiments the fixed lens 4330 is configured to be releasably attached to either the first component 4340*a* or the second component 4340*b*.

Moreover, the fixed lens 4330 and the first component 4340*a* and/or the second component 4340*b* may be configured such that the fixed lens 4330 may be releasably coupled to the first or second components 4340*a*, 4340*b* in situ within an eye of a patient, such as within a native lens capsule of the eye after the assembled fluid-filled structure 4340 has been placed in the native lens capsule of the eye. When the second component 4340*b* is the anterior component, this enables the fixed lens 4330 to be removed from the accommodating lens unit and replaced by another fixed lens 4330 in situ. This feature allows the fixed optical power of the AIOL 4300 to be changed (e.g., adjusted) after the accommodating lens unit has been placed in the native lens capsule and without removing the accommodating lens unit from the native lens capsule. The interfacing feature 4331 and/or the fixed lens 4330 may be configured such that channels exist to allow body fluids to freely communicate with relief spaces 4334 and 4333.

The fixed lens 4330 may, for example, have an inner surface facing and adjacent to an outer surface of the first optical component 4310 or the outer surface of the second optical component 4350 of the first or second components 4340*a*, 4340*b*, respectively, to which the fixed lens 4330 is coupled. The fixed lens 4330 may for example define a third component of the AIOL system 4300. The fixed lens 4330 may have an optical power.

The optical components 4310 and/or 4350 of the first and/or second components 4340*a*, 4340*b*, respectively, may comprise a planar member. The optical components 4310 and/or 4350 may be biased to be in a configuration that provides no optical power. For example, the first optical component 4310 may comprise a deflectable member configured to deflect from a planar shape in a neutral pressure state to a curved shape in response to fluid transfer between the fluid chamber 4305 and the fluid reservoir 4303. When the fluid reservoir 4303 is compressed and fluid is forced into chamber 4305, the first optical component 4310 deflects upwards from the planar shape in the neutral state shown in FIG. 43 to an accommodating configuration in which the first optical component 4310 is curved (i.e., convex relative to the second optical component 4350). In the accommodating configuration, the fluid in the chamber 4305 and the first optical component 4310 impart an optical power that changes dynamically based on the compression of the fluid reservoir 4303. Deflection of the first optical component 4310 may change the dimensions and/or shape of the fluid chamber 4305 as previously described herein, such as a change in a separation distance between inner surfaces of the optical components 4310 and 4350, which results in a change in the radius of curvature of the first optical component 4310. The optical power provided by the fluid in the chamber 4305 in combination with the shape of the first optical component 4310 may, for example, effectuate a portion of the optical power change of the AIOL system 4300. The second optical component 4350 may have a larger cross-section (e.g., thickness) than the first optical component 4310 such that the second optical component 4350 deforms less than first optical component 4310 or even not at all. To the extent that the second optical component 4350 deforms, the extent of the deformation of second optical component 4350 may be accommodated by the depth of the relief 4334 space between the second lens component 4340*b* and the fixed lens 4330. In several embodiments, the depth of the relief space 4334 is such that the solid surfaces in the optical field may never touch each other.

One or more of the optical components 4310 and/or 4350 may comprise a shell, such as a non-planar shell, as previously described herein. The first component 4340*a* may comprise an anterior component, and the second component 4340*b* may comprise a posterior component as previously described herein. Alternatively, the first component 4340*a* can define a posterior component, and the second component 4340*b* can define an anterior component.

Though the optical components 4310 and 4350 are showing in FIG. 43 as planar members, either one may comprise a separate piano-convex member shaped to provide optical power, while the other of the optical components 4310 and 4350 comprises a planar member. The optical components 4310 and 4350 can be configured as a toric element.

One or more of the first and second components 4340*a*, 4340*b* may comprise a polymeric material as previously described herein. The first and second components 4340*a*, 4340*b* may be sufficiently flexible to be folded into a reduced cross-section delivery configuration for delivery to the eye as previously described herein. The first and second components 4340*a*, 4340*b* may be bonded to each other as previously described herein. The first and second components 4340*a*, 4340*b* may be fabricated as previously described herein. The third component (i.e., fixed lens 4330) may be sufficiently flexible to be folded into a reduced cross-section delivery configuration for delivery to the eye as well, and as described above, may be fixedly (e.g., permanently or releasably) coupled to the first or second components 4340a, 4340b in situ.

The fluid may comprise any of the fluids previously described herein. The fluid in the fluid chamber 4305 may provide optical power.

Figure 44:
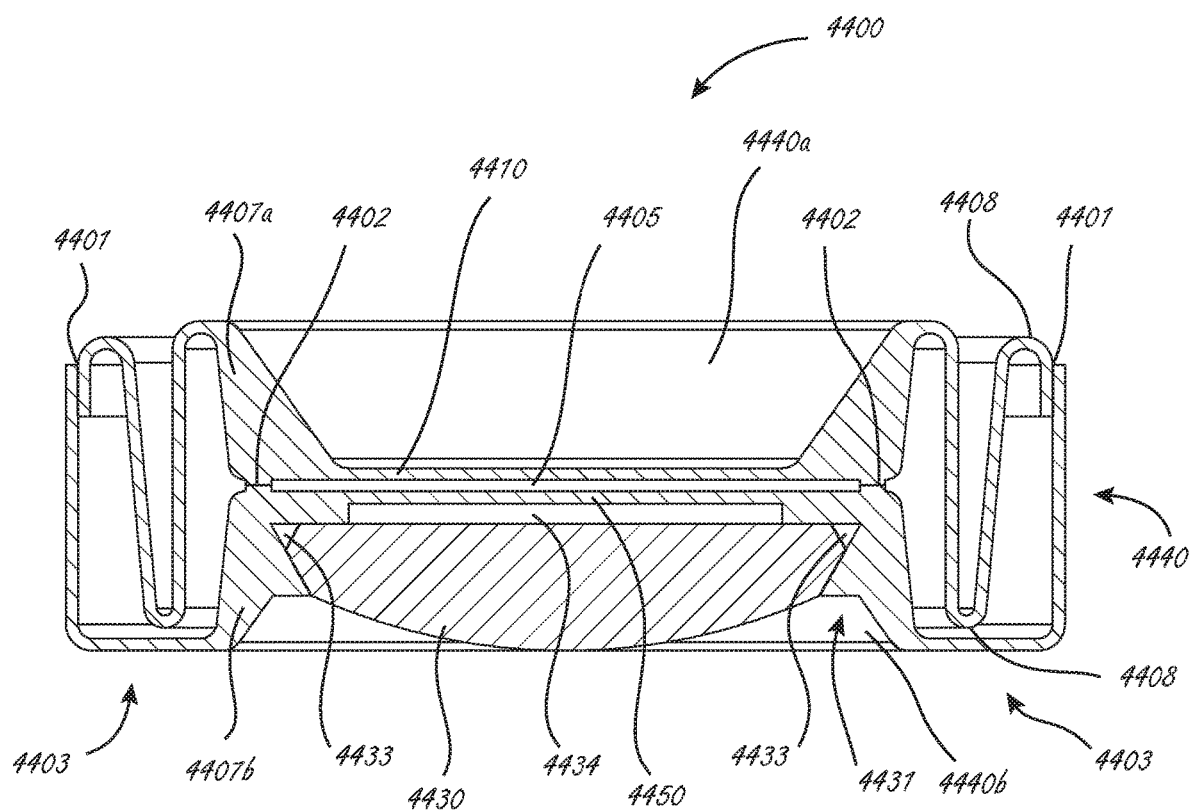
FIG. 44 shows a cross-sectional view of an alternate accommodating lens system in accordance with embodiments.

The dimensions and geometry of the accommodating lens systems described herein may be varied. For example, FIG. 44 illustrates an alternate AIOL system 4400 similar to AIOL system 4300 in which the last two digits of the reference numerals identify similar structures. The AIOL system 4400 differs from the AIOL system 4300 in that the AIOL system 4400 has a second optical component 4450 that is thinner than the second optical component 4350 of the second component 4340b. As a result, the second optical component 4450 may deform in a fashion which adds an optical power to the accommodating lens compared to the second optical component 4350 of the second component 4340b, which may be biased to provide no optical power. The thinning of the second optical component 4450 within the optical field of view additionally may be provided for by the relief 4434. The fluid reservoir 4403 also differs from the fluid reservoir 4303 in that the fluid reservoir 4403 may comprise two folds only in one half of the structure of 4440. For example, the outer region of the first component 4440a may comprise two folds 4408 while the outer region of the second component 4440b has none (e.g., the anterior half of the fluid reservoir 4403 comprises two folds 4408).

Figure 45:
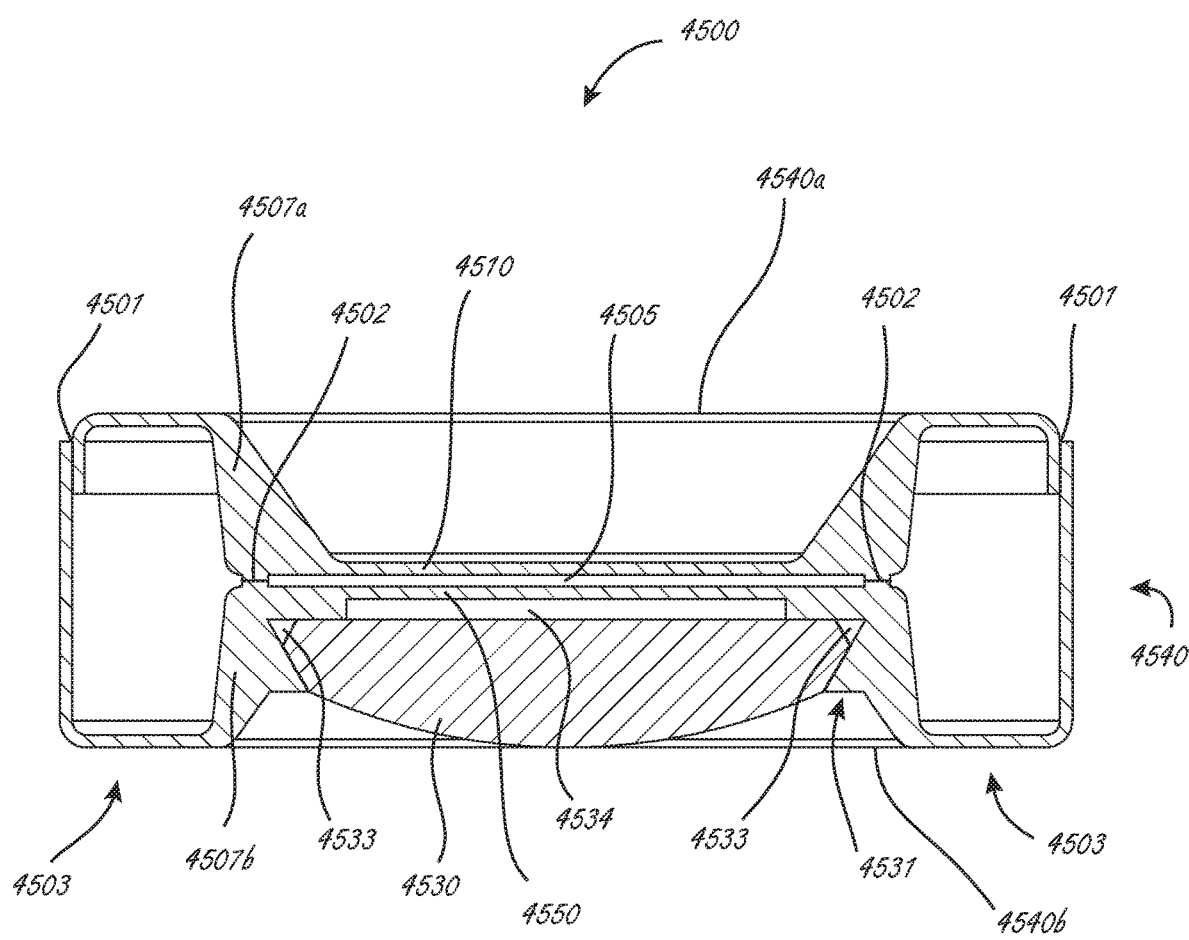
FIG. 45 shows a cross-sectional view of an alternate fluid filled accommodating lens system in accordance with embodiments.

In other examples, the geometry of the fluid-filled chamber or the bellows or other fluid reservoir structure may be varied. For example, FIG. 45 illustrates an AIOL system 4500, which is similar in structure to the AIOL system 4400, in which the last two digits of the reference numerals identify similar structures. The fluid-filled bellows structure 4503 may for example have a rectilinear cross-sectional shape extending circumferentially around the outer portion of the first and second components 4540a and 4540b.

The various peripheral fluid reservoir structures of the AIOLs 4200, 4300, 4400, and 4500 may provide a means of controlling the stiffness of the fluid reservoir and thereby the relation between varying accommodation and the forces applied by the eye on the structure as previously described herein.

Figure 46A:
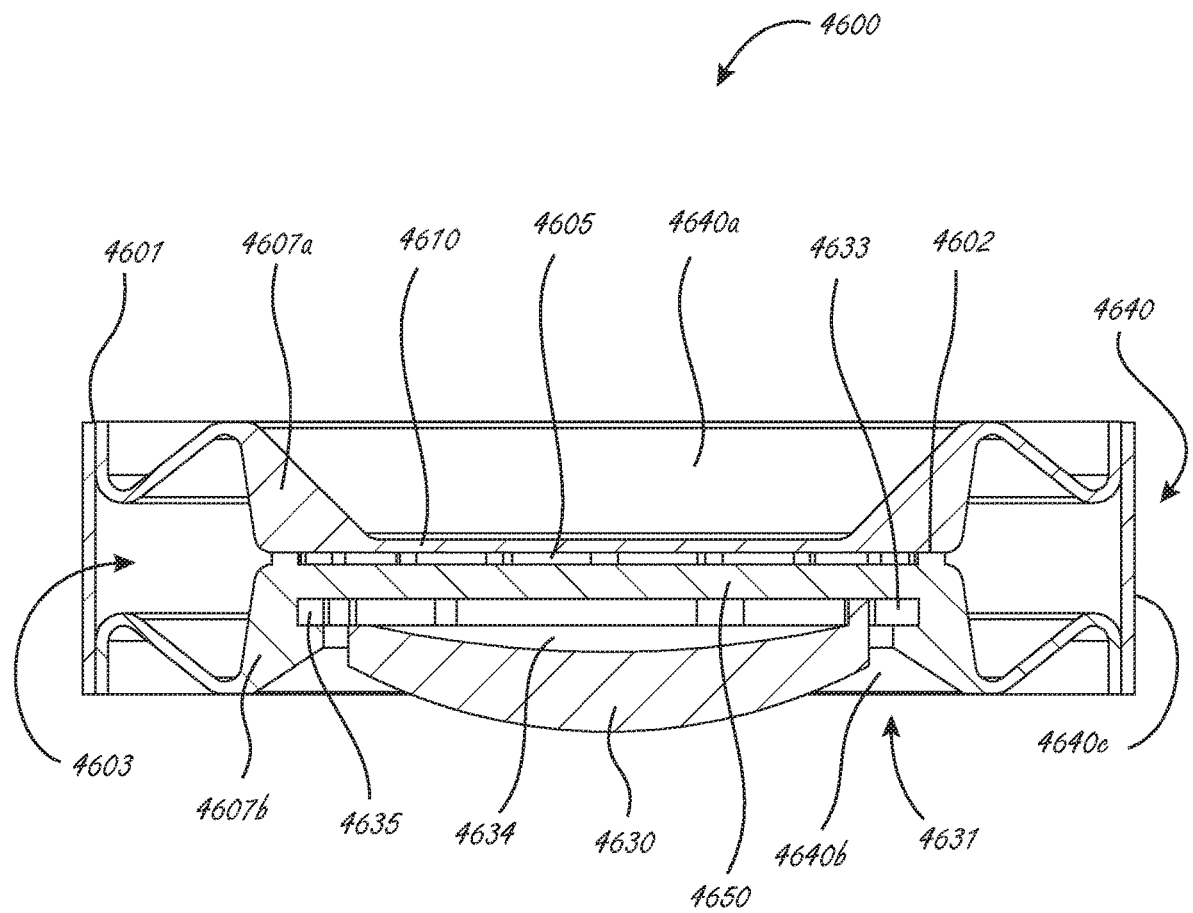
FIGS. 46A-46C illustrate an assembly of an alternate AIOL comprising four main parts, in accordance with embodiments.
Figures 46B, 46C:
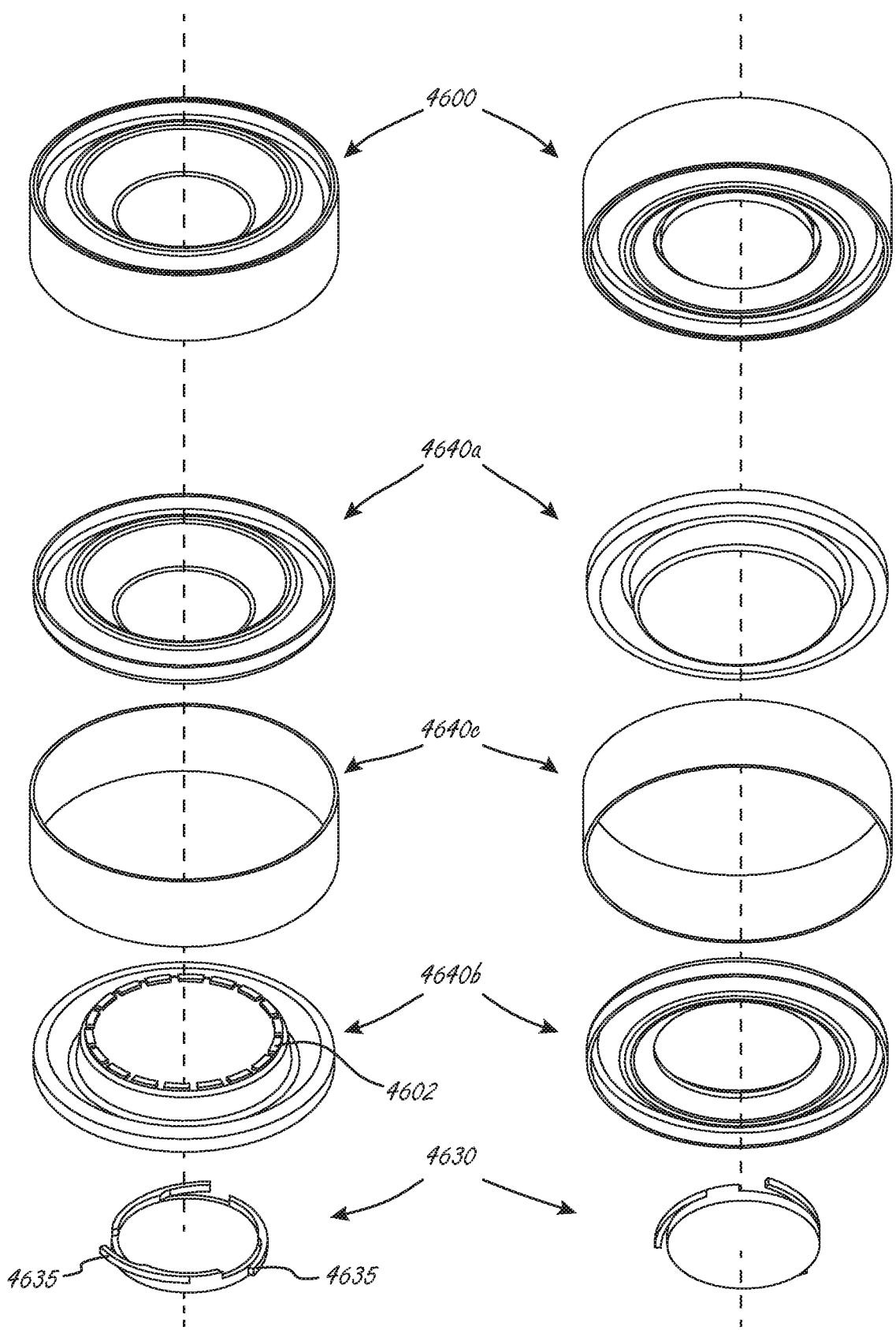

FIGS. 46A, 46B and 46C illustrate yet another embodiment of an AIOL system 4600 similar to the AIOL systems 4300, 4400, and 4500 described above, and the last two digits of the reference numerals identify similar structures in FIGS. 43-46C. The AIOL 4600 may be fabricated of four primary parts including a first component 4640a, a second component 4640b, a fixed lens structure 4630 defining the third component, and a thin-walled ring 4640c defining the fourth component. The AIOL 4600 includes a fluid reservoir 4603 defined by the thin-walled ring 4640c and the outer portions of the first and second components 4640a and 4640b. The thin-walled ring 4640c may be affixed to the first component 4640a and the second component 4640b at seams or joints 4601 such that the thin-walled ring 4640c couples the peripheries of the first and second components 4640a, 4640b to one another. The thin-walled ring 4640c may be fabricated of a material with different material properties than the rest of the components of the structure. In some embodiments, the thin-walled ring 4640c may be fabricated with a version of the polymer used to fabricate the first component 4640a and second component 4640b with a reduced modulus of elasticity. The thin-walled ring 4640c may therefore be more easily fabricated and fabricated with a thinner cross-section than might otherwise be possible. Alternatively, or in combination, the thin-walled ring 4640c can be spin cast or centripetally cast, thus allowing for structures even thinner than might be obtainable by machining. This particular embodiment is expected to provide good response to the movement of the native anatomy, and in a particular example it provides a larger response to lower pressures.

The fixed lens structure 4630 may for example comprise a convex-concave configuration. Haptic-like structures 4635 may be used to interlock in an interface feature 4631. A relief 4634 may be created by offsetting the haptic-like structures 4635 and the convex surface of the fixed lens 4630.

Figure 47:
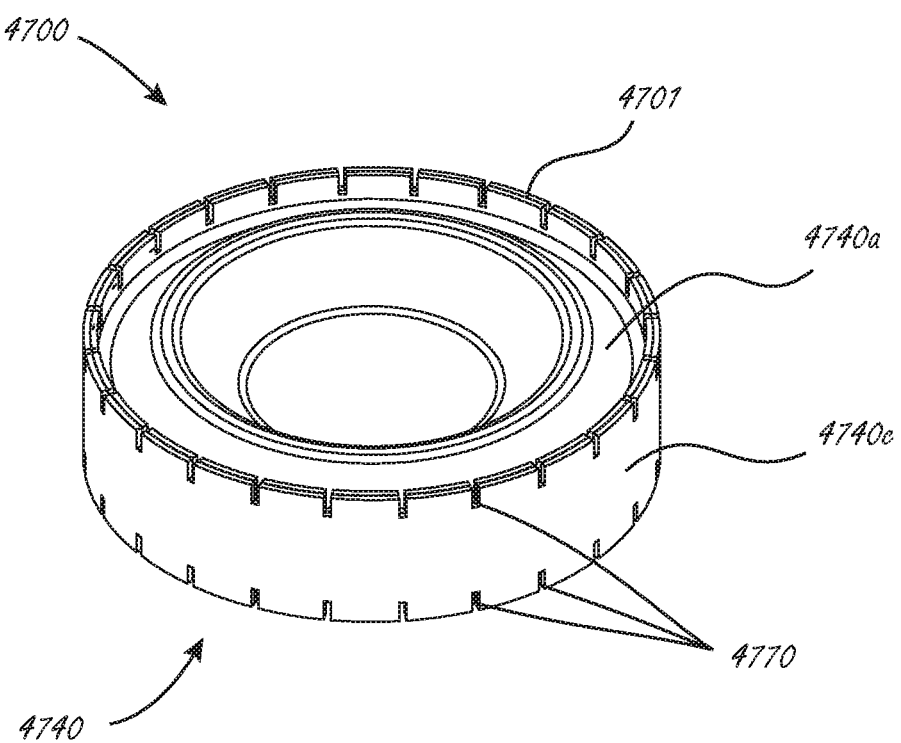
FIG. 47 is a completed assembly as embodied in FIGS. 46A-46C.

FIG. 47 illustrates an AIOL system 4700 which is a variation on the AIOL system 4600 shown in FIGS. 46A-46C. In FIG. 47, various structures are identified by various reference numerals and the last two digits of the reference numerals identify similar structures to those described above. The interfacing zones between the first component 4740a and the third component 4740c, and the interfacing zones between a second component, e.g., the second component 4640b shown in FIGS. 46B and 46C, and the third component 4740c, may have a plurality of slots 4770 to allow for a less rigid structure. The slots 4770 may be fabricated in the components of AIOL system 4700 before assembling the fluid-filled structure 4740, or the slots 4770 may be created after the components have been assembled. The slots 4770, when added after the structure has been assembled, may be created by one or more of mechanical cutting means, laser cutting, and any other suitable means. The slots 4770 may be created such that they extend partially down a seam so that a portion of the seam remains uncut and the seal between components of the AIOL remains.

Figure 48A:
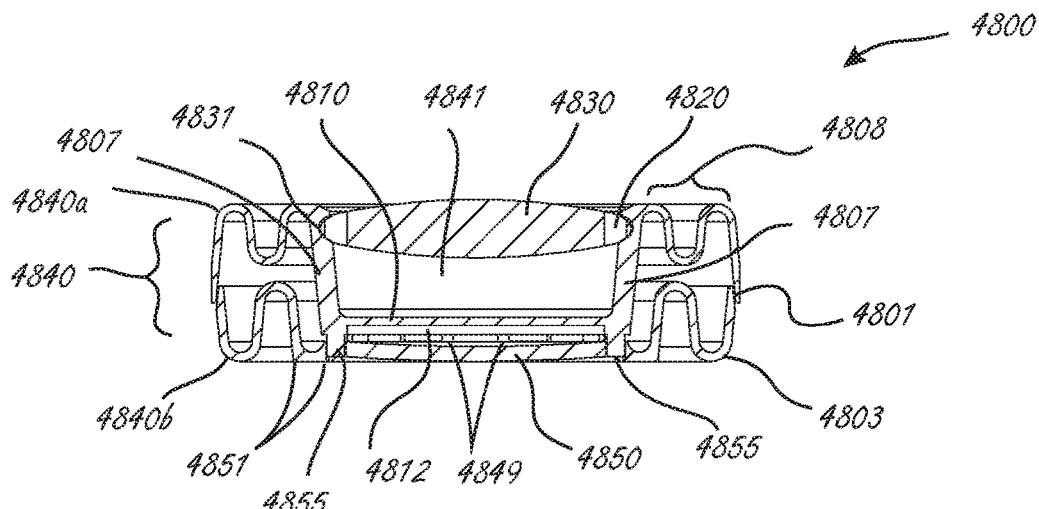
FIGS. 48A-48C illustrate an alternate AIOL comprising three main parts, in accordance with embodiments.
Figure 48B:
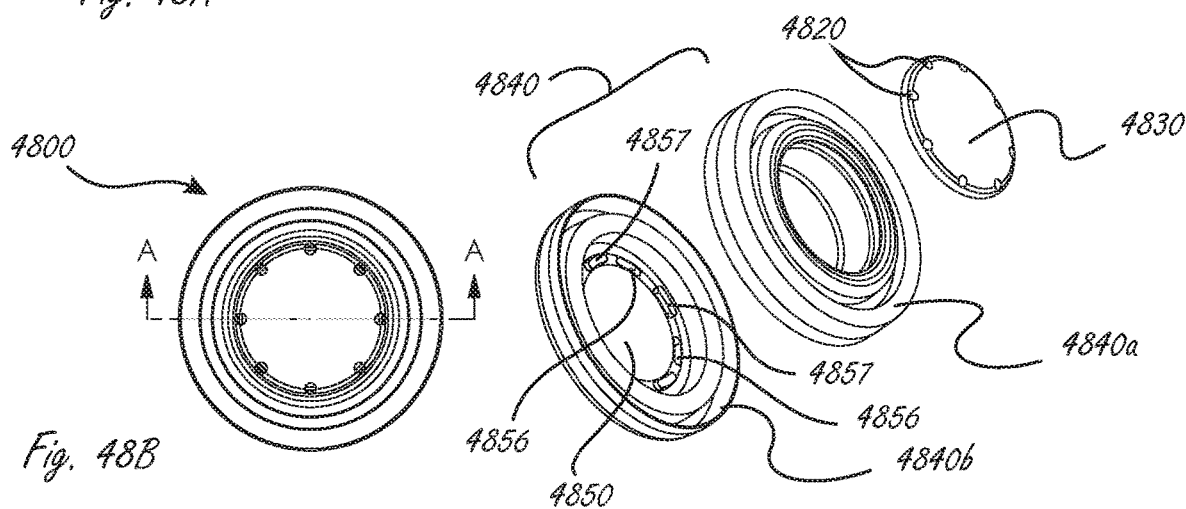
Figure 48C:
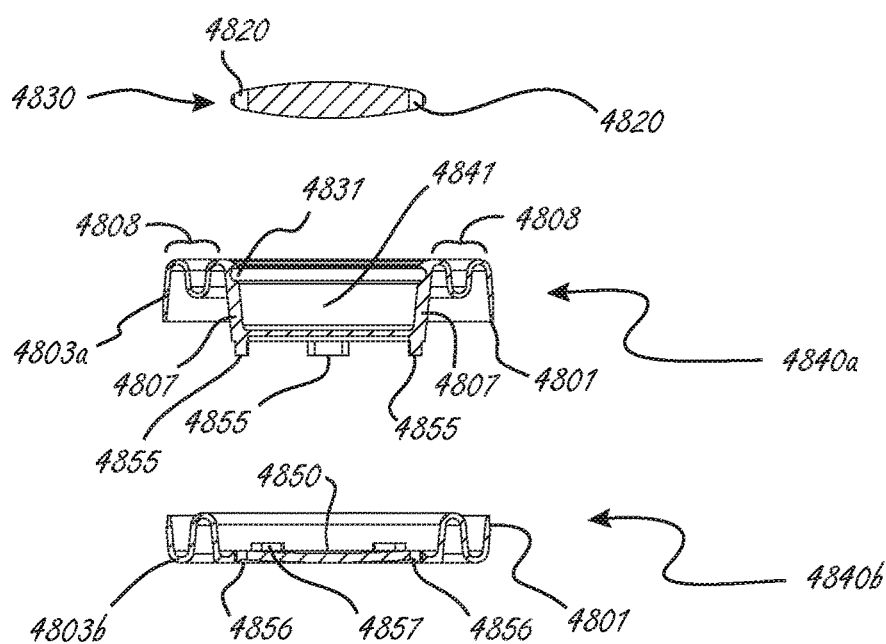

FIGS. 48A, 48B and 48C illustrate aspects of an alternate embodiment of an AIOL system 4800 similar to the embodiments of the AIOL systems 4300, 4400, 4500, 4600 and 4700, described above with reference to FIGS. 43-47. The AIOL system 4800 comprises a fixed lens 4830 and a fluid-filled structure 4840 including a first structural element 4840a and a second structural element 4840b. The first structural element 4840a can include an inner region defining a first optic component 4810, an annular stiff coupling region 4807 around the first optic component 4810, and an outer region 4808 around the stiff coupling region 4807. The stiff coupling region 4807 can be an annular wall that performs any of several functions: 1) it isolates the first optic component 4810 from external forces exerted against the outer region 4808 to maintain the optical integrity of the first optic component 4810, 2) it has a height that forms a cavity 4841 in the space between the fixed lens 4830 and the first optic component 4810, 3) it maintains a shape at the anterior end to securely hold the fixed lens 4830 in place as the fluid reservoir 4803 deforms, and 4) it defines a set inner boundary of the fluid reservoir 4803 so that optic fluid is directed into the accommodating lens. The first and second structural elements 4840a and 4840b are bonded together at seam 4801 to define a fluid reservoir 4803 at the outer portion 4808 of the fluid-filled structure 4840 as shown in the cross-section assembly view of FIG. 48A. The first structural element 4840a can be an anterior component facing anteriorly with respect to the native lens capsule such that the cavity 4841 defines an anterior space between the first optic component 4801 and the fixed lens 4830. The second structural element 4840b can include a second optic component 4850. The second optic component 4850 can be stiffer than the first optic component 4810. For example, the second optic component 4850 can be stiff (e.g., rigid) and the first optic component 4810 can be flexible.

The space 4812 between the first optic component 4810 and the second optic component 4850 can be filled with an optical fluid. The fluid-filled structure 4840 has fluid channels 4849 (FIG. 48A) between the fluid reservoir 4830 and the space 4812 between the first and second optic components 4810 and 4850. In operation, optical fluid passes between the fluid reservoir 4830 and the space 4812 in response to forces exerted by the native lens capsule. As pressure increases in the space 4812, at least the first optic component 4810 deflects anteriorly into the cavity 4841 toward the fixed lens 4830 to dynamically change the optical power of the AIOL system 4800 and provide accommodation. The optical fluid in the space 4812 and at least the first optic component 4810 accordingly define an accommodating lens.

Another feature of the AIOL system 4800 is the interface between the first structural element 4840a and the second structural element 4840b (best as seen in FIG. 48C). The first structural element 4840a can further comprise bonding pins 4855 and the second structural element can further comprise receivers 4856 configured to receive the bonding pins 4855. The bonding pins 4855 can project downwardly from the stiff coupling region 4807 of the first structural element 4840a in the orientation shown in FIG. 48C, and the receivers 4856 can be through holes around the perimeter of the second optic component 4850. The second structural element 4840b further comprises standoffs 4857 which, upon bonding the first and second structural elements 4840a-b together at the bonding pins 4855 and the receivers 4856 form fluid channels 4849 (FIG. 48A) to allow the optical fluid to flow between the fluid reservoir 4803 and the space 4812 between the first and second optic components 4850. Additionally, the fluid-filled structure 4840 can have a square edged annular region 4851 that provides for a barrier to cell migration from the periphery of the native lens capsule to the optical part of lens 4800. Such cell migration could cause post-surgery opacification of the optical system.

The fixed lens 4830 shown in FIGS. 48A and 48B includes at least one passage 4820, such as a hole or a cutout (e.g., recess), at the perimeter that allows aqueous fluid in the native lens capsule to pass through the fixed lens 4830 into and out of the cavity 4841. For example, the native aqueous fluid in the cavity 4841 passes through the passages 4820 in the fixed lens 4830 in response to the changes in shape of the first optic component 4810. The passages 4820 accordingly allow native aqueous fluid to wet the first optic component 4810 so that the first optic component 4810 maintains the desired performance while allowing the first optic component 4810 to deflect anteriorly while a liquid is in the cavity 4841.

The fixed lens 4830 can be attached to the stiff coupling region 4807 of the first structural element 4840a at a fixed lens receiver 4831 positioned at or near the anterior portion of the cavity 4841 (detailed in the cross-section of FIG. 48C). The fixed lens receiver 4831 and the fixed lens 4830 are configured so that the fixed lens 4830 can be attached to the first structural element 4840a and removed from the first structural element 4840a after the fluid-filled structure 4840 has been implanted in the native lens capsule. This is possible because the fixed lens 4830 is attached to the anterior portion of the fluid-filled structure 4840. This design allows for providing the correct fixed lens power needed for the patient at the time of the procedure after the accommodating fluid-filled portion 4840 has been placed in the native lens capsule. Moreover, since the fixed lens 4830 and the lens receiver 4831 are configured such that the fixed lens 4830 can be removed from the fluid-filled portion in situ, a fixed lens 4830 of one optical power can be replaced with a fixed lens 4830 of a different optical power to adjust the optical power of the fixed lens 4830 in situ. This configuration is expected to provide better efficacy because the shape of the accommodating lens unit may not be the same after it is implanted compared to before implantation, and thus the fixed optical power can be determined based on the actual shape and power of the accommodating lens unit after implantation. Also, the patients vision may change over time, and the fixed lens can be changed as the patients prescription changes.

Figure 49A:
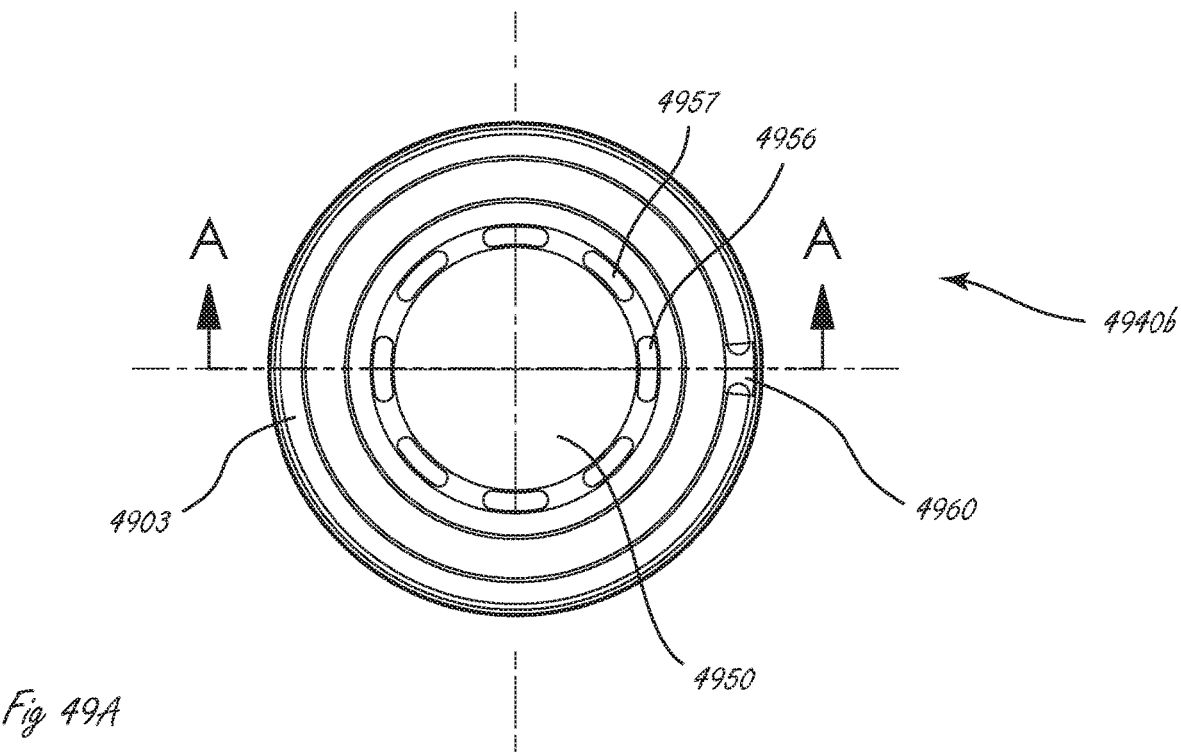
FIGS. 49A-49B illustrate another AIOL comprising three main parts, in accordance with embodiments.
Figure 49B:
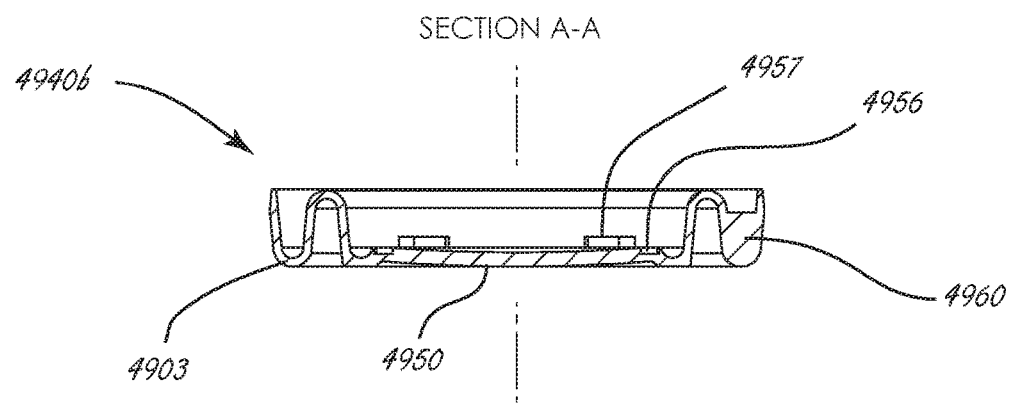

FIG. 49A is a top view and FIG. 49B is a cross-sectional side view of an alternate embodiment in which the second structural element 4840b of the embodiment shown in FIGS. 48A-48C is replaced with a second structural element 4940b. The second structural element 4940b comprises a thickened feature 4960 in a portion of the fluid reservoir 4903. As best shown in FIG. 49A, the thickened feature 4960 is at only one side of the second structural element 4940b, and the thickened feature 4960 extends around only a portion of the circumference of the second structural element 4940b. The thickened feature 4960 provides for a longer material path for use in accessing the interior of the completed assembly via a needle or tubular member for use in delivering a fluid into and removing gases from the interior of the assembly. The longer path of the needle through bulk material of 4960 provides for more surface area to seal the path when the tubular member is removed possibly eliminating the need for additional sealing measures after removal of a needle. As illustrated, the second structural element 4940b also comprises alternate receivers 4956 defined by recesses as opposed to the through hole receivers 4856 in the embodiment shown in FIG. 48C.

Figure 50:
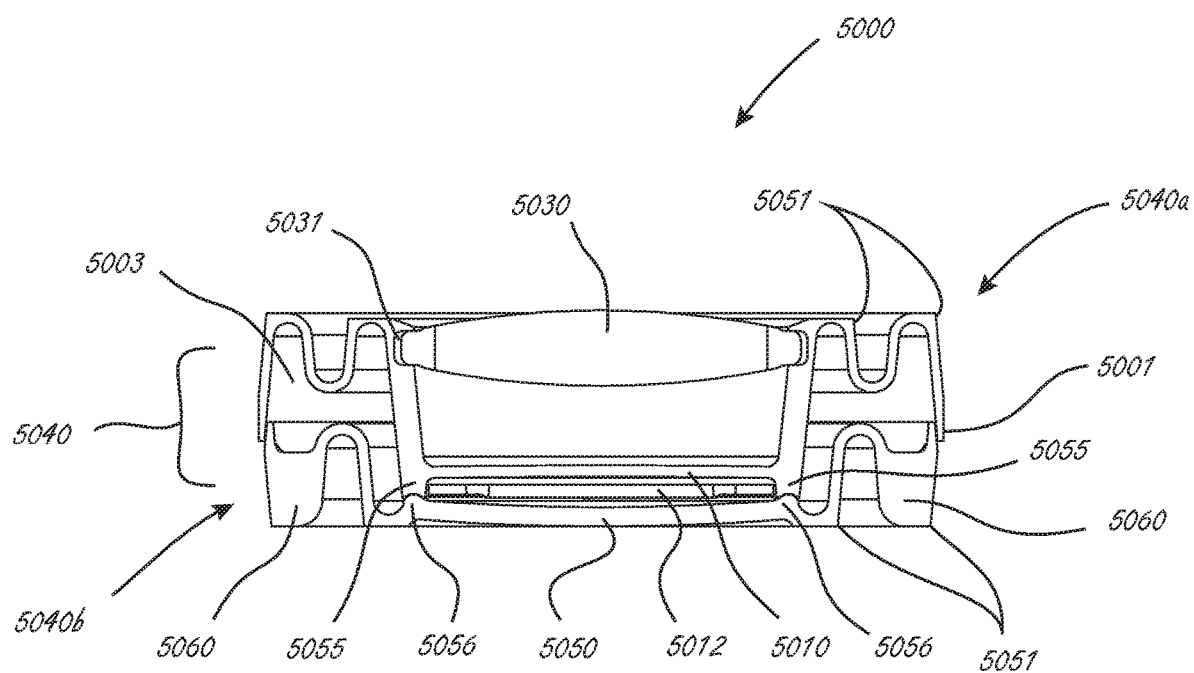
FIG. 50 depicts an alternate AIOL lens system comprising multiple square shaped annular regions edges.

FIG. 50 illustrates yet another embodiment of an AIOL system 5000 similar to the embodiments shown in FIGS. 48A-49B. The AIOL system 5000 includes a fixed lens 5030 and a fluid-filled unit 5040 having a first structural element 5040a and a second structural element 5040b. The second structural element 5040b includes multiple annular region 5051 with squared outer edges. These four annular regions 5051 incorporated in the posterior and anterior regions of the bellows structures provide additional protection against cell migration associated with posterior capsule opacification. The embodiment of the AIOL system 5000 additionally incorporates two thickened features 5060 diametrically opposed to each other to allow for fluid inflow and fluid outflow during the filling procedure. These features are shown in cross section and subtend circumferential angles similar to that of thickened feature 4960 shown in FIGS. 49A and 49B. The first structural element 5040a of the AIOL system 5000 further includes standoffs 5055 that interface with a continuous receiver ring 5056 of the second structural element 5040b. In FIG. 50, various structures are identified by various reference numerals and the last two digits of the reference numerals identify similar structures to those described in FIGS. 48A-49B.

Figure 51A:
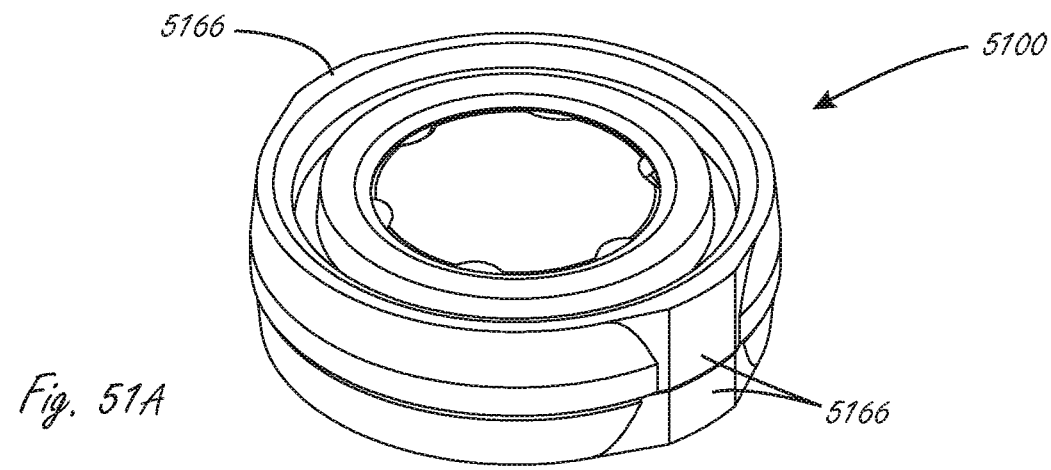
FIGS. 51A-51C Illustrates an embodiment incorporating a toric lens with indexing features and capsular rotation restraint.
Figure 51B:
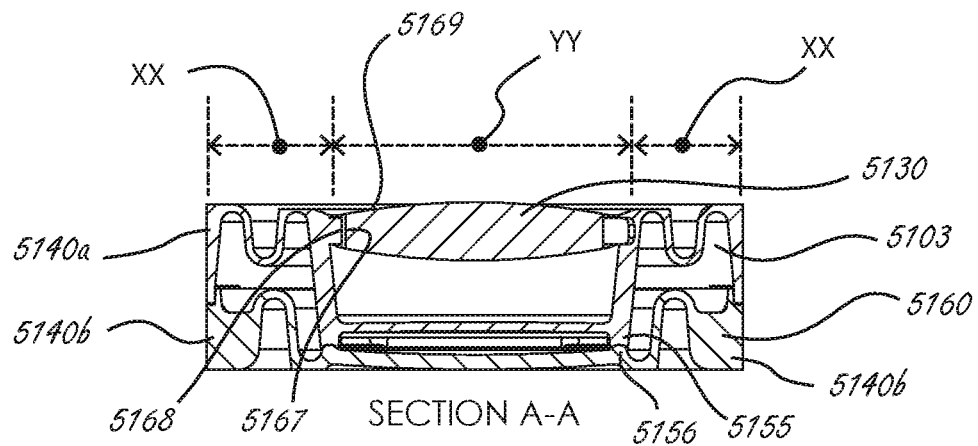
Figure 51C:
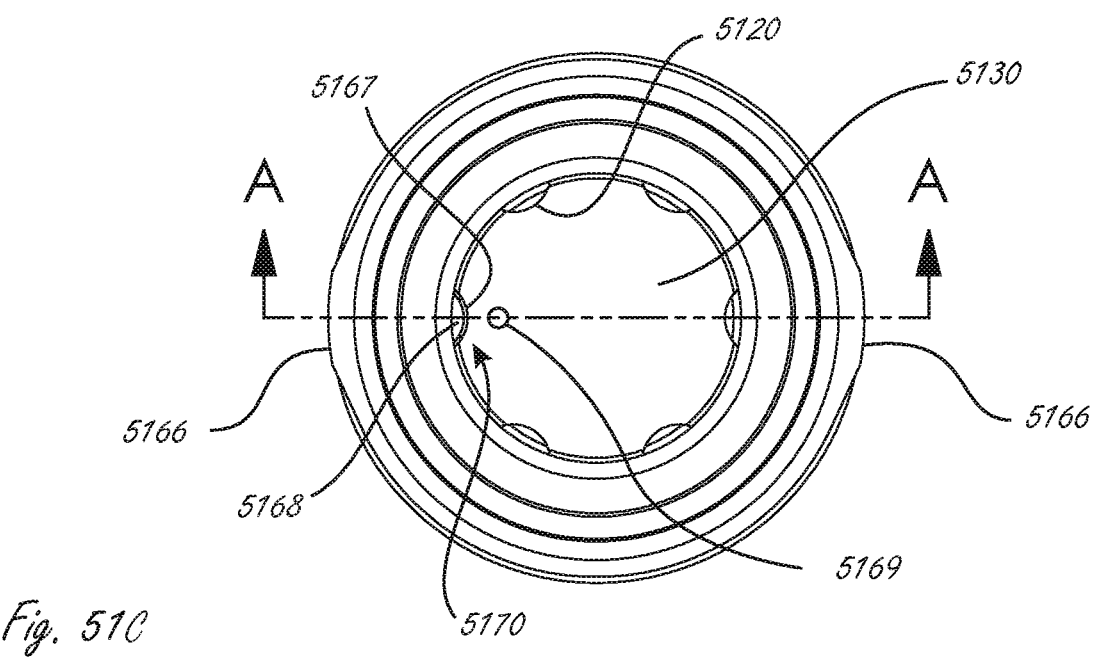
Figure 52A:
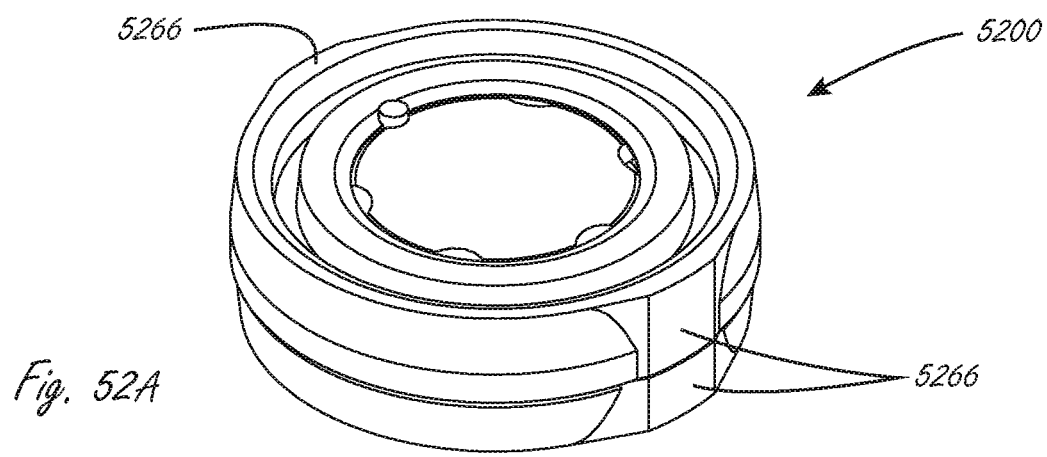
FIGS. 52A-52C Illustrates an alternate embodiment incorporating a toric lens with indexing features and capsular rotation restraint.
Figure 52B:
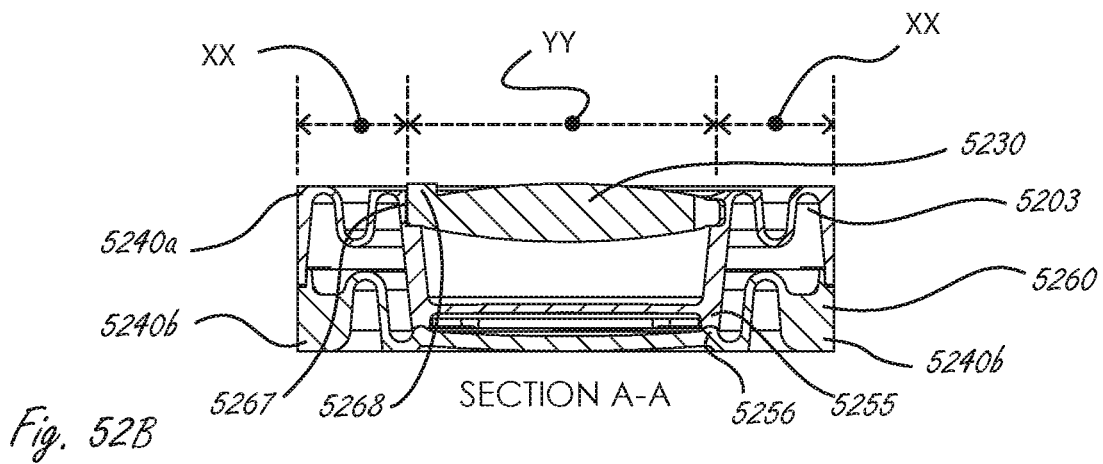
Figure 52C:
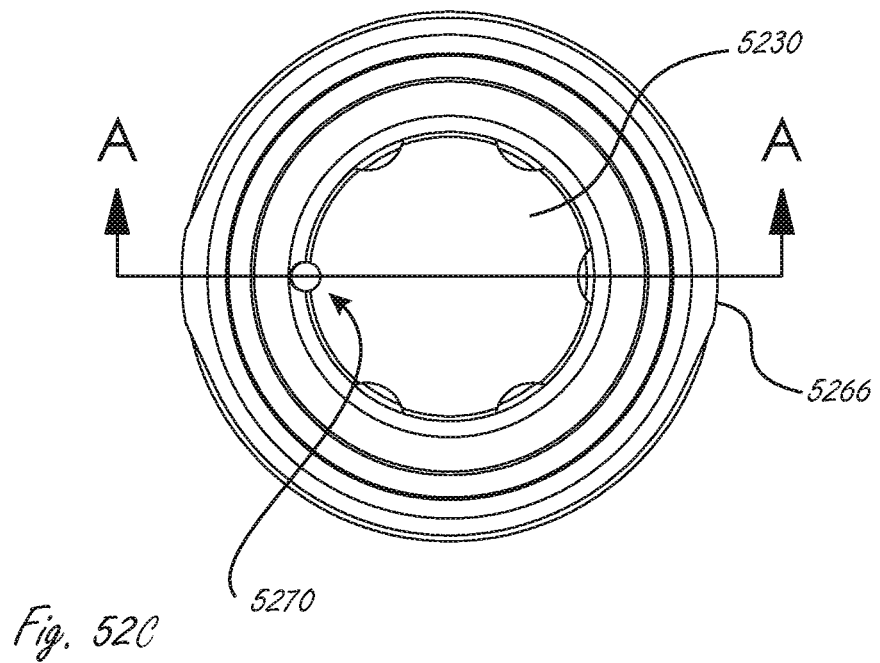

FIGS. 51 and 52 illustrate AIOL systems 5100 and 5200 similar to those illustrated in FIGS. 48A-50B in which additional features have been incorporated to enhance performance. Both embodiments comprise features to enhance performance when the AIOL system includes a toric lens. The toric lens may be in either the accommodating portion or the fixed portion. These features primarily minimize rotation of the optical components relative to themselves and or the capsule into which they have been implanted. As illustrated here the fixed lens 5130 or 5230 are configured to be toric. The AIOL systems 5100 and 5200 include capsular rotation constraints 5166 (FIGS. 51A and 51C) and 5266 (FIGS. 52A and 52C), respectively, on the outer periphery to engage the capsule and inhibit rotation of the AIOL systems 5100 and 5300 within the native lens capsule. The capsular rotational constraints 5166 and 5266 can be thickened portions of the first and/or second structural elements 5140a-b, 5240a-b on the outer periphery of the AIOL systems 5100 and 5200, respectively. Alternative embodiments for the capsular rotation constraints can be any feature that engages the native capsule more securely than other surfaces on the periphery. Alternatively, the AIOL systems 5100 or 5200 can have only one or more than two capsular rotation restraints 5166 or 5266.

In addition to the capsular rotational constraints 5166 and 5266, the AIOL systems 5100 and 5200 can also include features that rotationally maintain the orientation of the fixed lens relative to the accommodating portion of the AIOL system. The fixed lens rotational constraint or toric indexing features of the AIOL systems 5100 and 5200 provide for this function. The fixed lens 5130 of the AIOL system 5100 has a plurality of passages 5120 defined by cutouts or holes along the perimeter of the fixed lens 5130, and one of the passages 5120 defines a receiver 5167 at a location to guide the proper orientation of the fixed lens 5130 with respect to the first structural element 5140a. The first structural element 5140a comprises a key 5168 at a corresponding radial location to align a toric fixed lens 5130. The receiver 5167 and the key 5168 together define a toric indexing feature 5170. The fixed lens 5130 can further include a toric indexing mark 5169 on, or in, the fixed lens 5130 that identifies which passage 5120 the receiver 5167 is to be aligned with the key 5168. Alternatively, instead of having the toric indexing mark 5169, the key/receiver associated with the correct alignment can have a different shape (e.g., triangular) than the other passages 5120 in the lens (e.g., curved). FIG. 52 illustrates an alternate embodiment in which the receiver 5267 is a cutout or recess in the inner perimeter of the first structural element 5240a and the toric fixed lens 5230 comprises a key 5268 configured to mate with the receiver 5267.

The thickened regions of the capsular rotational constraints 5166 and 5266 of the AIOL systems 5100 and 5200 further provide a more robust leading edge for use when delivering the AIOL systems 5100 and 5200 through a narrow bore constriction or tube of an AIOL delivery device as described in copending provisional applications 62/334, 998, 62/331,407. One of the thickened rotational constraints 5166 and 5266 can be positioned to be a leading edge of the AIOL systems 5100 and 5200 and the other a trailing edge as they are passed through the narrow bore or tube of a delivery device. By having the thickened rotational constraints define a leading edge during delivery, the leading portion of the AIOL systems 5100, 5200 can sustain larger pressures as fluid is trapped in the leading section of the AIOL systems during the delivery process after the most distal portion has entered the constricted zone of the delivery tool.

Figure 53:
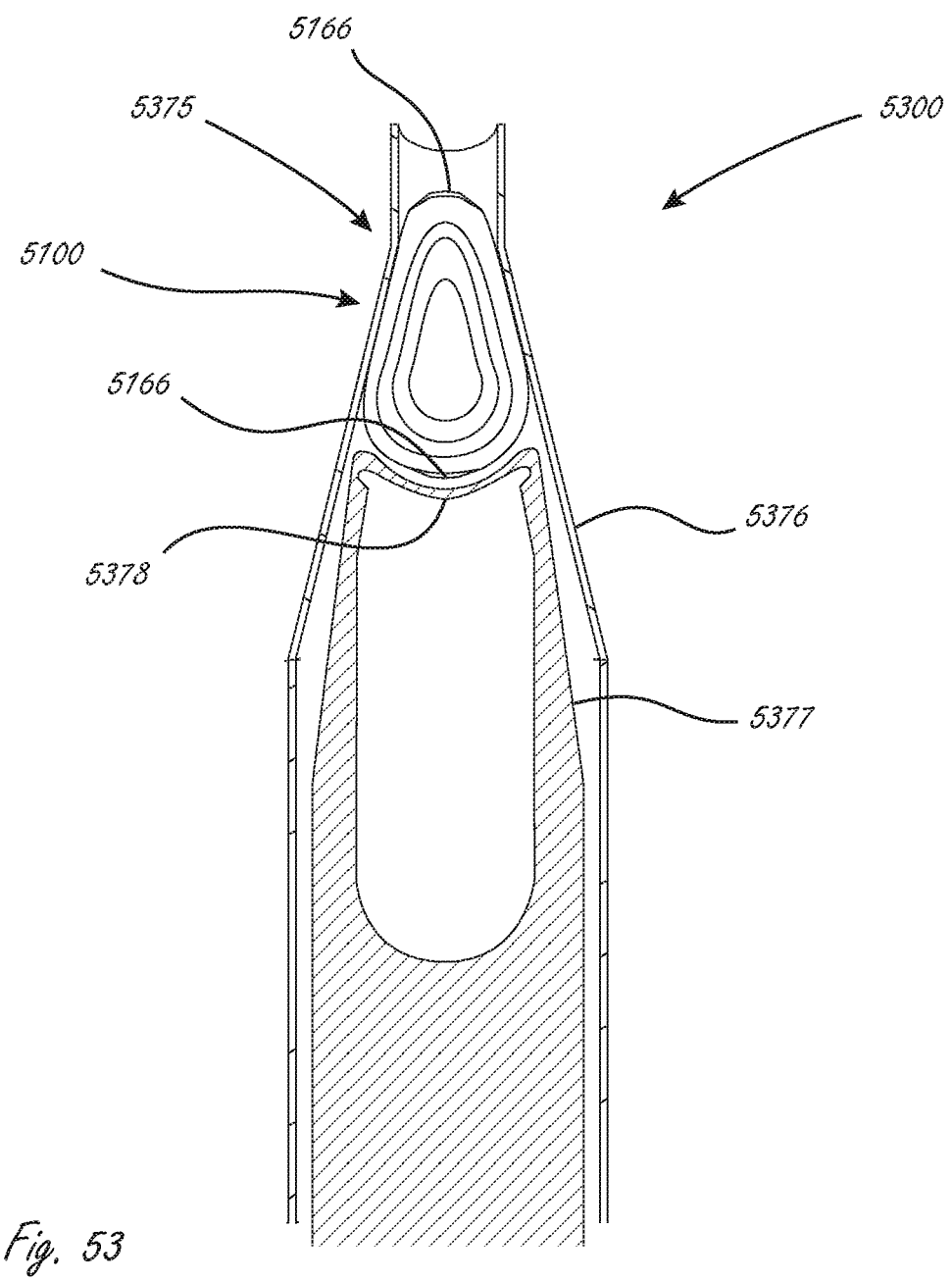
FIG. 53 Depicts an AIOL with capsular rotation restraints, properly positioned within a delivery device.

FIG. 53 schematically illustrates how one of the thickened rotational constraints 5166 of the AIOL system 5100 operates in a distal tip of a delivery device 5300 during delivery. The AIOL system 5100 is shown properly oriented relative to the capsular rotational constraints 5166 and entering the injector tip 5375 for delivery. The AIOL system 5100 conforms to the delivery tool constrictions while being pushed through the insertion funnel 5376 by the distal end of the plunger 5377 comprising a flexible distal end 5378. It will be appreciated that the internal pressure of the fluid in the AIOL system 5100 increases as it is compressed in the funnel 5376. The thickened rotational constraint 5166 at the leading edge provides more material to withstand the increase in pressure to prevent the front end from rupturing during delivery.

Figure 54A:
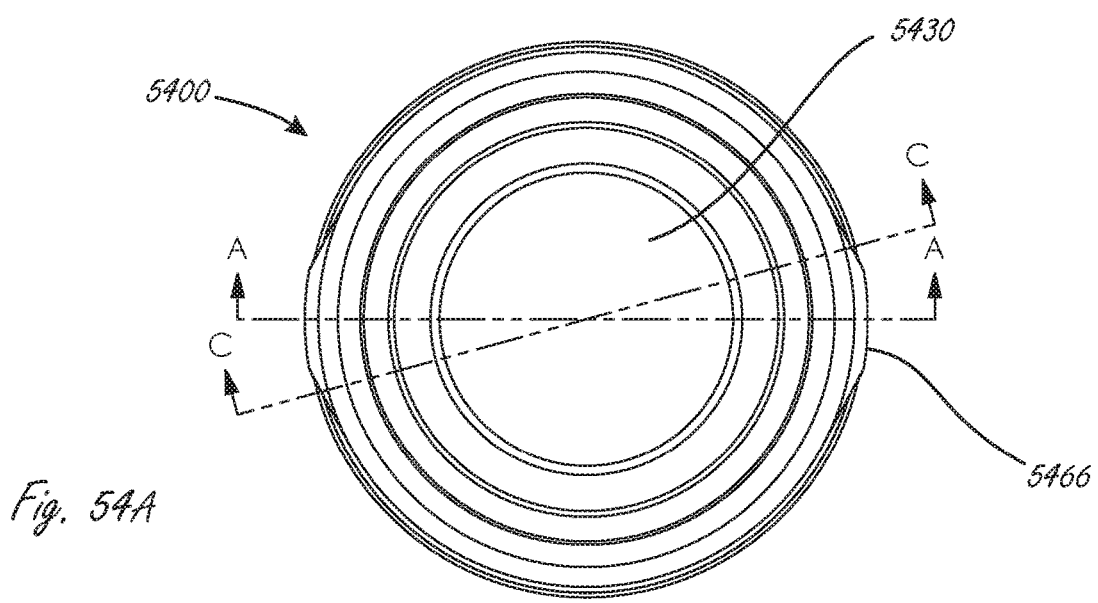
FIGS. 54A-54C present an alternate embodiment comprising a mid-bellows stabilizing feature.
Figure 54B:
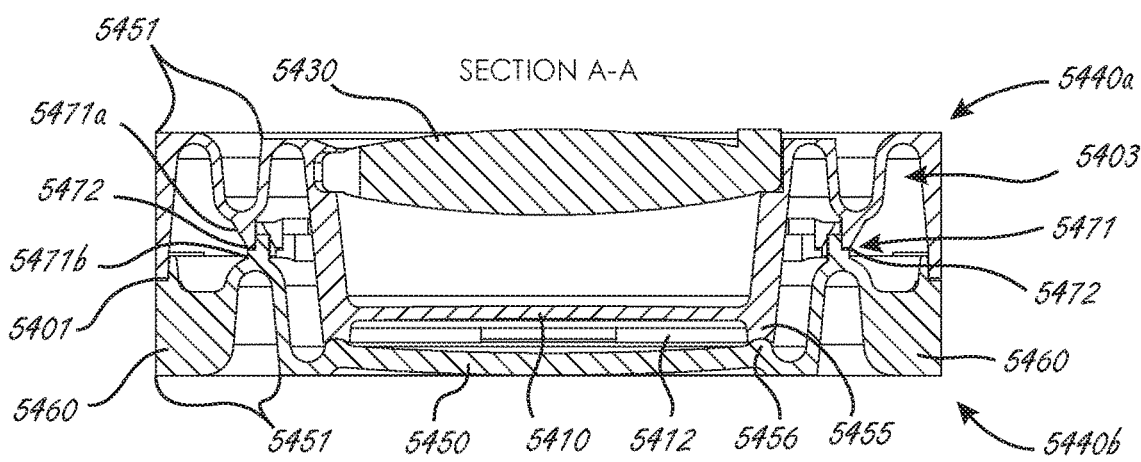
Figure 54C:
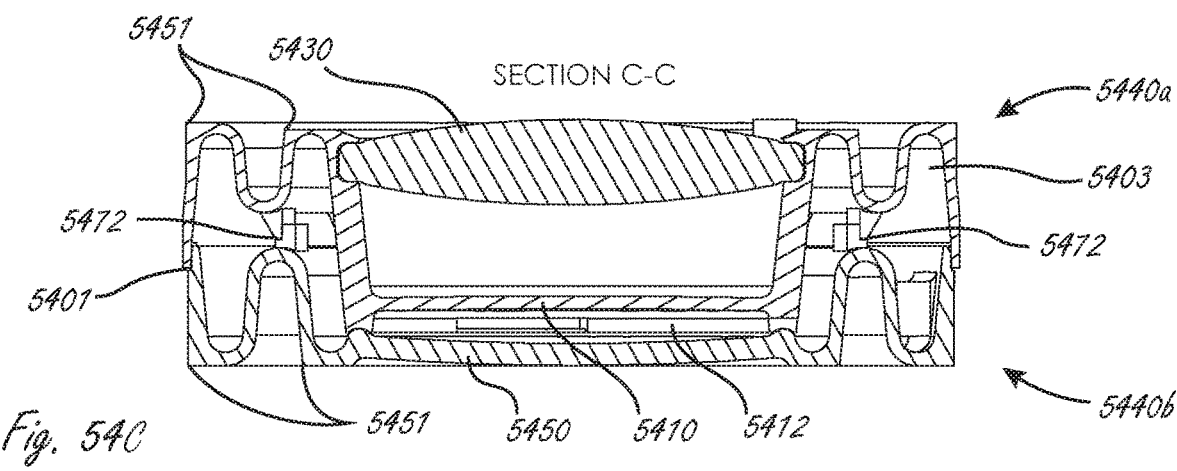

FIGS. 54A-54C illustrate an alternative AIOL system 5400 comprising at least one mid-bellows attachment feature 5471 (shown in the cross-sectional views of in FIGS. 54B-54C). The AIOL system 5400 is similar to the embodiment of the AIOL system 5200 described above. For example, the illustrated embodiment of the AIOL system 5400 comprises upper and lower structural elements 5440a and 5440b, respectively, that are bonded together at a seam 5401 that defines a bellows region 5403. The AIOL system 5400 further comprises a fixed lens 5430, a first optic component 5410, a second optic component 5450, and a space 5412 between the first and second optic components 5410 and 5450. At least one of the first and second optic components 5410 and 5450 is deformable (e.g., able to flex anteriorly and/or posteriorly), and in several embodiments the first optic component 5410 is more deformable than the second optic component 5450. For example, the first optic component 5410 can be a thin flexible member, while the second optic component 5450 is at least substantially rigid (e.g., does not flex in a manner that changes the optical power). The first optic component 5410 and/or the second optic component 5450 in combination with an optical fluid in the space 5412 define a fluid accommodating lens. The AIOL system 5400 also includes (a) thickened features 5460 that facilitate fluid delivery during the filling procedure as described above with respect to features 4960 and (b) a square shaped annular edge 5451 that provides a barrier to cell migration from the periphery of the patients capsule to portions of the AIOL system 5400 within the optical path.

The mid-bellows attachment features 5471 can each comprise upper and lower mating elements 5471a and 5471b integrated into the upper and lower structural elements 5440a and 5440b, respectively. The upper and lower mating elements 5471a and 5471b are joined together at a mating region 5472. The mid-bellows attachment features 5471 may be distributed circumferentially around the midsection of the bellows structure 5403 at a plurality of discrete locations that are spaced apart from each other. For example, in the embodiment of the AIOL system 5400 shown in FIGS. 54A-54C, the mid-bellows attachment features 5471 are evenly distributed at eight spaced apart locations (not shown) around the midsection of the bellows structure 5403, however the bellows attachment features 5471 are not limited to a specific quantity.

The mid-bellows attachment features 5471 are expected to provide a more efficient transfer of fluid from the bellows structure 5403 to the space 5412 of the accommodating lens. More specifically, without the mid-bellows attachment features 5471, the apexes of the periphery of the upper and lower structural elements 5404a and 5404b tend to separate from each other as pressure increases in the bellows structure 5403. The mid-bellows attachment features 5471 limit such undesirable or excessive expansion in the midsection of the bellows structure 5403 during accommodation by inhibiting separation of the apexes of the periphery of the upper and lower structural elements 5404a and 5404b. The mid-bellows attachment features 5471 accordingly stabilize the volume of the midsection of the bellows structure 5403 as fluid flows into the space 5412, which more efficiently transfers the accommodating fluid from the bellows structure 5403 to the space 5412 of the accommodating lens. FIG. 54B illustrates a section through the AIOL system 5400 which passes through two of the mid-bellows attachment features 5471, and FIG. 54C illustrates a section of the AIOL system 5400 that passes through two spaces between mid-bellows attachment features 5471 that allow fluid to pass from the outer perimeter of the bellows to the space 5412 of the fluid accommodating lens.

The mid-bellows attachment features 5471 are not limited to use in the embodiments of the AIOL system 5400 describe above with reference to FIGS. 54A-54C, but rather may be incorporated into any appropriate embodiment of an AIOL system disclosed herein. For example, several of the foregoing AIOL systems with a bellows structure can incorporate the mid-bellows attachment features 5471, such as but not limited to, embodiments of the AIOL systems 3900, 4100, 4200, 4300, 4400, 4800, 5000, 5200 and 5300.

Embodiments such as but not limited to any of those illustrated in FIGS. 43 through 54C may be constructed from parts in which some or all of the portions not in the optical path XX have been dyed or treated to reduce light throughput to limit the ability of stray light entering portions outside the optical path from scattering into the optical path YY as indicated in FIG. 51B.

The fixed lens described in any of the embodiments described herein may be of spheric, aspheric, toric, or any other known lens configuration. Alternatively, or in combination, the fixed solid lens may be piano-convex, convex-concave, or convex-convex. The fixed lens may be configured to have positive or have negative fixed power.

The fluid lenses described herein may be configured so as to have one or more accommodating surfaces, for example two accommodating surfaces.

In some embodiments, the optical fluid may be comprised of a high refractive index poly vinyl alcohol.

The AIOL devices described in FIGS. 43-54C (such as AIOLs 4300, 4400, 4500, 4600, 4700, 4800, 4900, 5000, 5100, 5200, 5400) may be implanted in the following fashion. The eye may be prepared and the native lens removed from the capsule in any appropriate manner. The fluid-filled structure may then be placed in the capsule of the eye. The patient may then be evaluated for a base optical power and or astigmatic correction in order to choose a fixed lens. The chosen fixed lens may then be inserted into the previously implanted fluid-filled structure of the AIOL. The chosen fixed lens may then be coupled to the fluid-filled structure within the eye capsule. As described above, one or more of the fluid-filled structure or fixed lens may each be flexible such that they may be reconfigured (e.g., folded) to a reduced-profile delivery configuration for delivery into the lens capsule. In some instances, it may be required to make a further correction to the fixed portion after the time of the surgery. Such instance may occur anywhere from days to years after the surgery. At such times the patient may return to the physician and the fixed lens may be replaced with a new fixed lens having a different optical power or other prescription. In such instances the new prescription may be characterized prior to or after removal of the original fixed lens. In some instances, the new fixed lens may be fabricated and implanted at the time of the examination, in others the patient may return for implantation of the fixed lens sometime after the examination.

In some embodiments the fixed portion of the AIOL may be fabricated from materials different from the accommodating portion. Such materials include hydrophilic or hydrophobic methacrylate or silicones and any other materials traditionally used in non-accommodating IOL's. the fixed lens may be fabricated from materials harder than those used for the accommodating portion.

Any of the features of the intraocular lens systems described in FIGS. 43-54 may be combined with any of the features of the other intraocular lenses described herein and vice versa.

While preferred embodiments of the present disclosure have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the disclosure described herein may be employed in practicing the disclosure. It is intended that the following claims define the scope of invention and that methods and structures within the scope of these claims and their equivalents be covered thereby.

We claim:

1. An accommodating intraocular lens assembly for placement within a lens capsule of a subject, comprising:
   an accommodating lens unit having a first optical component and a second optical component posterior with respect to the first optical component, wherein the first optical component and/or the second optical component is flexible such that flexion of the first optical component and/or the second optical component changes optical power of the accommodating lens unit; and
   a non-accommodating lens, the non-accommodating lens being configured to be removably coupled to the accommodating lens unit such that the non-accommodating lens is anterior of and spaced apart from the first optical component of the accommodating lens unit;
   wherein:
      the accommodating lens unit further comprises a fluid chamber between the first and second optical components, a reservoir fluidically coupled to the fluid chamber, and a flowable optic material in the fluid chamber and the reservoir, and wherein the first optical component and/or the second optical component flex in response to the optic material flowing between the fluid chamber and the reservoir to change the optical power;
      the accommodating lens unit further comprises a first structural element having the first optical component and a first outer portion around the first optical component, and a second structural element having the second optical component and a second outer portion around the second optical component; and
      the reservoir defined by first and second outer portions of the first and second structural elements is an annular bellows, and a flowable optic material flows between the annular bellows and the fluid chamber.

2. The accommodating intraocular lens assembly of claim 1 wherein the first optical component is flexible and the non-accommodating lens is spaced apart from the first optical component by a gap configured to allow the first optical component to flex anteriorly by an extent sufficient to provide a desired optical power for accommodation.

3. The accommodating intraocular lens assembly of claim 2 wherein the non-accommodating lens further includes passages configured to allow body fluid to flow into and out of the gap between the non-accommodating lens and the first optical component.

4. The accommodating intraocular lens assembly of claim 1 wherein the accommodating lens unit further comprises a fixed lens receiver and the non- accommodating lens is snap-fit into the fixed lens receiver.

5. The accommodating intraocular lens assembly of claim 1 wherein:
the first and second structural elements are bonded together to form the fluid chamber between the first and second optical components and to form the reservoir between the first and second outer elements; and
the non-accommodating lens is attached to the first outer portion of the first structural element.

6. The accommodating intraocular lens assembly of claim 1 wherein the first optical component is deflectable and the second optical component is at least substantially rigid such that anterior deflection of the first optical component and the flowable optic material in the fluid chamber provides optical power accommodation.

7. An accommodating intraocular lens assembly, comprising:
an accommodating lens unit having:
a first optical component;
a second optical component posterior with respect to the first optical component;
a fluid between the first and second optical components;
a wall projecting annularly from the first optical component; and
a retention feature along a radially-inward surface of the wall anterior with respect to the first and second optical components;
wherein -
the first optical component and/or the second optical component is flexible such that flexion of the first optical component and/or the second optical component in combination with the fluid between the first and second optical components changes optical power of the accommodating lens unit;
one of the first and second optical components is configured to releasably couple with a corrective lens; and
wherein one of the first and second optical components is configured to removably receive the corrective lens in-situ in an eye after the accommodating lens unit has been implanted in the eye.

8. The accommodating intraocular lens assembly of claim 7, wherein the retention feature is configured to releasably engage a corrective lens.

9. The accommodating intraocular lens assembly of claim 7 wherein the first optical component is flexible and the corrective lens is spaced apart from the first optical component by a gap configured to allow the first optical component to flex anteriorly by an extent sufficient to provide a desired optical power for accommodation.

10. The accommodating intraocular lens assembly of claim 9 wherein the corrective lens further includes passages configured to allow body fluid to flow into and out of the gap between the corrective lens and the first optical component.

11. The accommodating intraocular lens assembly of claim 7 wherein the accommodating lens unit further comprises a fixed lens receiver and the corrective lens is snap-fit into the fixed lens receiver.

12. The accommodating intraocular lens assembly of claim 7 wherein the accommodating lens unit further comprises a fluid chamber between the first and second optical components, a reservoir fluidically coupled to the fluid chamber, and a flowable optic material in the fluid chamber and the reservoir, and wherein the first optical component and/or the second optical component flex in response to the optic material flowing between the fluid chamber and the reservoir to change the optical power.

* * * * *